(12) United States Patent
Taketo et al.

(10) Patent No.: US 9,863,953 B2
(45) Date of Patent: Jan. 9, 2018

(54) METHOD FOR DETERMINING PROGNOSIS OF CANCER

(71) Applicant: KYOTO UNIVERSITY, Kyoto (JP)

(72) Inventors: Makoto Taketo, Kyoto (JP); Masahiro Sonoshita, New York City, NY (US); Yoshiharu Sakai, Kyoto (JP); Kenji Kawada, Kyoto (JP); Yoshiro Itatani, La Jolla, CA (US)

(73) Assignee: KYOTO UNIVERSITY, Kyoto (JP)

( * ) Notice: Subject to any disclaimer, the term of this patent is extended or adjusted under 35 U.S.C. 154(b) by 81 days.

(21) Appl. No.: 14/891,008

(22) PCT Filed: May 15, 2014

(86) PCT No.: PCT/JP2014/063527
§ 371 (c)(1),
(2) Date: Nov. 13, 2015

(87) PCT Pub. No.: WO2014/185550
PCT Pub. Date: Nov. 20, 2014

(65) Prior Publication Data
US 2016/0103133 A1 Apr. 14, 2016

(30) Foreign Application Priority Data

May 16, 2013 (JP) .................................. 2013-104027

(51) Int. Cl.
| | |
|---|---|
| *C07K 16/18* | (2006.01) |
| *C07K 16/30* | (2006.01) |
| *C07K 16/40* | (2006.01) |
| *G01N 33/574* | (2006.01) |
| *A61K 31/506* | (2006.01) |

(52) U.S. Cl.
CPC ..... *G01N 33/57496* (2013.01); *A61K 31/506* (2013.01); *C07K 16/18* (2013.01); *C07K 16/30* (2013.01); *C07K 16/3046* (2013.01); *C07K 16/40* (2013.01); *G01N 33/57446* (2013.01); *C07K 2317/34* (2013.01); *G01N 2333/91205* (2013.01); *G01N 2440/14* (2013.01)

(58) Field of Classification Search
None
See application file for complete search history.

(56) References Cited

U.S. PATENT DOCUMENTS

| | | | | |
|---|---|---|---|---|
| 4,208,479 | A * | 6/1980 | Zuk ..................... | C07J 41/0016 435/7.72 |
| 5,994,070 | A | 11/1999 | Streuli et al. | |
| 6,258,540 | B1 * | 7/2001 | Lo ....................... | C12Q 1/6879 435/440 |
| 6,355,623 | B2 * | 3/2002 | Seidman ............... | A61K 31/52 514/263.4 |

FOREIGN PATENT DOCUMENTS

| | | | |
|---|---|---|---|
| WO | WO 90/10234 A1 * | 9/1990 | ........... G01N 33/573 |
| WO | 97/35979 | 10/1997 | |

OTHER PUBLICATIONS

N1E-115 (ATCC® CRL-2263™, https://www.atcc.org/Products/All/CRL-2263.aspx?&p=1&rel=history#characteristics, retrieved Apr. 4, 2017).*
Macmillan Dictionary (Kit, http://www.macmillandictionary.com/dictionary/american/kit, retrieved Aug. 23, 2013).*
Hornbeck et al. (Current Protocols in Mol. Biol. Enzyme-Linked Immunosorbent Assays (ELISA) 2000, 11.2.1-11.2.22).*
WO 90/10234 A1 (Rijksen, G. Sep. 7, 1990).*
Supplementary Partial European Search Report dated Nov. 15, 2016 in corresponding European Application No. 14798641.8.
Kitadai et al., "Inhibition of reactive stroma by platelet derived growth factor receptor (PDGF-R) tyrosine kinase inhibitor reduces growth and lymph node metastasis of human colon carcinoma", European Journal of Cancer, vol. 6, No. 9, 2008, pp. 68.
Zheng et al., "TRIO Amplification and Abundant mRNA Expression is Associated with Invasive Tumor Growth and Rapid Tumor Cell Proliferation in Urinary Bladder Cancer", The American Journal of Pathology, vol. 165, No. 1, 2004, pp. 63-69.
Tobias Sjöblom et al., "The Consensus Coding Sequences of Human Breast and Colorectal Cancers", Science, 2006, vol. 314, pp. 268-274.
Laura D. Wood et al., "The Genomic Landscapes of Human Breast and Colorectal Cancers", Science, 2007, vol. 318, pp. 1108-1113.
Toshiaki Watanabe et al., "Molecular Predictors of Survival After Adjuvant Chemotherapy for Colon Cancer", The New England Journal of Medicine, 2001, vol. 344, pp. 1196-1206.
Joo Mi Yi et al., "Genomic and Epigenomic Integration Identifies a Prognostic Signature in Colon Cancer", Clinical Cancer Research, 2011, vol. 17, pp. 1535-1545.
Ramon Salazar et al., "Gene Expression Signature to Improve Prognosis Prediction of Stage II and III Colorectal Cancer", Journal of Clinical Oncology, 2011, vol. 29, No. 1, pp. 17-24.
Gordon Hutchins et al., "Value of Mismatch Repair, KRAS, and BRAF Mutations in Predicting Recurrence and Benefits From Chemotherapy in Colorectal Cancer", Journal of Clinical Oncology, 2011, vol. 29, No. 10, pp. 1261-1270.
Richard D. Kennedy et al., "Development and Independent Validation of a Prognostic Assay for Stage II Colon Cancer Using Formalin-Fixed Paraffin-Embedded Tissue", Journal of Clinical Oncology, 2011, vol. 29, No. 35, pp. 4620-4626.
Andreas Androutsellis-Theotokis et al., "Notch signalling regulates stem cell numbers in vitro and in vivo", Nature, 2006, vol. 442, No. 17, pp. 823-826.
Lionel Arnaud et al., "Fyn Tyrosine Kinase is a Critical Regulator of Disabled-1 during Brain Development", Current Biology, 2003, vol. 13, pp. 9-17.

(Continued)

*Primary Examiner* — Peter J Reddig
(74) *Attorney, Agent, or Firm* — Wenderoth, Lind & Ponack, L.L.P.

(57) ABSTRACT

The present invention relates to a method for determining prognosis of cancer in a subject, which comprises the step of detecting phosphorylation of a tyrosine residue at position 2681 of TRIO in a sample obtained from the subject.

13 Claims, 44 Drawing Sheets

(56) References Cited

OTHER PUBLICATIONS

Spyros Artavanis-Tsakonas et al., "Notch Signaling: Cell Fate Control and Signal Integration in Development", Science, 1999, vol. 284, pp. 770-776.
Daniela Barila et al., "A nuclear tyrosine phosphorylation circuit: c-Jun as an activator and substrate of c-Abl and JNK", The EMBO Journal, 2000, vol. 19, No. 2, pp. 273-281.
Jack Bateman et al., "The Trio family of guanine-nucleotide-exchange factors: regulators of axon guidance", Journal of Cell Science, 2001, vol. 114, pp. 1973-1980.
Daniel D. Billadeau, "Vav Proteins in Cancer", In The Rho GTPases in Cancer, Springer Science + Business Media, LLC, 2010, pp. 77-92.
Nikolaj Blom et al., "Sequence and Structure-based Prediction of Eukaryotic Protein Phosphorylation Sites", Journal of Molecular Biology, 1999, vol. 294, pp. 1351-1362.
Hans H. Bock et al., "Reelin Activates Src Family Tyrosine Kinases in Neurons", Current Biology, vol. 13, 2003, pp. 18-26.
Elisabeth Buchdunger et al., "Bcr-Abl inhibition as a modality of CML therapeutics", Biochimica et Biophysica Acta, vol. 1551, 2001, pp. M11-M18.
Wei-Shone Chen et al., "Comparative Tyrosine-Kinase Profiles in Colorectal Cancers: Enhanced ARG Expression in Carcinoma as Compared With Adenoma and Normal Mucosa", Int. J. Cancer, vol. 83, 1999, pp. 579-584.
John Colicelli, "ABL Tyrosine Kinases: Evolution of Function, Regulation, and Specificity", Science Signal, 2010, vol. 3, pp. 1-46.
Anne Debant et al., "The multidomain protein Trio binds the LAR transmembrane tyrosine phosphatase, contains a protein kinase domain, and has separate rac-specific and rho-specific guanine nucleotide exchange factor domains", Proc. Natl. Acad. Sci., 1996, vol. 93, pp. 5466-5471.
Jonathan Degeer et al., "Tyrosine Phosphorylation of the Rho Guanine Nucleotide Exchange Factor Trio Regulates Netrin-1/DCC-Mediated Cortical Axon Outgrowth", Molecular and Cellular Biology, 2013, vol. 33, No. 4, pp. 739-751.
Robin D. Dowell, "Transcription factor binding variation in the evolution of gene regulation", Trends in Genetics, 2010, vol. 26, No. 11, pp. 468-475.
Isaiah J. Fidler, "The pathogenesis of cancer metastasis: the 'seed and soil' hypothesis revisited", Nature Reviews, 2003, vol. 3, pp. 453-458.
David J. Forsthoefel et al., "The Abelson tyrosine kinase, the Trio GEF and Enabled interact with the Netrin receptor Frazzled in *Drosophila*", Development, 2005, vol. 132, pp. 1983-1994.
Yuan Gao et al., "Rational design and characterization of a Rac GTPase-specific small molecule inhibitor", Proc. Natl. Acad. Sci., 2004, vol. 101, No. 20, pp. 7618-7623.
Edward Giniger, "A Role for Abl in Notch Signaling", Neuron, 1998, vol. 20, pp. 667-681.
Edward Giniger, "Notch signaling and neural connectivity", Curr. Opin. Genet. Dev., 2012, vol. 22, No. 4, pp. 339-346.
Alan Hall, "Rho GTPases and the Actin Cytoskeleton", Science, 1998, vol. 279, pp. 509-514.
A. Hall, "The cytoskeleton and cancer", Cancer Metastasis Rev., 2009, vol. 28, pp. 5-14.
Hua Han et al., "Inducible gene knockout of transcription factor recombination signal binding protein-J reveals its essential role in T versus B lineage decision", International Immunology, 2002, vol. 14, No. 6, pp. 637-645.
Oliver Hantschel et al., "Regulation of the C-ABL and BCR-ABL Tyrosine Kinases", Nat. Rev. Mol. Cell Bio, vol. 5, 2004, pp. 33-44.
K. Hashimoto-Torii et al., "Interaction between Reelin and Notch signaling regulates neuronal migration in the cerebral cortex", Neuron, 2008, vol. 60, No. 2, pp. 273-284.
Brian W. Howell et al., "Mouse disabled (mDab1): Src binding protein implicated in neuronal development", The EMBO Journal, 1997, vol. 16, No. 1, pp. 121-132.

Yoshihiro Kawasaki et al., "Asef, a link Between the Tumor Suppressor APC and G-Protein Signaling", Science, 2000, vol. 289, pp. 1194-1197.
Fumihiko Kakizaki et al., "CDX Transcription Factors Positively Regulate Expression of Solute Carrier Family 5, Member 8 in the Colonic Epithelium", Gastroenterology, 2010, vol. 138, pp. 627-635.
Alena Krejci et al., "Direct Response to Notch Activation: Signaling Crosstalk and Incoherent Logic", Science Signaling, 2009, vol. 2, issue 55, pp. 1-14.
Yaochen Li et al., "Genome-wide analysis of N1ICD/RBPJ targets in vivo reveals direct transcriptional regulation of Wnt, SHH, and Hippo pathway effectors by Notch 1", Stem Cells, 2012, vol. 30, No. 4, pp. 741-752.
W. Gregory Feero et al., "Genomics and the Continuum of Cancer Care", The New England Journal of Medicine, 2011, vol. 364, pp. 340-350.
Quintus G. Medley et al., "The Trio Guanine Nucleotide Exchange Factor is a RhoA Target", The Journal of Biological Chemistry, 2000, vol. 275, No. 46, pp. 36116-36123.
Fayth L. Miles et al., "Stepping out of the flow: capillary extravasation in cancer metastasis", Clin. Exp. Metastasis, 2008, vol. 25, pp. 305-324.
David T. Nellesen et al., "Discrete Enhancer Elements Mediate Selective Responsiveness of Enhancer of split Complex Genes to Common Transcriptional Activators", Developmental Biology, 1999, vol. 213, pp. 33-53.
Masanobu Oshima et al., "Loss of Apc heterozygosity and abnormal tissue building in nascent intestinal polyps in mice carrying a truncated Apc gene", Proc. Natl. Acad. Sci., 1995, vol. 92, pp. 4482-4486.
Matthew D. Rand et al., "Calcium Depletion Dissociates and Activates Heterodimeric Notch Receptors", Molecular and Cellular Biology, 2000, vol. 20, pp. 1825-1835.
Prathibha Ranganathan et al., "Notch signalling in solid tumours: a little bit of everything but not all the time", Nat. Rev. Cancer, vol. 11, 2011, pp. 338-351.
Nicolas Reymond et al., "Rho GTPases and Cancer Cell Transendothelial Migration", Methods in Molecular Biology, vol. 827, 2012, pp. 123-142.
Kent L. Rossman et al., "A crystallographic view of interactions between Dbs and Cdc42: PH domain-assisted guanine nucleotide exchange", The EMBO Journal, 2002, vol. 21, No. 6, pp. 1315-1326.
Kamon Sanada et al., "Disabled-1-Regulated Adhesion of Migrating Neurons to Radical Glial Fiber Contributes to Neuronal Positioning during Early Corticogenesis", Neuron, 2004, vol. 42, pp. 197-211.
Charles L. Sawyers, "Opportunities and challenges in the development of kinase inhibitor therapy for cancer", Genes & Development, 2003, vol. 17, pp. 2998-3010.
Jeong K. Song et al., "Non-canonical Notch function in motor axon guidance is mediated by Rac GTPase and the GEF1 domain of Trio", Dev. Dyn., 2011, vol. 240, pp. 324-332.
Masahiro Sonoshita et al., "Suppression of Colon Cancer Metastasis by Aes through Inhibition of Notch Signaling", Cancer Cell, 2011, vol. 19, pp. 125-137.
Patricia S. Steeg, "Metastasis Suppressors Alter the Signal Transduction of Cancer Cells", Nature Reviews, 2003, vol. 3, pp. 55-63.
Robert Steven et al., "UNC-73 Activates the Rac GTPase and is Required for Cell and Growth Cone Migrations in C. elegans", Cell, 1998, vol. 92, pp. 785-795.
Kittichoat Tiyanont et al., "Evidence for Increased Exposure of the Notch1 Metalloprotease Cleavage Site upon Conversion to an Activated Conformation", Structure, 2011, vol. 9, No. 4, pp. 546-554.
Barbara Varnum-Finney et al., "Immobilization of Notch Ligand, Delta-1, is required for induction of Notch signaling", Journal of Cell Science, 2000, vol. 113, pp. 4313-4318.
Dominico Vigin et al., "Ras superfamily GEFs and GAPs: validated and tractable targets for cancer therapy?", Nat. Rev. Cancer, 2010, vol. 10, No. 12, pp. 842-857.

(56) References Cited

OTHER PUBLICATIONS

Marc Vooijs et al., "Notch: Architect, Landscaper, and Guardian of the Intestine", Gastroenterology, 2011, vol. 141, No. 2, pp. 448-459.
R.A. Weinberg, "Cellular Oncogenes", In the Biology of Cancer, (New York: Garland Science), 2007a, chapter 4, pp. 103-130.
R.A. Weinberg, "Moving out: invasion and metastasis", In the Biology of Cancer, (New York: Garland Science), 2007b, chapter 14, pp. 641-722.
Naoto Yoshizuka et al., "An Alternative Transcript Derived from the Trio Locust Encodes a Guanosine Nucleotide Exchange Factor with Mouse Cell-transforming Potential", The Journal of Biological Chemistry, 2004, vol. 279, No. 42, pp. 43998-44004.
Yasuhiko Kitadai et al., "Inhibition of reactive stroma by PDGFR tyrosine kinase inhibitor reduces growth and metastasis of human colon carcinoma", Shokakika, 2007, vol. 44, No. 5, pp. 463-467, cited in ISR.
Quintus G. Medley et al., "Signaling between Focal Adhesion Kinase and Trio", The Journal of Biological Chemistry, 2003, vol. 278, No. 15, pp. 13265-13270.
Jose P. Vaque et al., "A Genome-wide RNAi Screen Reveals a Trio-Regulated Rho GTPase Circuitry Transducing Mitogenic Signals Initiated by G Protein-Coupled Receptors", Molecular Cell, 2013, vol. 49, pp. 94-108.
M.A. Pantaleo et al., "Targeted therapy in colorectal cancer: do we know enough?", Digestive and Liver Disease, 2006, vol. 38, No. 2, pp. 71-77.
International Preliminary Report on Patentability dated Nov. 17, 2015 in International Application No. PCT/JP2014/063527.
International Search Report dated Aug. 26, 2014 in International Application No. PCT/JP2014/063527.
Extended European Search Report dated Mar. 23, 2017 in corresponding European Application No. 16204647.8.
Kelly et al., "A phase 1 trial of imatinib bevacizumab, and metronomic cyclophosphamide in advanced colorectal cancer", British Journal of Cancer, vol. 109, No. 7, 2013, pp. 1725-1734.
Hoehler et al., "Phase I/II trial of capecitabine and oxaliplatin in combination with bevacizumab and imatinib in patients with metastatic colorectal cancer: AIO KRK 0205", British Journal of Cancer, vol. 109, No. 6, 2013, pp. 1408-1413.
Michael et al., "A phase I trial of imatinib in combination with mFOLFOX6-bevacizumab in patients with advanced colorectal cancer", Cancer Chemotherapy and Pharmacology, vol. 71, No. 2, 2012, pp. 321-330.
Pessino et al., "6075 A triple combination of Imatinib, Bevacizumab and Cetuximab plus modified FOLFOX-6 in advanced untreated colorectal cancer", European Journal of Cancer, vol. 7, No. 2, 2009, p. 344.
Jakob et al., "Gastrointestinal Stromal Tumor of the Rectum: Results of Surgical and Multimodality Therapy in the Era of Imatinib", Annals of Surgical Oncology, vol. 20, No. 2, 2012, pp. 586-592.
Daud et al., "Phase I Study of Bosutinib, a Src/Abl Tyrosine Kinase Inhibitor, Administered to Patients with Advanced Solid Tumors", Clinical Cancer Research, vol. 18, No. 4, 2011, pp. 1092-1100.
Dulsat et al., "Saracatinib", Drugs of the Future, vol. 34, No. 2, 2009, pp. 106-114.
Golas et al., "SKI-606, a Src/Abl Inhibitor with In vivo Activity in Colon Tumor Xenograft Models", Cancer Research, vol. 65, No. 12, 2005, pp. 5358-5364.

\* cited by examiner

E

Late-phase activation

F    Rbpj target genes

Mouse
(Li et al., 2012)     Drosophila
                      (Krejčí et al. 2009)

98   3   55

Dab1 (dab)
Notch1 (Notch)
Hes1&5 (E(spl))

METHOD FOR DETERMINING PROGNOSIS OF CANCER

TECHNICAL FIELD

The present invention relates to a method, diagnostic composition, and kit for determining prognosis of cancer in a subject.

BACKGROUND ART

Cancer is the leading cause of death in most industrialized nations, and the direct cause of cancer death is often its metastasis to the vital organs. Colorectal cancer is the third most common cause of cancer mortality in Japan. Every year, ~100 new patients of colorectal cancer are diagnosed per population of 100,000, and the mortality rate is 30-40 per 100,000 patients; and it is still increasing.

Cancer treatment, such as chemotherapy and radiation has associated risks, and it is important to optimally select patients most likely to benefit. Although there are several studies on prognostic markers for colorectal cancer (Non-patent literatures 1-7), they are not enough to identify patients with good prognoses for whom risky therapy would not be necessary.

CITATION LIST

Non Patent Document

Non Patent Document 1: Science 314: 268-274 (2006)
Non Patent Document 2: Science 318: 1108-1113 (2007)
Non Patent Document 3: NEJM 344: 1196-1206 (2001)
Non Patent Document 4: Clin. Cancer Res. 17: 1535-1545 (2011)
Non Patent Document 5: J. Clin. Oncol. 29: 17-24 (2011)
Non Patent Document 6: J. Clin. Oncol. 29: 1261-1270 (2011)
Non Patent Document 7: J. Clin. Oncol. 29: 4620-4626 (2011)

Those references are herein incorporated by reference.

SUMMARY OF THE INVENTION

In studying the mechanism of cancer metastasis, we demonstrate that Notch receptor cleavage initiates DAB1-ABL activation and causes Tyr-phosphorylaton of TRIO. Further, we found that phosphorylation of TRIO at Y2681 correlates with poor prognosis of CRC patients (FIG. 6A), and TRIO(pY2681) signals not only in the primary CRC but also in its metastasis and in many other types of cancer including breast and lung cancers (FIG. 12 and Table 2). Based on those findings, we arrive at the present invention.

In one embodiment, the present invention provides a method for determining prognosis of cancer in a subject, which comprises the step of detecting phosphorylation of the tyrosine residue at position 2681 of TRIO in a sample obtained from the subject, wherein absence of phosphorylation indicates good prognosis of cancer.

In another embodiment, the present invention provides an antibody which specifically binds to TRIO (pY2681).

In another embodiment, the present invention provides a diagnostic composition for determining prognosis of cancer which comprises the antibody of the invention.

In another embodiment, the present invention provides a kit for determining prognosis of cancer which comprises the antibody of the invention.

In another embodiment, the present invention provides a pharmaceutical composition comprising an ABL inhibitor for treating colorectal cancer.

In another embodiment, the present invention provides a pharmaceutical composition comprising an ABL inhibitor for preventing metastasis of cancer.

Figure 1A:
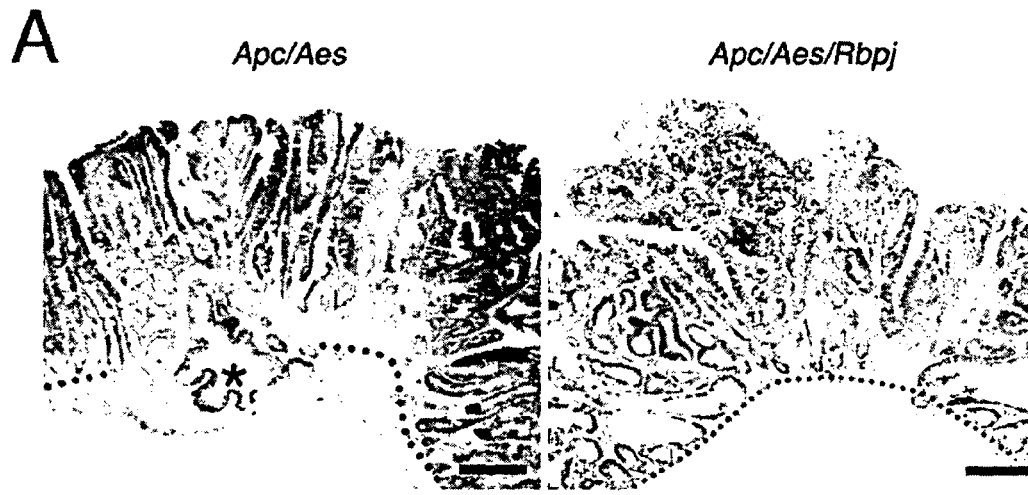
FIG. 1. Notch Signaling Activates Rho in CRC Cells to Stimulate Invasion (A and B) Rbpj gene knockout blocks invasion of intestinal tumors in Apc/Aes compound mutant mice. The depth of tumor invasion was analyzed histopathologically by H & E staining (A) and scored (B) in Apc/Aes double and Apc/Aes/Rbpj triple mutant mouse intestines. n=5 for each group. Dotted lines in (A) indicate the positions of muscularis mucosae. Asterisk in (A) shows a CRC gland invading into the submucosa. The depth of invasion in (B) is shown by abbreviations for intramucosal (Mu), and reaching to the submucosa (Sm), muscularis propria (MP) and serosa (Se). See Experimental Procedures for genotype abbreviation.

(C) Activation of Rho in the invading intestinal tumors of Apc/Aes mice. In a GTP-Rho pull-down assay, tissues of normal intestinal mucosa (N) and tumors (T) were analyzed from the Apc$^{+/\Delta 716}$ control (Apc), and Apc/Aes mutant mice. The amounts of the total Rho protein are also shown.

(D) Suppression of Rho activation by Aes. Colon26 TetON-Aes-Flag cells were plated onto culture dishes coated with recombinant extracellular domain of DLL4 (rDLL4) and induced with Flag-tagged Aes (Aes-F) by doxycycline. The cell layers were harvested 16 hours after being scratched, and analyzed for GTP-Rho.

(E and F) Inhibition of Rho or Rock suppresses Matrigel invasion and transendothelial migration (TEM) of CRC cells in culture. RKO human CRC cells were assayed for Matrigel invasion (E) or TEM (F), in the presence of Rho inhibitor C3T or Rock inhibitor Y-27632 at two doses, respectively.

(G and H) Time-course of Rho activation through Notch receptor activation in human CRC cells with EDTA. RKO cells were treated with 10 mM EDTA for 2 minutes and cultured in standard culture media for the indicated time and assayed for GTP-Rho.

(I) Activation of Rho via Notch receptor activation by its ligand. RKO cells were plated on dishes coated with rDLL4, and harvested at indicated time points for GTP-Rho pull-down assay.

(J) Reduced Rho activation by knockdown of three Notch receptor paralogs in CRC cells. RKO cells were transfected with mixtures (#1 and #2 for each paralog) of siRNA for Notch1, 2 and 3 (siNotch1/2/3). Non-silencing siRNA (Ns) and no-transfection (−) were used as controls. Forty-eight hours after transfection, the cells were treated with or without 10 mM EDTA and analyzed for GTP-Rho.

(K) Suppression of Rho activation by γ-secretase inhibition of Notch receptor activation. RKO cells were treated with 10 μM of DAPT for 12 h, treated with 10 mM EDTA, and subjected to Rho pull-down assays.

Scale bars, 100 μm. Data are presented as the mean with SD. *p<0.01 and #p<0.05. For GTP-Rho pull-down assay, the amounts of the total Rho protein were also determined. See also FIGS. 8A-8C.

FIG. 2. Both Rbpj-Dependent and -Independent Notch Signaling Is Critical for CRC Progression.

Early- (A-D) and late- (E-J) phase responses by Notch receptor activation.

(A) Notch and Rho are critical for attachment of CRC cells with endothelial cells (ECs). EGFP-expressing HCT116 cells were treated with or without C3T or DAPT for 2 hours, and plated onto a lung endothelial cell (LgEC) layer. Unbound HCT116 cells were washed off 15 minutes later, and numbers of cells remaining attached were counted by a fluorometer.

(B and C) Early-phase activation of Rho is independent of RBPJ. Stable clonal lines of HCT116 cells were established by transducing either two independent expression vectors for non-silencing control (Ns) or RBPJ-knockdown (shRBPJ) short hairpin RNA constructs (B). They were subjected to Rho pull-down assays after 2-min EDTA treatment (C).

(D) Attachment of CRC cells to ECs depends on γ-secretase activity even in the absence of RBPJ. RBPJ-knockdown or control cells described in (B) were treated with or without DAPT for 2 hours, and subjected to attachment assays as in (A).

(E) RBPJ is critical for late-phase activation of Rho. RBPJ-knockdown or control cells were treated with EDTA, and assayed at 6 or 12 hours for GTP-Rho.

(F) Rbpj target genes common to mouse and *Drosophila*. In mouse brain, 98 genes are regulated directly by Rbpj as determined by RNA-seq and chromatin immunoprecipitation (ChIP)-seq using anti-Rbpj Ab. In fruit fly, on the other hand, 55 genes are upregulated by Notch signaling, with their proximal regions bound by Su(H), the fly ortholog of mouse Rbpj. Shown are common 3 gene families commonly expressed between the two species through Rbpj; mouse and (fly) gene symbols.

(G) High-affinity binding motifs for the Notch transcription factor Su(H)/Rbpj/CBF1 found in the fly, mouse and human promoter regions for dab/Dab1/DAB1. The high- and low-affinity sequence motifs are shown by filled and open triangles, respectively. The primer pair for ChIP analysis (FIG. 2I, right) is indicated by a pair of horizontal triangles. TSS, transcription start site.

(H) Recombinant DLL4 (rDLL4) ligand induces DAB1 in cultured CRC cells. LS174T cells were incubated with or without 10 μM DAPT for 24 h, and plated on culture dishes pre-coated with or without rDLL4. Four-hours later, the DAB1 mRNA levels were quantified by quantitative (q) RT-PCR.

(I) RBPJ binding to the DAB1 promoter. ChIP of LS174T lysates with anti-Rbpj or anti-NICD Ab enriched the genomic promoter fragments for DAB1 gene as determined by qPCR.

(J) Dab1 is induced in Apc/Aes mouse CRC. Dab1 is stained with light grey whereas the nuclei are stained with dark grey in tumors of Apc and Apc/Aes mutant mice. Boxed areas are enlarged in the right panels. Same keys as in FIG. 1A. T, tumor. S, stroma.

Scale bars, 50 μm. Data are presented as the mean with SD. $*p<0.01$. See also FIG. 9.

Figure 1B:
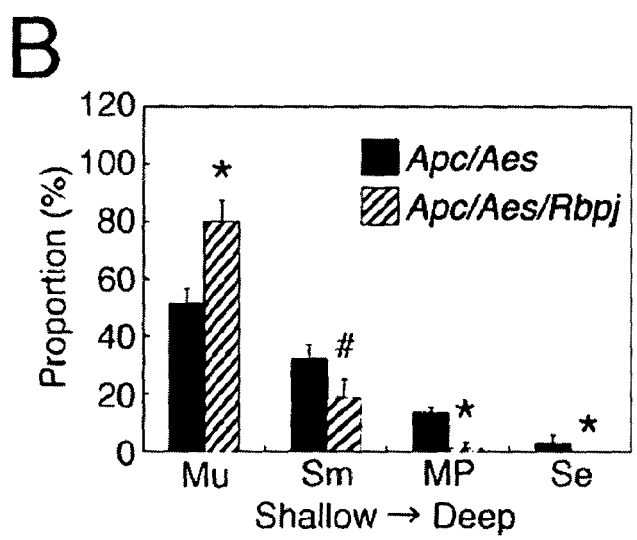
Figure 1C:
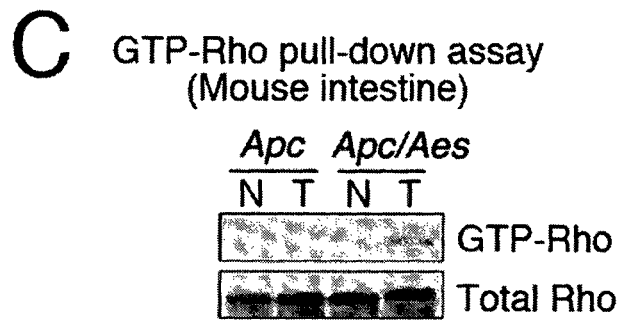

FIG. 3. DAB1 Stimulates CRC Invasion and Metastasis through Rho Activation (A and B) Dab1 is critical for progression of endogenous CRC. Intestinal epithelium-specific Dab1 null mutation was introduced to Apc/Aes double mutant mice to derive Apc/Aes/Dab1 triple mutant mice. Same methods and keys were employed as in FIGS. 1A and 1B.

(C, D and E) Knockdown of DAB1 inhibits metastasis of CRC transplants. DAB1-high LS174T cells were transduced with an expression vector encoding EGFP and an shRNA against DAB1 (shDAB1) (C). Two clonal lines were established and injected into the rectum of nude mice. Their lung metastases were evaluated under a fluorescent dissection microscope (D), and their numbers were scored (E).

(F, G and H) Expression of DAB1 stimulates CRC metastasis in vivo. DAB1-low RKO cells were transduced with an expression vectors for EGFP and DAB1 (F), and transplanted into the rectal mucosa of nude mice. Evaluation (G) and quantification (H) were performed as in (D) and (E), respectively.

(I) DAB1 is critical for both the early- and late-phase activation of Rho by Notch signaling. DAB1-knockdown or control clones were treated with 10 mM EDTA, and subjected to Rho pull-down assays at indicated times.

(J) Synergistic activation of Rho by Notch receptor cleavage and DAB1. DAB1-expressing RKO cells were treated or not with EDTA for 2 min, and subjected to Rho pull-down assays 5 minutes later.

(K) RBPJ-dependent induction of DAB1 after EDTA treatment. RBPJ-knockdown (shRBPJ; red) or control (Ns; black) HCT116 cells were treated with EDTA, and subjected to qRT-PCR assays for DAB1 mRNA at defined time.

Scale bars, 100 μm for (A) and 500 μm for (D) and (G). Data are presented as the mean with SD. $*p<0.01$ and $\#p<0.05$.

FIG. 4. Tyrosine Phosphorylations of DAB1 and of ABL Itself are Essential for Rho Activation and Invasion of CRC Cells (A and B) Imatinib suppresses invasion of endogenous CRC. The Apc/Aes compound mutant mice were treated with (red) or without (grey) 50 mg/kg/day imatinib for 9 weeks (n=5 each). Same methods and keys were employed as in FIGS. 1A and 1B.

(C) ABL knockdown in human CRC cells inhibits Matrigel invasion. RKO cells were transfected with two independent siRNA sets (#1 and #2) against ABL1 (siABL1), ABL2 (siABL2), or their combination, respectively. Forty-eight hours after transfection, expression of ABL1 and ABL2 was quantified by qRT-PCR (bottom). Simultaneously, cells were tested for Matrigel invasion (top).

(D) ABL knockdown reduces Rho activation triggered by Notch signaling. Two sets of combined knockdown were tested for inhibitory effects on Rho in RKO cells 5 minutes after EDTA treatment.

(E) ABL inhibitor imatinib blocks Matrigel invasion of CRC cells in a dose-dependent manner. RKO cells were treated with imatinib and tested for Matrigel invasion.

(F) Imatinib inhibits Rho activation induced by Notch receptor activation. RKO cells were treated with EDTA, either in the absence or presence of imatinib, and subjected to Rho pull-down assays 5 minutes later.

(G) DAB1 increases the Tyr-kinase activity of ABL in CRC cells. Lanes 1-3; HCT116 cells were expressed with equal amounts of Flag-tagged wild-type DAB1 (lane 2) or its 5YF mutant (lane 3), and their phospho-Tyr (pY) contents were determined by western blotting (WB) after immunoprecipitation (IP). Lanes 4-7; HCT116 cells were co-expressed with DAB1-Flag and HA-tagged wild-type (WT) ABL1B (ABL1B-HA). Note that the input amount of DAB1-Flag cDNA in lanes 6 and 7 was the same as that in lanes 2 and 3, respectively. Lanes 8-11; HCT116 cells were co-expressed with the same set of DAB1 cDNA in Lanes 4-7 and kinase-dead (KD) mutant of ABL1B.

Data are presented as the mean with SD. $*p<0.01$. See also FIG. 10.

FIG. 5. TRIO Is Tyr-phosphorylated in The Presence of ABL and DAB1, and Stimulates CRC Invasion (A) Schematic representation of TRIO domain structure (modified from (Bateman, J. and Vactor, D. V., 2001, J. Cell Sci. 114:1973-1980) and phosphorylatable Tyr residues.

Shown on top are domains of the wild-type human TRIO (TRIO WT) that contains 3097 aa. Rectangles show specific domains as indicated. Abbreviations: GEF, guanine nucleotide exchange factor domain; Ig, immunoglobulin-like domain; STK, serine-threonine kinase domain. Below the TRIO WT structure, the positions of Tyr (Y) to Phe (F) mutations are shown in red "F". Star in the Ig domain indicates G2699 whose missense mutation to Val is found in human lung cancer (see FIGS. 7F and 7G).

(B and C) TRIO knockdown inhibits Rho activation and Matrigel invasion induced by Notch signaling in CRC cells. HCT116 cells were transfected with two independent siRNA constructs against TRIO mRNA (siTRIO #1 or 2) After 48-h incubation, the cells were treated with or without EDTA and assayed for GTP-Rho (B) and Matrigel invasion (C).

(D) TRIO is Tyr-phosphorylated in the presence of ABL and DAB1 in CRC cells. HCT116 cells were transduced with or without an expression construct for T7-tagged TRIO (T7-TRIO), co-transduced with or without HA-tagged ABL1B (ABL1B-HA) and/or Flag-tagged DAB1 (DAB1-Flag). Same keys were employed as in FIG. 4G.

(E) C-terminal half of TRIO is phosphorylated by ABL. WT or YF mutants of T7-TRIO were expressed simultaneously with or without ABL1B-HA and DAB1-Flag, followed by western blot analysis of pYs.

(F) Y1990 and Y2681 in TRIO are phosphorylated in the presence of ABL and DAB1. Note that the pY level was dramatically reduced in Y1990F and Y2681F mutants (lanes 2 and 4) as in 4YFs (lane 6).

Data are presented as the mean with SD. $*p<0.01$.

FIG. 6. Phosphorylation of TRIO(Y2681) in Human CRC Is Correlated with Poor Prognosis.

(A) TRIO(pY2681) is correlated with poor prognosis of CRC patients. Primary CRC specimens from 102 patients were examined for TRIO(pY2681) by immunohistochemistry followed by Kaplan-Meier analysis. (Left) When patients at all stages were combined, 32 cases were negative (−), whereas 70 cases were positive (+) for TRIO(pY2681) immunostaining. (−) vs. (+), $p=0.01$ in chi-square test. (Center) For patients of stages I and II combined, the TRIO(pY2681)-negative group showed 100% survival for 5 years, with the TRIO(pY2681)-positive group showing ~20% death rate. (−) (n=23) vs. (+) (n=40), $p=0.04$ in chi-square test. (Right) Even only for stage II patients, the negative patients (n=13) had 100% survival compared with the positive patients (n=33) showing similar survival rate to those in stages I and II combined ($p=0.1$ in chi-square test).

(B) Stronger staining for TRIO(pY2681) in CRC cells (arrowheads) than in the adjacent normal mucosa (N) or lymphoid follicle (L). Boxed area is magnified in the inset.

(C, D and E) Staining for TRIO(pY2681) in CRC cells found in the invading stroma. Note that TRIO(Y2681) is highly phosphorylated in the budding (D) and dispersed (E) CRC cells (arrowheads).

Scale bars, 100 µm. See also FIG. 11.

FIG. 7. Phosphorylation of TRIO(Y2681) Stimulates RhoGEF Activity and Promotes Invasion of CRC Cells.

(A) Inverse correlation between nuclear AES and TRIO (pY2681) in human CRC. Shown are two representative sets of serial sections immunostained with anti-AES and anti-TRIO(pY2681) antibodies. Note that CRC glands expressing nuclear AES have few TRIO(pY2681) staining (arrows; top row), whereas TRIO(pY2681)-positive CRC glands lack AES expression (arrowheads; bottom row). Insets show higher magnification of boxed areas.

(B) Phosphorylation of Trio at Y2681 by loss of Aes in mouse intestinal tumors. Lysates of normal mucosa (N) and intestinal tumors (T) were analyzed for Trio(pY2681) by IP-WB. Total Trio blot is also shown (Trio).

(C) Stimulation of CRC invasion in Matrigel by TRIO (WT), but not TRIO(Y2681F). Clonal RKO TetON cell lines were constructed to express ABL1B-HA/DAB1-Flag simultaneously with T7-TRIO(WT) or T7-TRIO(Y2681F) in a doxycycline (Dox)-inducible manner, and assayed for protein expression and Matrigel invasion (D) Cell-free RhoGEF GTP exchange assay. TRIO(WT) protein was expressed, immunoprecipitated and mixed with recombinant RhoA and mant-GTP that emits fluorescence when it was bound with Rho. A representative result of three assays.

(E) TRIO(pY2681) is critical for the RhoGEF activity. T7-tagged TRIO (WT or Y2681F) was purified, and its RhoGEF activity for 10 min was determined. TRIO[ima]; TRIO protein purified from imatinib-treated HEK293T cells.

(F) TRIO(G2699V) stimulates RhoGEF activity. WT and G2699V mutant TRIO were purified and assayed for its RhoGEF activity as in (E).

(G) TRIO(G2699V) is more susceptible to Tyr-phosphorylation at Y2681. WT or G2699V T7-TRIO was expressed simultaneously with or without ABL1B-HA and DAB1-Flag. The pY content in TRIO was analyzed by IP-WB.

Scale bars, 10 µm. Data are presented as the mean with SD. $*p<0.01$ and $\#p<0.05$. See also FIG. 12.

FIG. 8. Notch Signaling Activates Rho in CRC Cells to Stimulate Invasion (addendum to FIG. 1.)

(A) Little effect of Rac inhibition on CRC invasion through Matrigel. RKO cells were treated with various concentrations of Rac inhibitor NSC27366 before and during the assay.

(B) Notch receptor activation by EDTA treatment. After 5 min treatment with 10 mM EDTA, Notch1 and NICD were precipitated by and detected with anti-Notch1 (C-term) antibody. Note that treatment with γ-secretase inhibitor DAPT inhibited the cleavage.

(C) Activation of Rho in response to EDTA treatment of Colon26 mouse CRC cells. Active Rho was pulled-down at the indicated time points of EDTA treatment. Total Rho was also analyzed.

Figure 9:
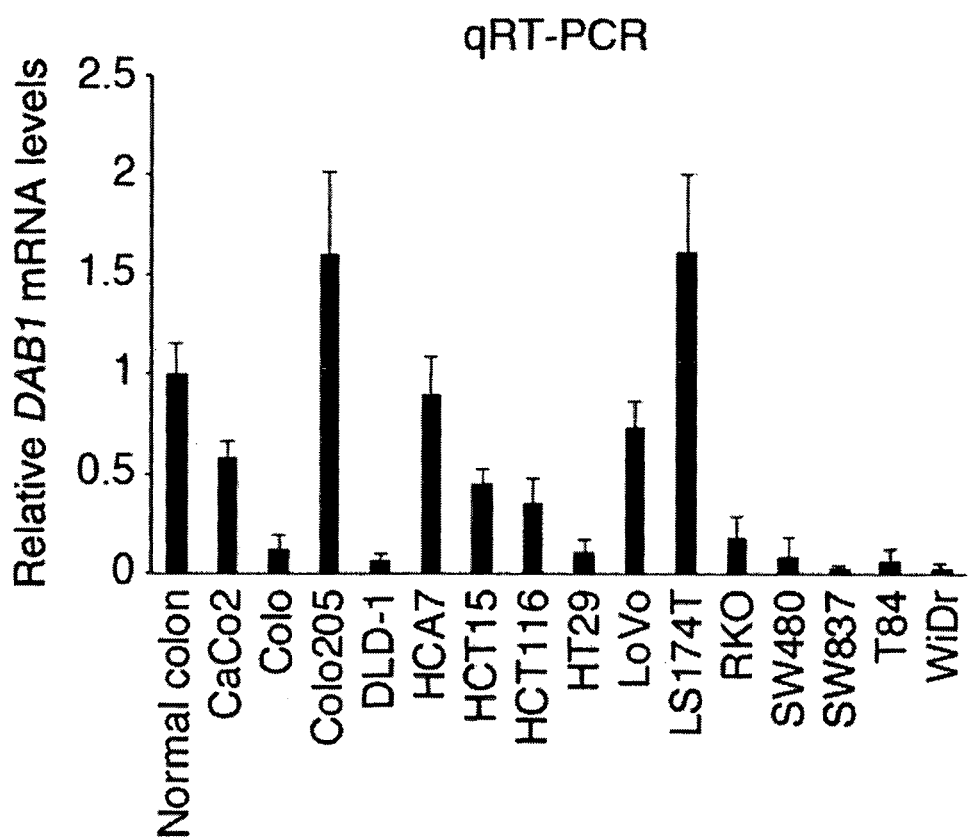

FIG. 9. Both Rbpj-Dependent and -Independent Notch Signaling Is Critical for CRC Progression (addendum to FIG. 2.)

Expression of DAB1 in human colonic cells. The amount of DAB1 mRNA was quantified by real-time PCR.

FIG. 10. Tyrosine Phosphorylations of Dab1 and of Abl Itself are Essential for Rho Activation and Invasion of CRC Cells (addendum to FIG. 4.)

(A) SRC inhibitor PP2 (at 10 µm) has only a minor effect on Matrigel invasion, whereas SRC-ABL dual inhibitor dasatinib (at 0.01 µm) shows a tight suppression of HCT116 cell invasion in Matrigel. $*p<0.01$, $\#p<0.04$.

(B) Dab 1 interacts with Abl in intestinal tumors in Apc/Aes mice. Immunoprecipitates from tumor lysates were resolved and detected by western blotting using anti-Abl and anti-Dab1 antibodies.

Figure 11:
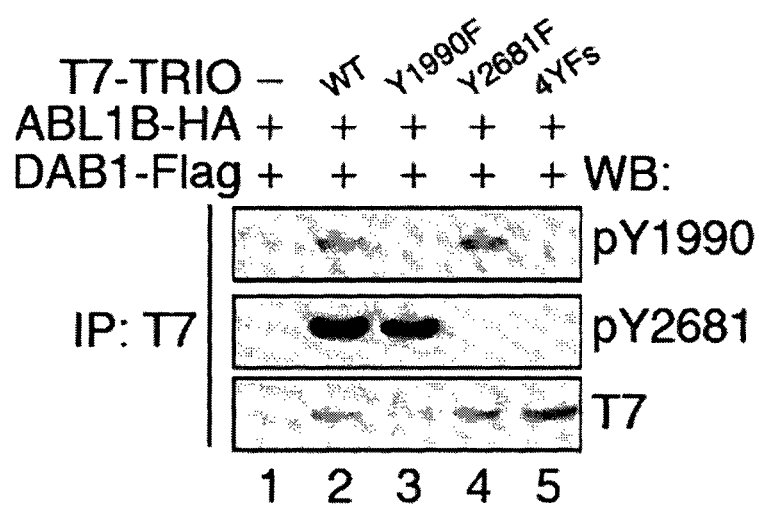
Figure 12A:
Figure 12B:
Figure 12C:
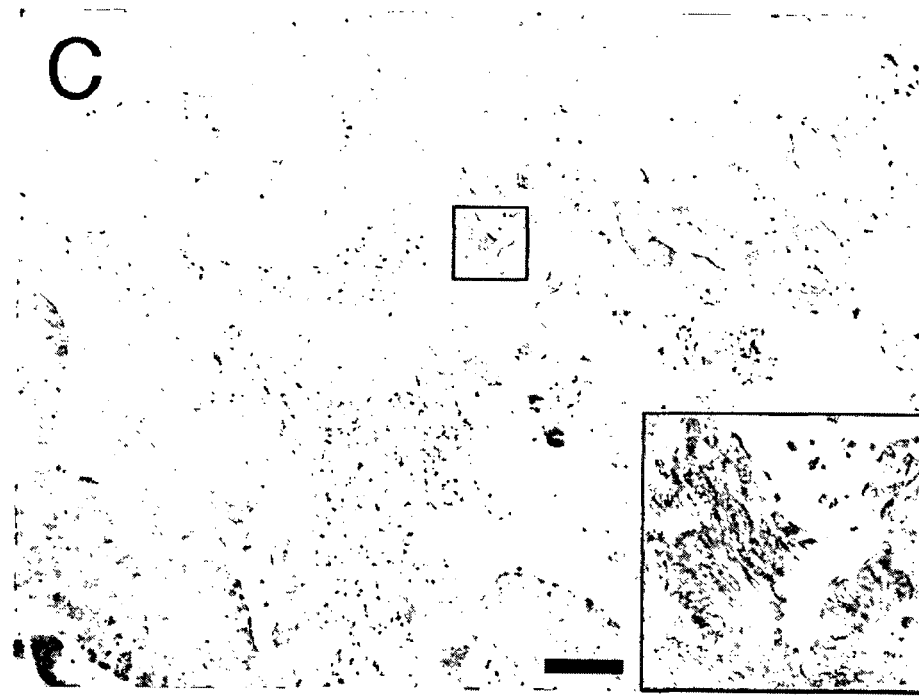
Figure 12D:
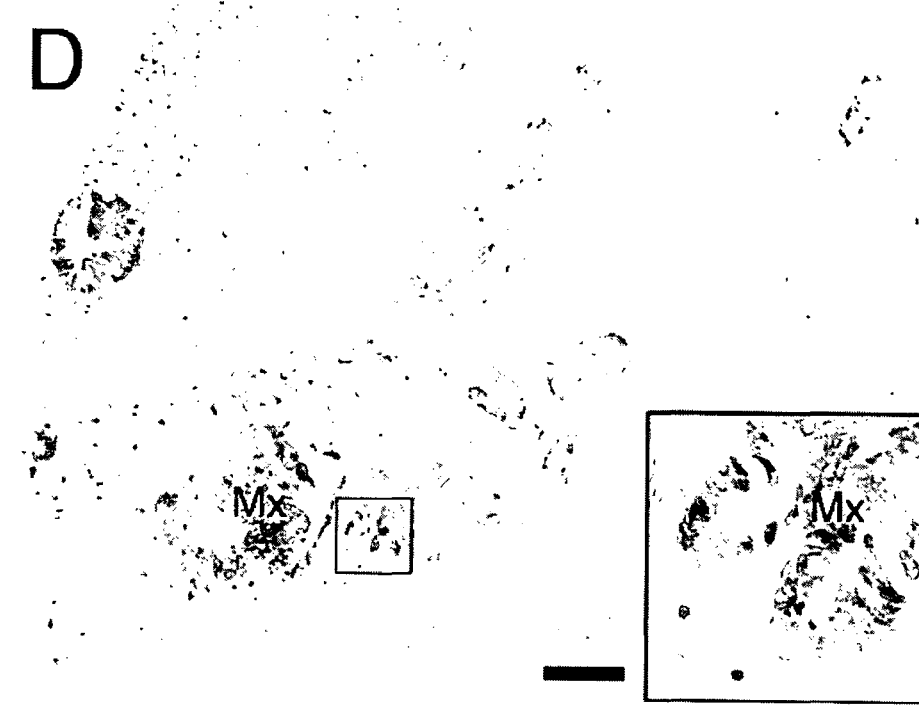
Figure 12E:
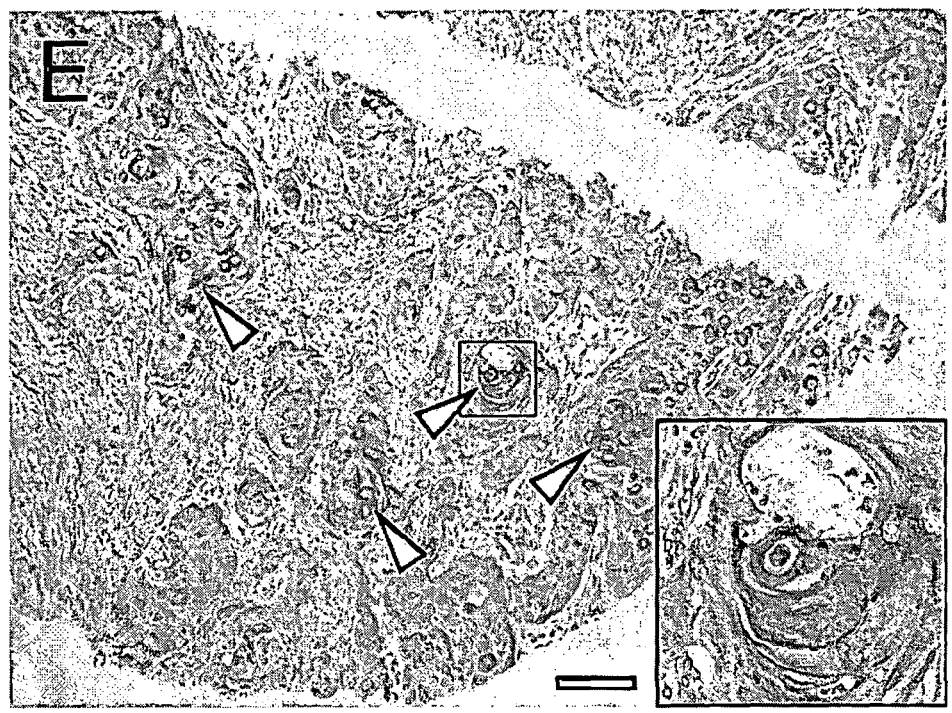
Figure 12F:
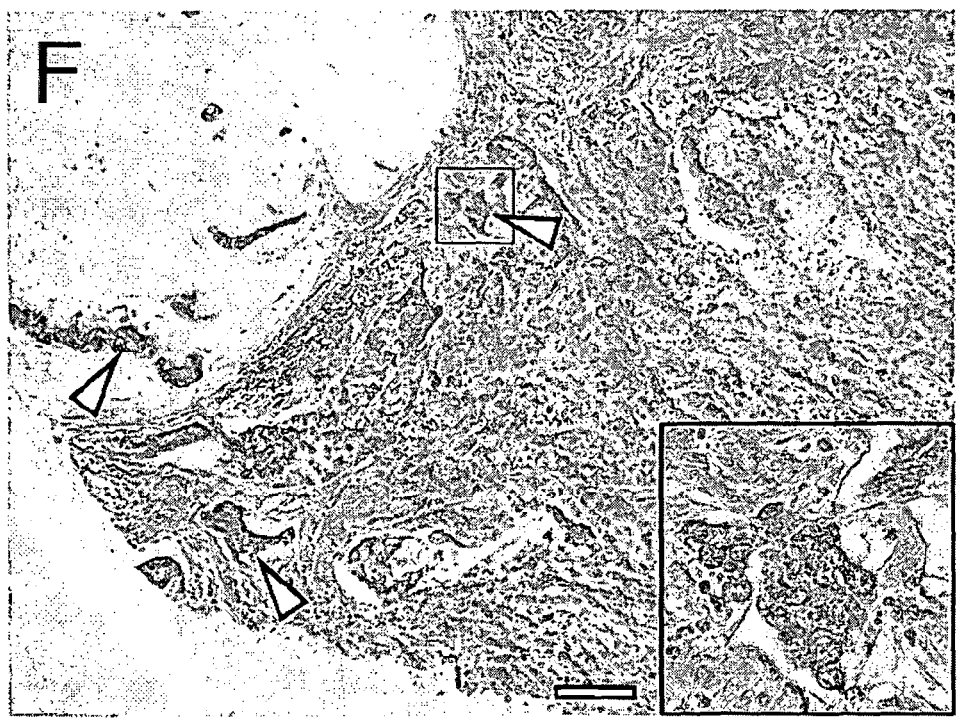

FIG. 11. Phosphorylation of Trio(Y2681) in Human CRC Is Correlated with Poor Prognosis (addendum to FIG. 6.)

Validation of specific antibodies for Tyr-phosphorylated TRIO. Antibodies were generated by immunizing rabbits with synthetic peptides containing pY1990 or pY2681, affinity-purified and used for immunocytochemistry. HEK 293T cells were transfected with expression plasmids for T7-tagged wild-type (WT), Y1990F or Y2681F TRIO simultaneously with those for ABL1B and DAB1. Note that anti-TRIO(pY1990) and anti-TRIO(pY2681) cannot recognize unphosphorylatable TRIO(Y1990F) and TRIO (Y2681F) mutants, respectively, as determined by immunofluorescence (data not shown) or western analyses. For western analysis, TRIO(4YFs) mutant was used as a negative control for Tyr-phosphorylation (lane 5).

FIG. 12. Phosphorylation of Trio(Y2681) Stimulates Rho-GEF Activity and Promotes Invasion of CRC Cells (addendum to FIG. 7.)

(A and B) Rectal adenocarcinoma (A) and its metastasis to the lung (B) immunostained with anti-TRIO(pY2681) antibody. Note that the metastatic cancer cells contained more abundant TRIO(pY2681) signals than its primary tumor.

(C and D) Colonic adenocarcinoma (C) and its metastasis to the ovary (D) immunostained with anti-TRIO(pY2681) antibody. Note that the metastatic cancer cells retain TRIO (pY2681) as in the primary tumor.

(E and F) TRIO(pY2681) immnohistochemistry of esophageal squamous cell carcinoma (E) and gastric adenocacinoma (F). Note cancer cells with strong TRIO(pY2681) staining (arrowheads).

Squared areas are enlarged in the insets. Mx, metastasis. Scale bars, 100 μm.

Figure 13A:
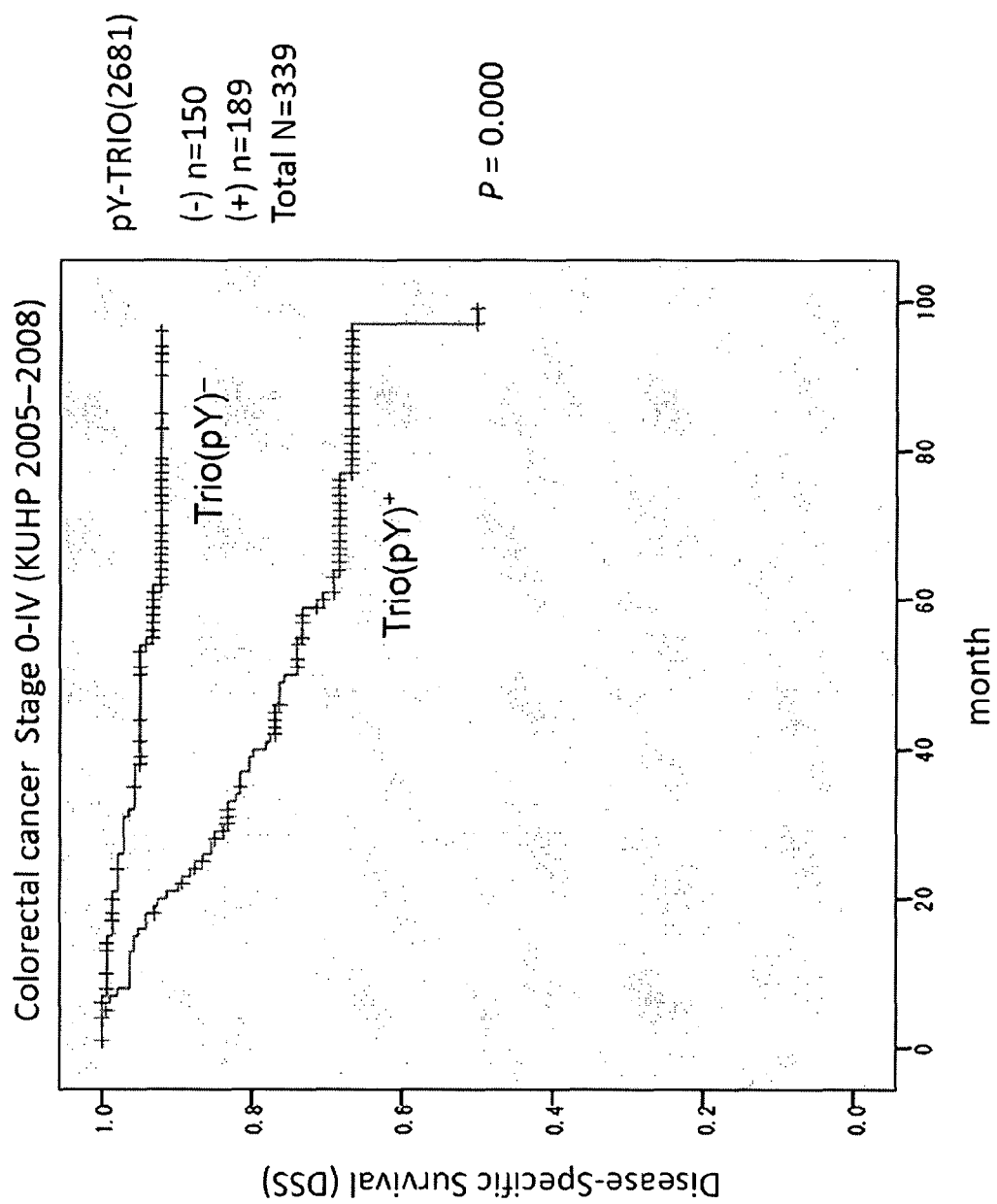
Figure 13B:
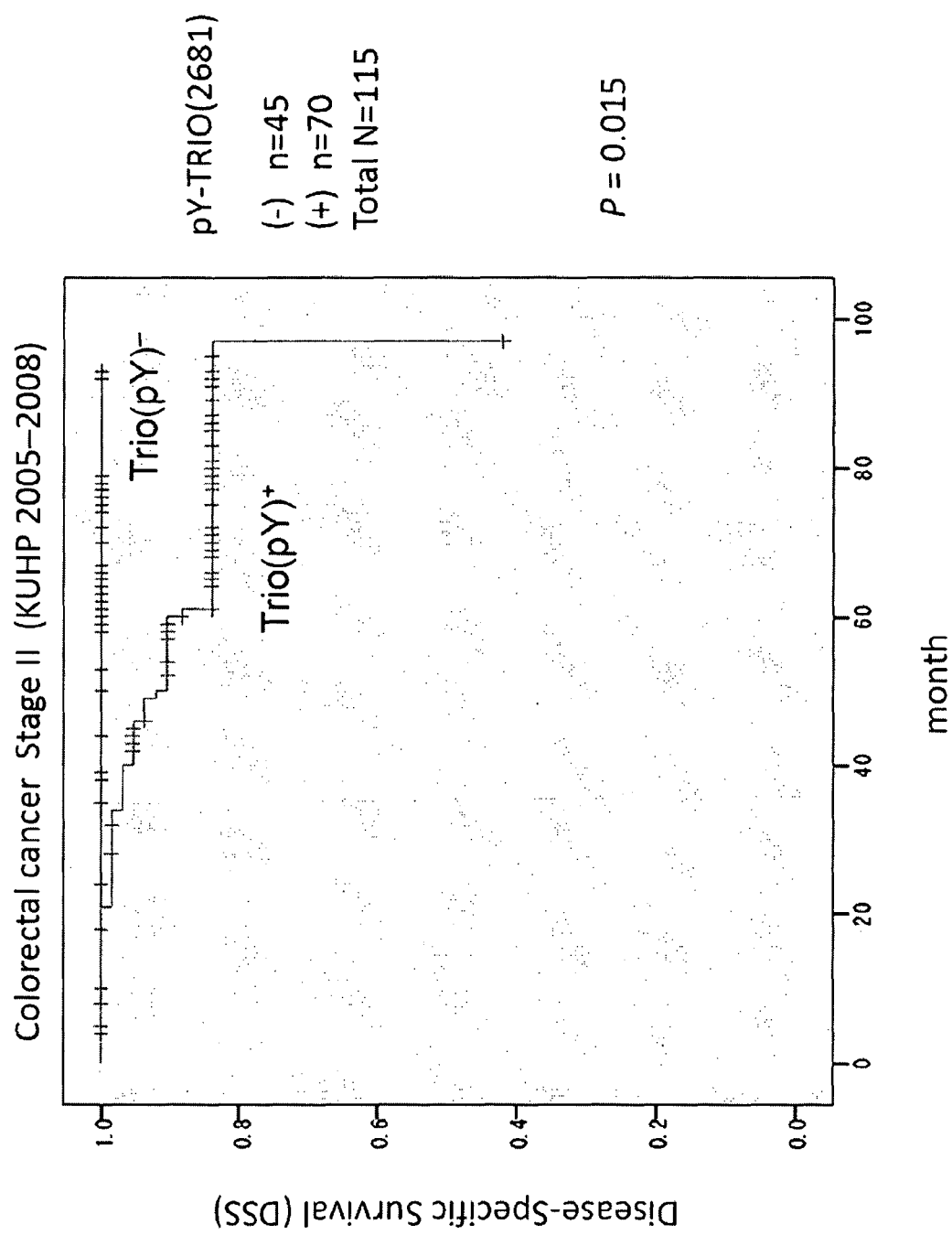
Figure 13C:
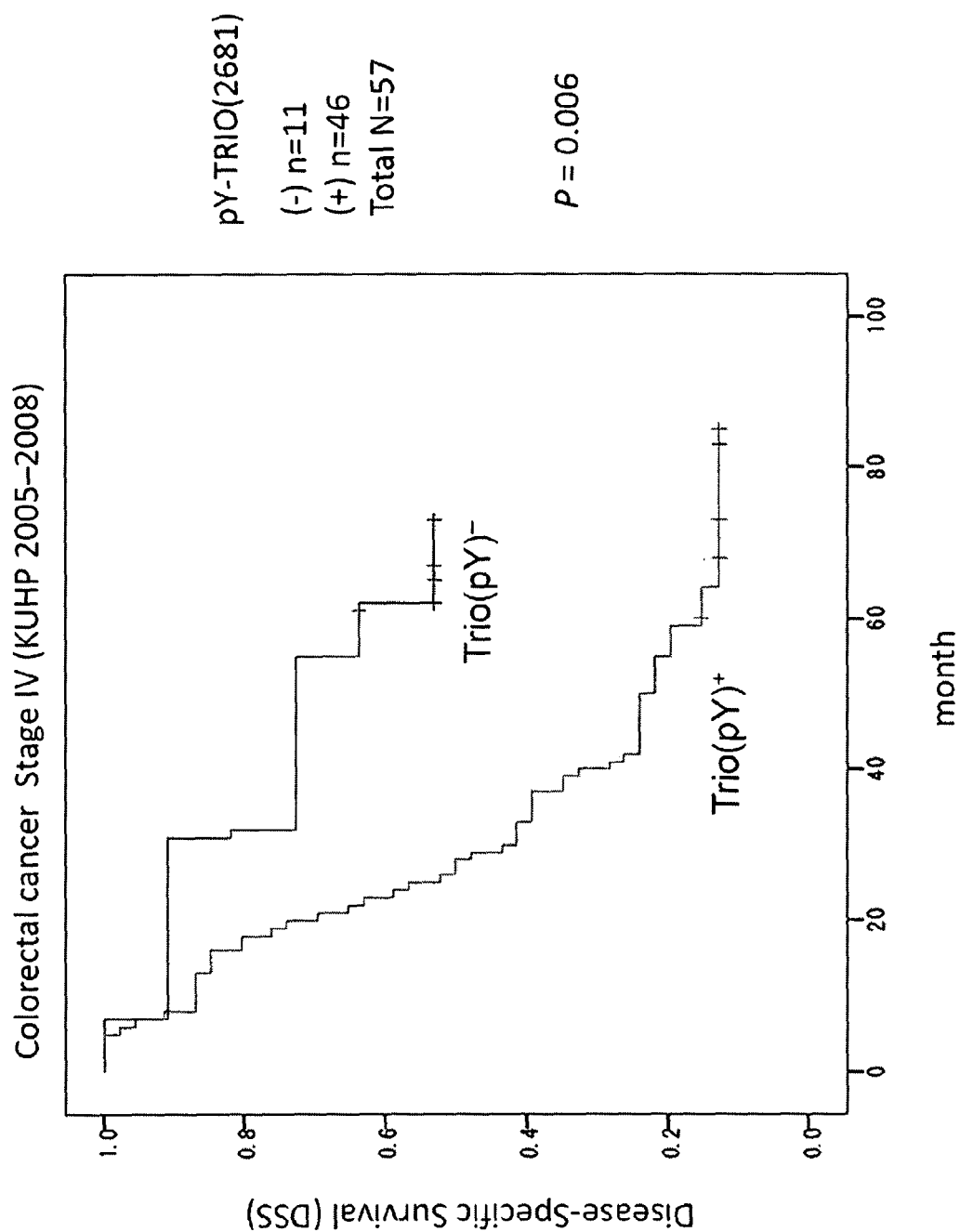

FIG. 13. Phosphorylation of Trio(Y2681) in human CRC is correlated with poorer prognosis.

Kaplan-Meier analysis of disease-specific survival regarding Trio(pY2681) of primary CRC specimens. (A) When patients of all stages were combined (n=339), 150 cases were Trio(pY2681)-low, whereas 189 were Trio (pY2681)-high (P<0.001 in log-rank test). (B) Stage II subpopulation (n=115) with the Trio(pY2681)-low (n=45) and -high (n=70) patients (P=0.015). (C) Stage IV subpopulation (n=57) with the Trio(pY2681)-low (n=11) and -high patients (n=46) (P=0.006).

Figure 14:
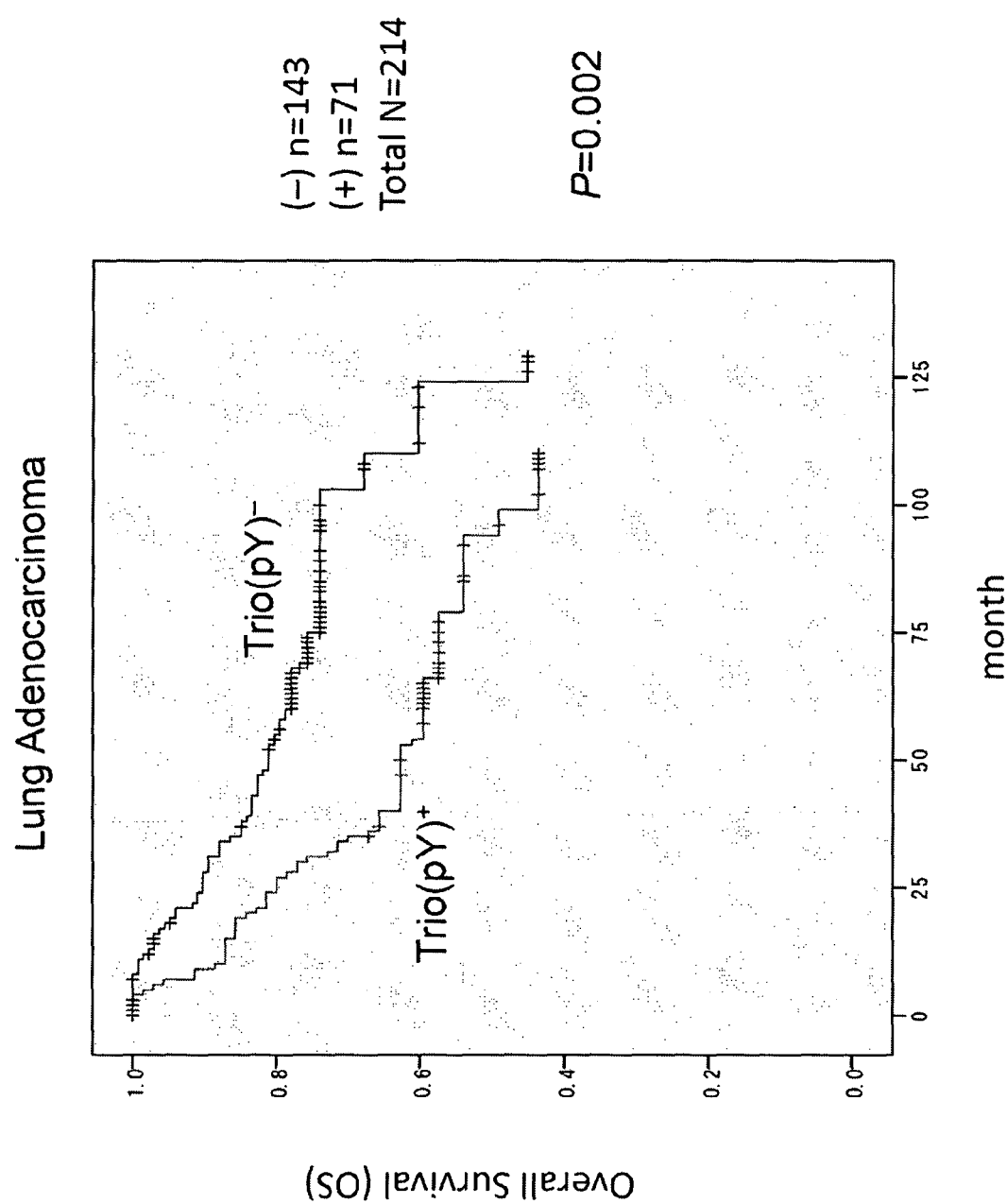

FIG. 14. Phosphorylation of Trio(Y2681) in human lung adenocarcinoma is correlated with poorer prognosis.

Kaplan-Meier analysis of disease-specific survival regarding Trio(pY2681) of primary lung adenocarcinoma specimens. Patients of all stages were combined (n=214), 143 cases were Trio(pY2681)-low, whereas 71 were Trio (pY2681)-high (P=0.002 in log-rank test).

Figure 15:
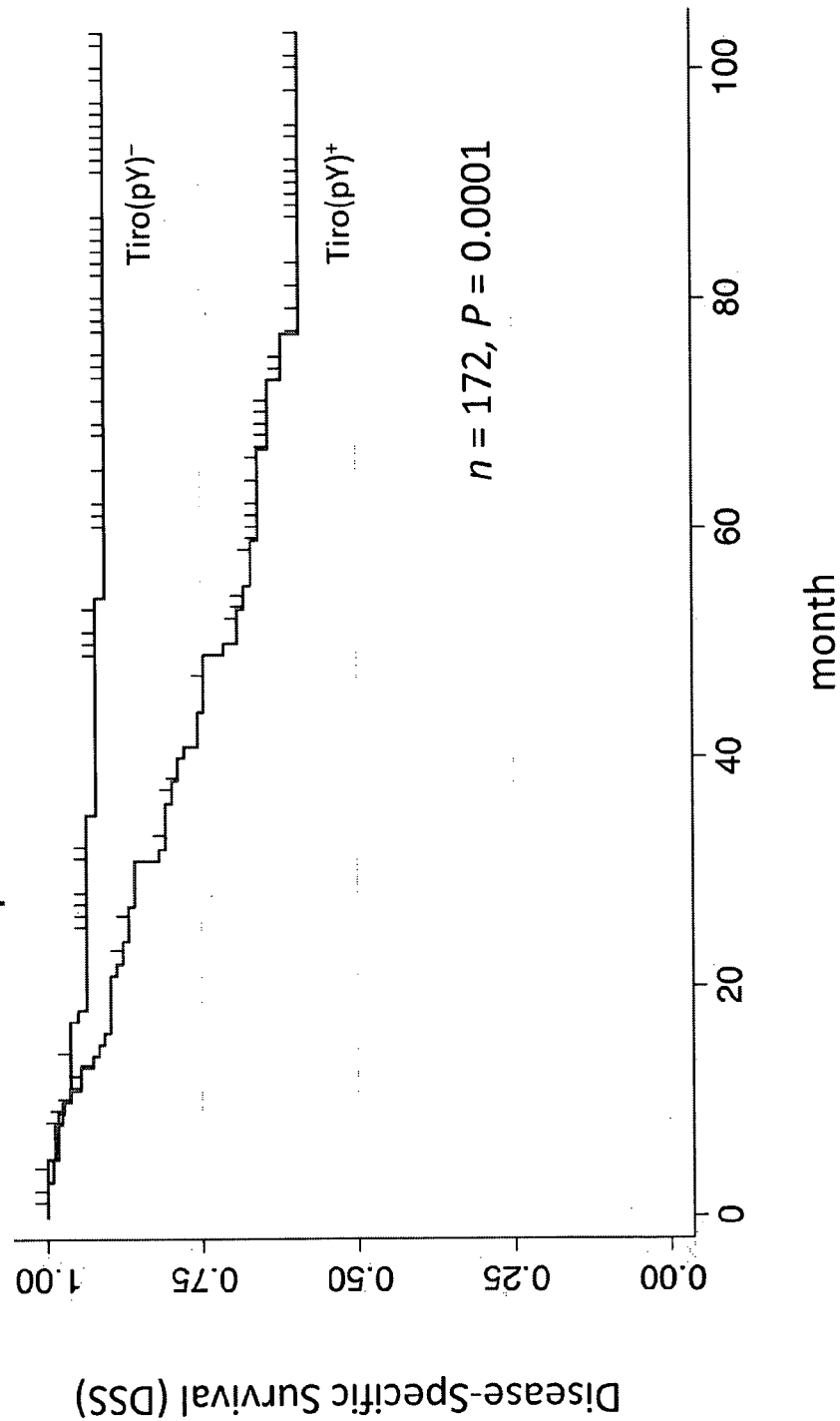

FIG. 15. Phosphorylation of Trio(Y2681) in human gastric cancer is correlated with poorer prognosis.

Kaplan-Meier analysis of disease-specific survival regarding Trio(pY2681) of primary gastric cancer specimens. Patients of stages I-III were combined (n=172), 82 cases were Trio(pY2681)-low, whereas 90 were Trio (pY2681)-high (P<0.001 in log-rank test).

Figure 16:
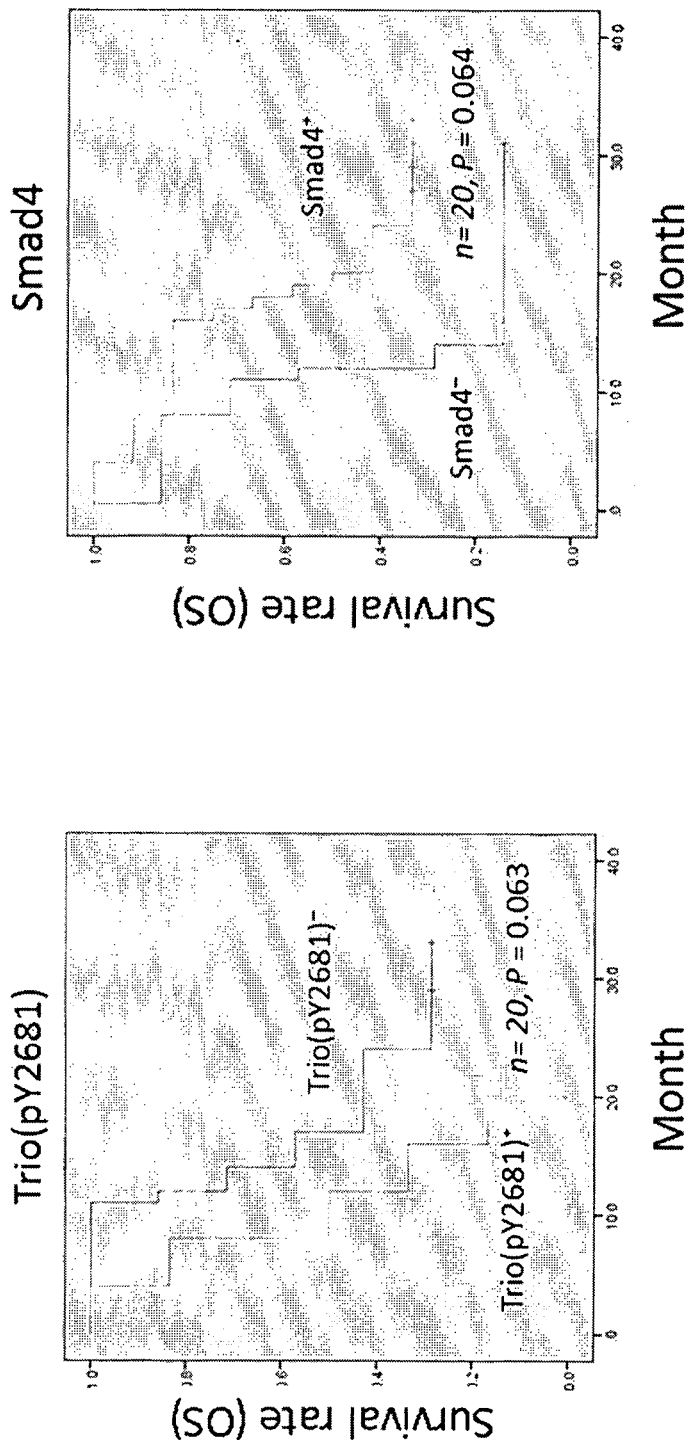

FIG. 16. Phosphorylation of Trio(Y2681) in human pancreatic cancer is correlated with poorer prognosis.

Preliminary Kaplan-Meier analysis of disease-specific survival regarding Trio(pY2681) and Smad4 of primary pancreatic cancer specimens. Patients of all stages were combined (n=20), (ID=0.063 and 0.064, respectively in log-rank test). Although both Trio(pY2681) and Smad4 showed almost the same P value here, they are statistically unrelated (P=0.51), suggesting independent each other.

DESCRIPTION OF EMBODIMENTS

As used herein, "TRIO" refers to all mammalian species of native TRIO, including human TRIO. The term "native TRIO" encompasses naturally occurring variants, e.g., alternatively spliced variants and allelic variants, of TRIO. As used herein, "a tyrosine residue at position 2681 of TRIO" refers to a tyrosine residue in a native TRIO corresponding to the tyrosine residue at position 2681 of SEQ ID NO: 1, which might not be at position 2681 in the native TRIO. As used herein, "TRIO (pY2681)" refers to TRIO of which tyrosine residue corresponding to the tyrosine residue at position 2681 of SEQ ID NO: 1 is phospholyated.

As used herein, prognosis of cancer includes prediction of duration of survival, duration of recurrence-free survival, duration of progression free survival, and likelihood of metastasis of a subject susceptible to or diagnosed with a cancer. In a preferred embodiment, prognosis of cancer is the duration of survival of a subject after surgical resection of the primary tumor.

As used herein, the term "subject" and "patient" includes, but not limited to, humans, monkeys, rabbits, chickens, and mice. In a preferred embodiment, a subject or patient is human. In a preferred embodiment, a subject or patient is a human cancer patient who has been received surgical resection of the primary tumor.

A "sample" encompasses a variety of sample types obtained from a subject and includes solid tissue samples or tissue cultures or cells derived therefrom. The sample can be obtained by a variety of procedures known in the art including, but not limited to surgical excision, aspiration or biopsy and may be fresh or frozen. The term "sample" also includes samples that have been manipulated in any way after their procurement, such as by treatment with reagents, solubilization, or enrichment for certain components, such as proteins or polynucleotides, or embedding in a semi-solid or solid matrix for sectioning purposes. In a preferred embodiment, the sample is obtained from a cancerous tissue of a subject upon surgery for tumor removal. The cancerous tissue may be derived from endoscopically resected polyps, or surgically resected primary or metastatic tumor. Preferably, the cancerous tissue is obtained from the primary tumor by surgical resection.

As shown in the following examples, phosphorylation of a tyrosine residue at position 2681 of TRIO is involved in metastasis of cancer, and TRIO(pY2681) is detected not only in colorectal cancer but also in other cancers (FIGS. 7 and 12 and Table 2). Therefore, the method of invention may be applied to various cancers. Examples of cancer include colorectal cancer including rectal cancer and colonic cancer; cancers of the following organs: adrenal gland, blood (lymphoma), bone, brain, breast, colorectum, endometrium, esophagus, gallbladder, kidney, larynx, liver, lung, oral cavity, ovary, pancreas, prostate, salivary gland, skin, small intestine (GIST), soft tissue, stomach, testis, thyroid, urinary bladder, uterine cervix; squamous cell cancer, uterine cancer, melanoma, multiple myeloma and B-cell lymphoma, head and neck cancer, glioblastoma, and associated metastases. In an embodiment, the cancer is selected from the group consisting of colorectal cancer, breast cancer, lung cancer, pancreas cancer, and gastric cancer. In a preferred embodiment, the cancer is selected from the group consisting of colorectal cancer, breast cancer, lung cancer, and gastric cancer. In a more preferred embodiment, the cancer is selected from the group consisting of colorectal cancer and gastric cancer. In a still more preferred embodiment, the cancer is colorectal cancer.

Colorectal cancer (also referred to as CRC) is staged based on how far the cancer has grown into the wall of the intestine, whether or not it has reached nearby structures, and whether or not it has spread to the lymph nodes or distant organs (Table 1).

TABLE 1

Colorectal cancer staging

| Stage | |
|---|---|
| 0 | Stage 0 (colon carcinoma in situ). Abnormal cells are shown in the mucosa of the colon wall. |
| I | Stage I colon cancer. Cancer has spread from the mucosa of the colon wall to the muscle layer. |
| II | Stage II colon cancer. In stage IIA, cancer has spread through the muscle layer of the colon wall to the serosa. In stage IIB, cancer has spread through the serosa but has not spread to nearby organs. In stage IIC, cancer has spread through the serosa to nearby organs. |
| III | Stage IIIA colon cancer. Cancer may have spread through the mucosa of the colon wall to the submucosa and muscle layer, and has spread to one to three nearby lymph nodes or tissues near the lymph nodes. OR, cancer has spread through the mucosa to the submucosa and four to six nearby lymph nodes. Stage IIIB colon cancer. Cancer has spread through the muscle layer of the colon wall to the serosa or has spread through the serosa but not to nearby organs; cancer has spread to one to three nearby lymph nodes or to tissues near the lymph nodes. OR, cancer has spread to the muscle layer or to the serosa, and to four to six nearby lymph nodes. OR, cancer has spread through the mucosa to the submucosa and may have spread to the muscle layer; cancer has spread to seven or more nearby lymph nodes. Stage IIIC colon cancer. Cancer has spread through the serosa of the colon wall but not to nearby organs; cancer has spread to four to six nearby lymph nodes. OR, cancer has spread through the muscle layer to the serosa or has spread through the serosa but not to nearby organs; cancer has spread to seven or more nearby lymph nodes. OR, cancer has spread through the serosa to nearby organs and to one or more nearby lymph nodes or to tissues near the lymph nodes. |
| IV | Stage IV colon cancer. The cancer has spread through the blood and lymph nodes to other parts of the body, such as the lung, liver, abdominal wall, or ovary. |

(http://www.cancer.gov/cancertopics/pdq/treatment/colon/Patient/page2)

Figure 6A:
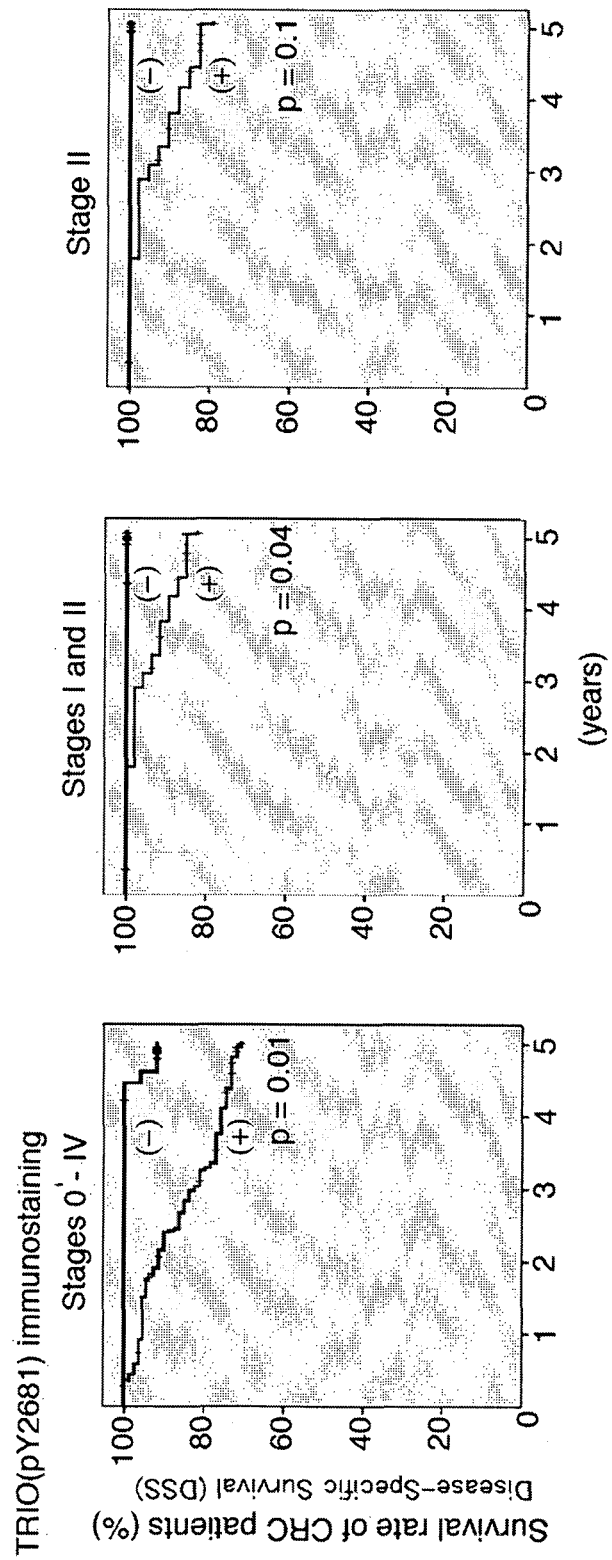

As shown in the following examples, two subpopulations in stages I and II CRC patients can be further distinguished using the TRIO(pY2681) staining. Namely, those who had negative pY2681 showed 100% cure (no recurrence at all), whereas those with pY2681-positive primary tumors had ~20% recurrence in 5 years (FIG. 6A, FIG. 13B). Therefore, for the stage I and II patients who are not subjected to adjuvant chemotherapy according to the current guideline, the method of invention can identify patients who should be considered for further treatment with adjuvant therapy after surgery. For the stage III and IV patients, the method of invention can help stratify higher-risk subpopulations. Accordingly, the method of the invention may be used for a subject diagnosed with colorectal cancer at any of the stages I-IV, and particularly useful for a subject diagnosed with colorectal cancer at stage I or II, in particular stage II.

Phosphorylation of a tyrosine residue at position 2681 of TRIO may be detected by an anti-TRIO (pY2681) antibody. As used herein, "an anti-TRIO (pY2681) antibody" refers to an antibody which specifically binds to TRIO (pY2681). The antibody "which specifically binds to TRIO (pY2681)" refers to an antibody which binds to TRIO (pY2681) but does not bind to TRIO of which tyrosine residue at position 2681 is not phospholyrated (also referred to as "unphosphorylated TRIO(Y2681)" herein).

Phosphorylation can be detected by a number of methods which are well-known in the art, including immunohistochemistry assays, ELISA (Enzyme-linked, immunosorbent assay), and Western analysis. In a preferred embodiment, immunohistochemistry assays are used.

In one embodiment, a sample is a tissue sample obtained from surgical excision and fixed and embedded in paraffin or the like. The tissue sample may be fixed by conventional methodology ("Manual of Histological Staining Method of the Armed Forces Institute of Pathology," 3rd edition (1960) Lee G. Luna, H T (ASCP) Editor, The Blakston Division McGraw-Hill Book Company, New York; The Armed Forces Institute of Pathology Advanced Laboratory Methods in Histology and Pathology (1994) Ulreka V. Mikel, Editor, Armed Forces Institute of Pathology, American Registry of Pathology, Washington, D.C.; those references are herein incorporated by reference). For example, neutral buffered formalin, Bouin's or paraformaldehyde, may be used to fix a sample. Generally, the sample is first fixed and is then dehydrated through an ascending series of alcohols, infiltrated and embedded with paraffin or other sectioning media so that the tissue sample may be sectioned. Alternatively, one may section the frozen tissue and fix the sections obtained. In a preferred embodiment, a tissue sample may be embedded and processed in paraffin by conventional methodology. Once the tissue sample is embedded, the sample may be sectioned by a microtome or the like. Sections may range from about three microns to about five microns in thickness. Once sectioned, the sections may be attached to slides by several standard methods. Examples of slide adhesives include, but are not limited to, silane, gelatin, poly-L-lysine and the like. For example, the paraffin embedded sections may be attached to positively charged slides and/or slides coated with poly-L-lysine. If paraffin has been used as the embedding material, the tissue sections are generally deparaffinized and rehydrated to water. The tissue sections may be deparaffinized by several conventional standard methodologies. For example, xylenes and a gradually descending series of alcohols may be used. Alternatively, commercially available deparaffinizing nonorganic agents such as Hemo-De7 (CMS, Houston, Tex.) may be used.

Following a blocking step, the tissue section is exposed to an antibody which specifically binds to the target antigen (i.e., TRIO (pY2861)) for a sufficient period of time and under suitable conditions such that the antibody binds to the target antigen in the tissue sample. Appropriate conditions for achieving this can be determined by routine experimentation. The antibody may be labeled with a radioisotope, a fluorescent label, or an enzymatic label to visualize the target antigen without further antibody interaction. Alternatively, the antibody which specifically binds to the target antigen may be used as a primary antibody together with a labeled secondary antibody which binds to the primary antibody.

To detect Trio(pY2681) in cancer tissues, one can use cellular ELISA (CELISA), a modification of ELISA. CELISAs can be performed in 96-well plates, which permits high throughput results. The bottom of each well is attached with a tissue section that is then permeabilized with a detergent. The sample is then incubated in the well with the Trio (pY2681) antibody. After unbound antibody is washed off, the bound primary antibody is then bound with enzyme-linked secondary antibody, and the unbound antibody is washed off again. Then the amount of the specifically bound secondary antibody will be measured by the activity of coupled enzyme reactions. (e.g., Schlosser, M. et al., J. Immunol. Methods, 140: 101-109, 1991, herein incorporated by reference).

Phosphorylation of a tyrosine residue at position 2681 of TRIO in a sample obtained from a subject may be detected by comparing the sample with a suitable control sample. Exemplary control samples include a negative control sample (e.g. a non-cancerous tissue from a heath subject or a cancerous tissue from a cancer patient with good prognosis) or a positive control sample (e.g. a cancerous tissue from a cancer patient with poor prognosis).

As used herein, absence of phosphorylation refers to insignificant level of phosphorylation compared to that observed for a negative control sample. To the contrary, presence of phosphorylation refers to significant level of phosphorylation compared to that observed for a negative control sample. In the present invention, absence of phosphorylation indicates good prognosis of cancer. In one embodiment, absence of phosphorylation indicates likelihood of long survival after surgical resection of the primary tumor. In another embodiment, absence of phosphorylation indicates likelihood of no recurrence within 5 years after surgical resection of the primary tumor. In another embodiment, absence of phosphorylation indicates unnecessity of adjuvant therapy after surgical resection of the primary tumor. In another embodiment, presence of phosphorylation indicates necessity of adjuvant therapy after surgical resection of the primary tumor. Adjuvant therapy includes chemotherapy, radiation therapy, hormone therapy, targeted therapy, and biological therapy, and is preferably chemotherapy. In a preferred embodiment, adjuvant therapy is chemotherapy with an ABL kinase inhibitor such as imatinib in view of prevention of metastasis.

In a different embodiment, the prevent invention provides an ABL kinase inhibitor such as imatinib for use in the adjuvant therapy after surgical resection of the primary tumor in a subject. Preferably, the subject is a human patient with colorectal cancer.

As used herein, the term "antibody" includes polyclonal antibodies, monoclonal antibodies, and antibody fragments. The "antibody" may be those raised in rodents (mouse, rat, hamster, guinea pig, rabbit etc.), birds (chicken, quail, turkey etc.), large mammals (goat, sheep, donkey etc.), human antibodies, chimeric antibodies, and humanized antibodies.

An anti-TRIO (pY2681) antibody may be prepared using a peptide derived from TRIO having an amino acid sequence comprising the phosphorylated tyrosine at position 2681 as an immunizing antigen. The length of the peptide is not specifically limited and may be 5-30 amino acids, preferably 5-20 amino acids, more preferably 8-15 amino acids. In a preferred embodiment, the peptide has the amino acid sequence of SEQ ID NO: 9.

A polyclonal antibody may be prepared by a conventional method, for example, a method described in "Antibodies: A Laboratory Manual", Lane, H. D. et al. eds., Cold Spring Harbor Laboratory Press, New York, 1989, herein incorporated by reference. In brief, a polyclonal antibody may be prepared by immunizing an animal, such as mouse, rat, hamster, guinea pig, rabbit, chicken, quail, turkey, goat, sheep, or donkey, with the peptide derived from TRIO as described above.

A monoclonal antibody may be prepared by the hybridoma method first described by Kohler et al., Nature 256:495 (1975), herein incorporated by reference, or may be made by recombinant DNA methods (U.S. Pat. No. 4,816,567, herein incorporated by reference). A monoclonal antibody may also be isolated from phage antibody libraries using the techniques described in Clarkson et al., Nature 352:624-628 (1991), herein incorporated by reference, or Marks et al., J. Mol. Biol. 222:581-597 (1991), herein incorporated by reference, for example.

A chimeric antibody is an antibody comprising the variable regions on the heavy chain and the light chain of an antibody from a mammal other than human, such as mouse, and the constant regions on the heavy chain and light chain from a human antibody. A chimeric antibody may be obtained by ligating the DNA coding for the variable region of the mouse antibody and the DNA coding for the constant region of the human antibody, and incorporating into an expression vector, and introducing a host for antibody production.

A humanized antibody is composed of the complementarity determining region (CDR) of an antibody derived a non-human mammal, and the framework region (FR) and the constant region derived from a human antibody. A humanized antibody may be obtained by grafting the CDR of an antibody from a non-human mammal, such as a mouse, into the CDR of a human antibody. Specifically, a DNA sequence designed to ligate a mouse antibody CDR to the FR of human antibody is synthesized by PCR using as primers several oligonucleotides constructed to have overlapping portions at the ends of both CDR and FR. The obtained DNA is ligated with the DNA coding for the constant region of the human antibody, then incorporated into an expression vector, which is introduced into and expressed by a host to obtain the antibody (European Patent EP 239400; International Publication WO 96/02576; those references are herein incorporated by reference).

A method for obtaining a human antibody is also known. For instance, a human lymphocyte is sensitized with a desired antigen or a cell expressing the desired antigen in vitro, and sensitized lymphocyte is fused with a human myeloma cell, for instance U266, to obtain the desired human antibody capable of binding to the antigen (Japanese Patent Publication No. H1-59878, herein incorporated by reference). Alternatively, a transgenic animal having the entirety of the repertoire of human antibody genes may be immunized with the desired antigen to obtain the desired human antibody (International Publication WO 93/12227, WO 92/03918, WO 94/02602, WO 94/25585, WO 96/34096 and WO 96/33735; those references are herein incorporated by reference). Further, a technique where a human antibody is selected by panning from a human antibody library is also known. For instance, the variable region of the human antibody is expressed as a single chain antibody (scFv) on the surface of a phage by the phage display method, and a phage binding to the antigen is selected. The gene of the selected phage is analyzed to determine the sequence of the DNA coding for the variable region of the human antibody binding to the antigen. Once the DNA sequence of the scFv binding to the antigen is determined, a suitable expression vector containing the sequence can be prepared to produce the human antibody. These methods are well known, and described in International Publication WO 92/01047, WO 92/20791, WO 93/06213, WO 93/11236, WO 93/19172, WO 95/01438 and WO 95/15388 (those references are herein incorporated by reference).

Examples of an antibody fragment include Fab, F(ab')2, Fv, Fab/c having one Fab and a full Fc, and a single chain Fv (scFv) where the Fv of the H chain and the L chain are linked via an appropriate linker. An antibody fragment may be obtained by treating an antibody with an enzyme such as papain or pepsin. Alternatively, a gene encoding such an antibody fragment is constructed and introduced into an expression vector, and the antibody fragment is expressed in a suitable host cell (see, for example, Co, M. S. et al., J.

Immunol. (1994) 152, 2968-2976, Better, M. & Horwitz, A. H. Methods in Enzymology (1989) 178, 476-496, Academic Press, Inc., Plueckthun, A. & Skerra, A. Methods in Enzymology (1989) 178, 476-496, Academic Press, Inc., Lamoyi, E., Methods in Enzymology (1989) 121, 652-663, Rousseaux, J. et al., Methods in Enzymology (1989) 121, 663-669, Bird, R. E. et al., TIBTECH (1991) 9, 132-137; those references are herein incorporated by reference).

As used herein, the "antibody" includes an antibody modified with any of a variety of molecules such as radioisotopes, fluorescent labels, and enzymatic labels. Examples of radioisotopes includes $^{35}S$, $^{14}C$, $^{125}I$, $^{3}H$, and $^{131}I$. Examples of enzymatic labels include luciferase, luciferin, peroxidase such as horseradish peroxidase, alkaline phosphatase, β-galactosidase, and the like. Examples of fluorescent labels include Texas Red, rhodamine, fluorescein, dansyl, Lissamine, umbelliferone, phycoerytherin, phycocyanin, or commercially available fluorophores such SPECTRUM ORANGE7 and SPECTRUM GREEN7 and/or derivatives of any one or more of the above, or fluorescent dyes as AlexaFluor, Cy3, Cy5. The antibody can be labeled with a radioisotope, a fluorescent label or an enzymatic label using conventional methodologies (Current Protocols in Immunology, Volumes 1 and 2, Coligen et al, Ed. Wiley-Interscience, New York, N.Y., Pubs. (1991); Methods in Enzym., 73:147-166 (1981); those references are herein incorporated by reference).

In an embodiment, the present invention provides a diagnostic composition for determining prognosis of cancer which comprises the antibody of the present invention. The diagnostic composition of the invention is used in accordance with the method of the invention. The diagnostic composition may be provided with instructions for use in accordance with the method of the invention described herein.

In an embodiment, the present invention provides a kit for determining prognosis of cancer which comprises the antibody of the present invention. The kit of the invention is used in accordance with the method of the invention. The kit may be the one used for immunohistochemistry assays, Western analysis, or ELISA. The kit may comprise other optional components such as one or more buffers (e.g., block buffer, wash buffer, substrate buffer, etc), other reagents such as substrate (e.g., chromogen) which is chemically altered by an enzymatic label, and control samples (positive and/or negative controls) as well as instructions for use in accordance with the method of the invention described herein.

In an embodiment, the present invention provides a pharmaceutical composition comprising an ABL inhibitor for treating colorectal cancer.

In another embodiment, the present invention provides a pharmaceutical composition comprising an ABL inhibitor for preventing metastasis of cancer. The metastasis includes micrometastasis. Examples of cancer include colorectal cancer including rectal cancer and colonic cancer; cancers of the following organs: adrenal gland, blood (lymphoma), bone, brain, breast, colorectum, endometrium, esophagus, gallbladder, kidney, larynx, liver, lung, oral cavity, ovary, pancreas, prostate, salivary gland, skin, small intestine (GIST), soft tissue, stomach, testis, thyroid, urinary bladder, uterine cervix; squamous cell cancer, uterine cancer, melanoma, multiple myeloma and B-cell lymphoma, head and neck cancer, glioblastoma, and associated metastases. In an embodiment, the cancer is selected from the group consisting of colorectal cancer, breast cancer, lung cancer, pancreas cancer, and gastric cancer. In a preferred embodiment, the cancer is selected from the group consisting of colorectal cancer, breast cancer, lung cancer, and gastric cancer. In a more preferred embodiment, the cancer is selected from the group consisting of colorectal cancer and gastric cancer. In a still more preferred embodiment, the cancer is colorectal cancer.

Examples of an ABL inhibitor includes imatinib (4-(4-methylpiperazin-1-ylmethyl)-N-[4-methyl-3-(4-(pyridin-3-yl)-pyrimidin-2-ylamino-)phenyl]-benzamide), nilotinib (4-methyl-N-[3-(4-methyl-1H-imidazol-1-yl)-5-(trifluoromethyl)phenyl]-3-[(4-pyridin-3-ylpyrimidin-2-yl)amino] benzamide), ponatinib (3-(2-imidazo[1,2-b]pyridazin-3-yl-ethynyl)-4-methyl-N-[4-[(4-methylpiperazin-1-yl)methyl]-3-(trifluoromethyl)phenyl]benzamide), dasatinib (N-(2-chloro-6-methylphenyl)-2-[[6-[4-(2-hydroxyethyl)-1-piperazinyl]-2-methyl-4-pyrimidinyl]amino]-5-thiazole carboxamide monohydrate), bosutinib (4-[(2,4-dichloro-5-methoxyphenyl)amino]-6-methoxy-7-[3-(4-methylpiperazin-1-yl)propoxy]quinoline-3-carbonitrile), and befatinib (INNO-406) (N-[3-([5,5'-bipyrimidin]-2-ylamino)-4-methylphenyl]-4-[[(3S)-3-(dimethylamino)-1-pyrrolidinyl] methyl]-3-(trifluoromethyl)benzamide) or a pharmaceutically acceptable salt thereof. In a preferred embodiment, the ABL inhibitor is imatinib or a pharmaceutically acceptable salt thereof.

Pharmaceutical acceptable salts of imatinib includes pharmaceutical acceptable acid addition salts, like for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxybenzoic acid, 2-acetoxy-benzoic acid, salicylic acid, or 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. In a preferred embodiment, a monomethanesulfonic acid addition salt of imatinib, i.e., imatinib mesylate, disclosed in WO99/03854 (herein incorporated by reference) is used.

The ABL inhibitor is administered to a subject in a daily dose depending on species, age, individual condition, mode of administration, and the clinical picture in question. For example, the ABL inhibitor may be administered to a human adult in a daily dose of about 100-1000 mg, preferably about 200-600 mg, more preferably about 400-600, especially about 400 mg.

In a preferred embodiment, the pharmaceutical composition of the invention is used in an adjuvant therapy. Preferably, the adjuvant therapy is treatment after surgical resection of the primary tumor in the patient.

The present invention provides a method for treating colorectal cancer, which comprises administering an ABL inhibitor to a patient in need thereof, and a method for preventing metastasis of cancer, which comprises administering an ABL inhibitor to a patient in need thereof. Also, the present invention provides use of an ABL inhibitor for the manufacture of a medicament for treating colorectal cancer, and use of an ABL inhibitor for the manufacture of a medicament for preventing metastasis of cancer. The method and use of the invention can be carried out as explained for the pharmaceutical composition of the invention.

The invention is further described in the following examples, none of which are intended to limit the scope of the invention.

EXAMPLES

Experimental Procedures

Mutant Mice, CRC Cells and Intra-Rectum Transplantation $Apc^{+/\Delta716}$ mutant mice were generated and maintained as described previously {Oshima, 1995}. $Apc^{+/\Delta716}Aes^{Floxed/Floxed}vCre^{ERT2}$ (abbreviated as Apc/Aes) mice were constructed as reported to knockout Aes in $Apc^{+/\Delta716}$ mice by virtue of $Cre^{ERT2}$ whose expression is driven by intestinal epithelium-specific villin promoter {Sonoshita, 2011}. Rbpj floxed allele was constructed as reported {Han, 2002}, obtained from RIKEN BRC, and crossed with Apc/Aes mice to derive $Apc^{+/\Delta716}Aes^{Floxed/Floxed}Rbpj^{Floxed/Floxed}vCre^{ERT2}$ (Apc/Aes/Rbpj) mice. Dab1 floxed allele was constructed (Imai et al., in preparation) and crossed with Apc/Aes mice to obtain $Apc^{+/\Delta716}Aes^{Floxed/Floxed}Dab1^{Floxed/Floxed}vCre^{ERT2}$ (Apc/Aes/Dab1) mice. Tumor histopathology in compound mutant mice was analyzed at 12 weeks of age. For ABL inhibition, Apc/Aes mice were treated with imatinib (LC Laboratories) for 9 weeks since they were 3 weeks of age at a dose of 50 mg/kg/day (i.p.) that suppresses the tumorigenic activity of BCR-ABL-transformed cell lines in transplanted mice {Buchdinger, 2001}. Total of ~100 tumors with diameters larger than 2 mm from 5 mice were scored for each mutant genotype. CRC cell lines were obtained from ATCC. Upon transplantation into the rectal smooth muscle, CRC cells formed a visible primary tumor within a week. Six weeks later, mice were euthanized and examined for metastatic foci under a fluorescent microscope (Leica). All animal experiments were conducted according to the protocol approved by the Animal Care and Use Committee of Kyoto University.

Active Rho Pull-Down Assay

GTP-Rho was pulled-down and detected by using Rho activation assay kit (Thermo) according to the manufacturers' protocol. Briefly, tissues or CRC cells were lysed with lysis buffer, and GTP-Rho in the lysates was pulled-down using Rhotekin and detected by anti-Rho antibody in western analysis.

rDLL4 Experiments

Recombinant DLL4 (rDLL4) (R&D) was resuspended with PBS. For scratch and GTP-Rho pull-down assays, 1 µg was put into 6-well culture plate to coat its surface with rDLL4 at 0.1 µg/cm². For q-RT-PCR assays, the plate surface was coated with rDLL4 at 0.1-1 µg/cm². After overnight incubation at 4-degree, the plates were washed once with PBS and plated with CRC cells. For expression analysis of HES1 and DAB1, cells were lysed and mRNA was extracted after four hours.

Scratch Assay

Colon26 TetON-Aes-Flag cells were constructed as described so that expression of Flag-tagged Aes is induced by doxycycline (Sonoshita et al., 2011). The cells were plated on culture dishes coated with rDLL4, cultured until they became subconfluent, and treated with doxycycline for 16 h prior to scratch. Four hours after making scratches, cells were harvested pull-down assays for active Rho.

Matrigel Invasion and TEM Assays

Cultured cancer cells were treated with C3T (Cytoskeleton), Y-27632 (Wako), NSC27366, PP2 (Calbiochem), imatinib or dasatinib (LC Laboratories) for 16 h prior to Matrigel invasion and TEM assays. Matrigel invasion assays were performed as previously described using Matrigel (BD) {Sonoshita, 2011}. For TEM assay, human umbilical vein endothelial cell (HUVEC) was seeded in the upper chamber of Transwell (Corning). One day (24 h) later, EGFP-labeled CRC cells were plated onto the layer of HUVEC. After 24 h, CRC cells migrated to the lower side of the membrane were counted under a fluorescent microscope.

Notch Receptor Activation by EDTA

Cultured CRC cells were washed with PBS, treated with 10 mM EDTA in PBS for 2 minutes, and incubated again in culture media. This treatment has been shown to activate Notch receptors by promoting shedding of the Notch ectodomain (Rand et al., 2000; Tiyanont et al., 2011). After incubation for defined period, cells were lysed and cleaved Notch and GTP-Rho was detected. DAPT (Calbiochem) were applied to cultured CRC cells to inhibit its γ-secretase activity.

Knockdown Experiments siRNA oligos (QIAGEN) were transfected into CRC cells by using HiperFect transfection reagent (QIAGEN). Forty-eight hours after the transfection, cells were subjected to Matrigel invasion, GTP-Rho pull-down, or gene expression assays. For transplantation experiments, knockdown sequences for DAB1 (shDAB1#1: AAGGATTAAGTAG-GATGTCAA (SEQ ID NO: 2), shDAB1#2: CCGGTA-CAAAGCCAAATTGAT (SEQ ID NO: 3)) were inserted into pLB vectors (Addgene), respectively. Then lentiviral particles were prepared and infected into LS174T cells to derive constitutive DAB1-knockdown EGFP⁺ cells. Stable knockdown clones for RBPJ were derived as described previously (Sonoshita et al., 2011).

Attachment Assay

Attachment assay was performed according to the established protocol {Reymond, 2012}. Briefly, human lung endothelial cells were plated onto collagen-coated dish. After they reached confluent to form a layer, EGFP-labeled CRC cells were plated onto it. Fifteen minutes later, floating cells were washed with PBS, and the numbers of CRC cells adhering to the endothelial layer were counted under a fluorescent microscope.

Dab/Dab1/DAB1 Promoter Analysis

Fly dab, mouse Dab1, and human DAB1 promoters were extracted from UCSC Genome Browser Database (http://genome.ucsc.edu/cgi-bin/hgGateway). The plot analysis for high- and low-affinity Su(H)/Rbpj binding sites was performed by a text-based search as described previously (Nellesen et al., 1999).

Quantitative PCR (q-PCR)

TaqMan primers/probes for quantification of HES1, DAB1, ABL1, and ABL2 mRNAs were purchased from ABI. ChIP analyses were performed by using CRC cells and anti-Rbpj (Institute of Immunology) and anti-NICD (Cell Signaling Technology) antibodies according to published protocol (Kakizaki et al., 2010). Precipitated fragments of genomic DNA were tested for enrichment of promoter regions of HES1 gene by SYBR green (ABI) using hHES1ChIP.F (CGTGTCTCCTCCTCCCATT) (SEQ ID NO: 4) and hHES1ChIP.R (GAACGGCTCGTGT-GAAACTT) (SEQ ID NO: 5) primers that sandwich high affinity binding sequence of Rbpj. Similarly, enrichment of DAB1 promoter fragments was quantified by hDAB1ChIP.F2 (CAAGCTCTGTGCTTGTCTCA) (SEQ ID NO: 6) and hDAB1ChIP.R2 (GTAGCTGTGTGGTCT-TATCA) (SEQ ID NO: 7) primers.

Immunohistochemistry

Frozen and paraffin-embedded tissues of mice were prepared according to the standard procedures. Human CRC tissues (n=102, Stages 0-4) had been resected from patients in Kyoto University Hospital who had undergone operations with informed consents in between 2005 and 2007, with the protocol approved by the Ethics Committee of Kyoto University. Human Tissue Array slides (SuperBioChips) were also enrolled in this study for analysis of metastatic CRC and other types of cancer. Sections were stained with H & E or incubated with the primary antibodies specific for DAB1 (SIGMA), Aes (Sonoshita et al., 2011), TRIO(pY1990) or TRIO(pY2681) (prepared as described below) followed by Alexa Fluor (Molecular Probes)-conjugated or biotinylated secondary antibodies (Vector Laboratories).

Overexpression Experiments

Wild-type DAB1 cDNA (provided by Kamon Sanada, The University of Tokyo, Japan) was inserted into pMX-IRES-EGFP (provided by Toshio Kitamura, The University of Tokyo, Japan). Retroviral particles were prepared and infected into RKO cells, and EGFP+ cells were confirmed to express DAB1 stably.

Immunoprecipitation-Western Analysis

ABL1B cDNA was prepared from cDNA pool of human colon and tagged with hemaglutinin (HA) sequence to construct ABL1B-HA. The wild-type cDNA was mutagenized by QuikChange Lightning Multi Site-Directed Mutagenesis Kit (Agilent) to derive kinase-dead ABL1B (K290R)-HA mutant. These ABL1B constructs were placed into pEFBosneo expression vector (provided by Shigekazu Nagata, Kyoto University, Japan). DAB1-Flag cDNA was inserted into pcDNA3 (Invitrogen). TRIO cDNA (provided by Anne Debant, CRBM-CNRS, France) was tagged with T7 sequence and inserted into pCX expression vector carrying CAG promoter and rabbit β-globin poly(A) (provided by Masaru Okabe, Osaka University, Japan). NICD-Myc expression vector was provided by Tasuku Honjo, Kyoto University, Japan. These expression vectors were transfected into CRC or HEK293T cells using Lipofectamine LTX (Invitrogen). Sixteen hours post-transfection, the cells were lysed in lysis buffer (10 mM Tris-Cl, 1 mM EDTA, 150 mM NaCl and 1% NP-40). The supernatants were mixed with agarose conjugated with anti-HA, Flag, T7, or Myc antibodies (MBL). The beads were washed with the lysis buffer and then boiled in SDS sample buffer. The eluted proteins were separated by SDS-PAGE, transferred to nylon membrane and probed with antibodies against HA, Flag, Myc, phosphotyrosine (pY; Cell Signaling Technology), TRIO (pY2681), or T7 (Novagen). Endogenous Notch1 was immunoprecipitated by anti-Notch1 (Santa Cruz), and probed with the same antibody in western analyses. Endogenous Dab1 or Trio was immunoprecipitated by anti-Dab1 or anti-Trio antibodies (Santa Cruz), respectively, from lysates of the mouse gut.

TRIO Mutagenesis

Possible phosphorylation sites of Tyr in TRIO were predicted by NetPhos2.0 online software (http://www.cbs.d-tu.dk/services/NetPhos/) (Blom et al., 1999). Among the candidates, we mutagenized 18 Tyr with high probabilities into Phe by QuikChange Lightning Multi Site-Directed Mutagenesis Kit (Agilent) to create YF unphosphorylatable mutants. Each point mutation of TRIO in human cancers was introduced to wild-type TRIO by using the same kit. Construct integrities were confirmed by DNA sequencing and western analyses.

Preparation of Anti-TRIO(pY1990) and Anti-TRIO (pY2681) Antibodies

Peptides 1985-1994 VRDLG(pY)VVEG (SEQ ID NO: 8) and 2676-2686 NPNYI (pY)DVPPE (SEQ ID NO: 9) were synthesized and injected into rabbits at Scrum (Japan). After validation of its titer by ELISA, each antibody was affinity-purified using the immobilized antigen and the unphosphorylated corresponding peptide.

Immunocytochemistry

HCT116 cells were transfected with expression plasmids for T7-TRIO, ABL1BHA and DAB1-Flag, and seeded onto chamber slides (Thermo). After incubation for 16 h, the cells were fixed for 5 min with 3.7% formaldehyde in PBS, permeabilized with PBS containing 0.1% TritonX-100 for min, and then blocked in 5% normal donkey serum for 30 min. Then the specimens were incubated with primary antibodies specific for T7 and Tyr-phosphorylated TRIO for 1 h at room temperature. After three washes with PBS, they were incubated with Alexa Fluor-conjugated secondary antibodies. The specimens were washed with PBS, and then mounted on glass slides with VECTASHIELD Mounting Medium with DAPI (Vector Labs).

Construction of RKO TetON Cells

RKO cells were transfected with pCMV-Tet3G (Clontech), and G418 (Nacalai)-resistant clones were established. The "parent" TetON clones were chosen by its ability to induce luciferase in response to doxycycline (Clontech). Then such parent lines were transfected with pTRE3G vector (Clontech) encoding cDNAs for ABL1B-HA and DAB1-Flag to establish double-inducible "RKO TetON ABL1B-HA/DAB1-Flag" cells. Subsequently, they were transfected with pTRE3G carrying T7-TRIO cDNA to construct triple-inducible "RKO TetON T7-TRIO/ABL1B-HA/DAB1-Flag" cells.

RhoGEF Exchange Assay In Vitro

First, we transfected HEK293T cells with an expression plasmid for T7-TRIO (either WT, Y2681F or G2699V), and pulled-down each TRIO protein from cell lysates using agarose conjugated with anti-T7 antibody (MBL). Then we mixed the TRIO fraction with recombinant RhoA in the presence of mant-GTP (Cytoskeleton) that emits stronger fluorescence when bound to Rho small GTPases (Rossman et al., 2002).

Data Analysis

Data were analyzed by Student's t or chi-square tests using SPSS (IBM) and are presented as mean±SD. P values<0.05 were considered significant.

Results

Rbpj is Critical for Invasion of Intestinal Tumors

As we have shown recently, invading and intravasating tumors develop in the intestines of compound mutant mice for Apc and Aes genes (abbreviated as Apc/Aes mice) (FIG. 1A, left) {Sonoshita, 2011}. While Aes inhibits Notch-dependent transcription in CRC, it remains unclear how Notch signaling derepressed by loss of Aes stimulates progression of intestinal tumors. As the transcription factor of Notch signaling, Rbpj (aka CBF1 in human) plays a pivotal role in target gene expression {Artavanis-Tsakonas, 1999}. To determine the roles of Rbpj in progression of endogenous CRC, we introduced an Rbpj null mutation {Han, 2002} into the Apc/Aes double mutant mice in an intestinal epithelium-specific manner, and constructed Apc/Aes/Rbpj triple mutant mice. Interestingly, knocking out Rbpj dramatically reduced tumor invasion and intravasation without affecting their size or number (FIGS. 1A and B, and data not shown), suggesting that Rbpj plays a key role in CRC progression through transcription of the Notch target genes.

Notch Signaling Stimulates Invasion and Transendothelial Migration (TEM) of CRC Cells Through Rho Activation We next investigated effectors downstream of Notch signaling that promoted CRC invasion and intravasation. The Rho family small GTPases are well-characterized regulators of cell motility that appear essential for cancer metastasis {Hall, 1998; Hall, 2009; Weinberg, 2007}. Therefore, we first studied the activation status of Rho, Rac and Cdc42 in benign (Apc) and invasive (Apc/Aes) colon tumors using pull-down assays. We found that the level of the GTP-bound (i.e., active-form) Rho was significantly increased in the lysates of intestinal tumors from the Apc/Aes compound mutant mice (FIG. 1C), although that of Rac or Cdc42 was not affected or below the detection limit (data not shown).

Figure 1D:
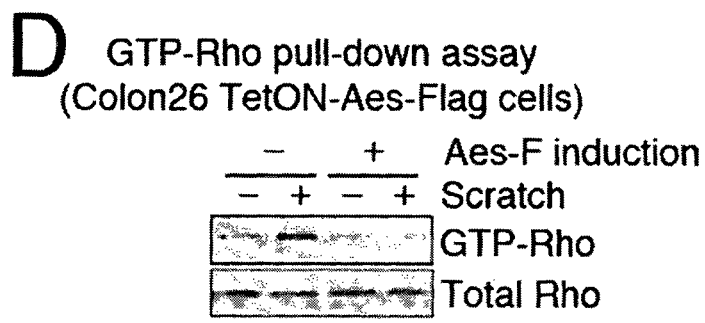
Figure 1E:
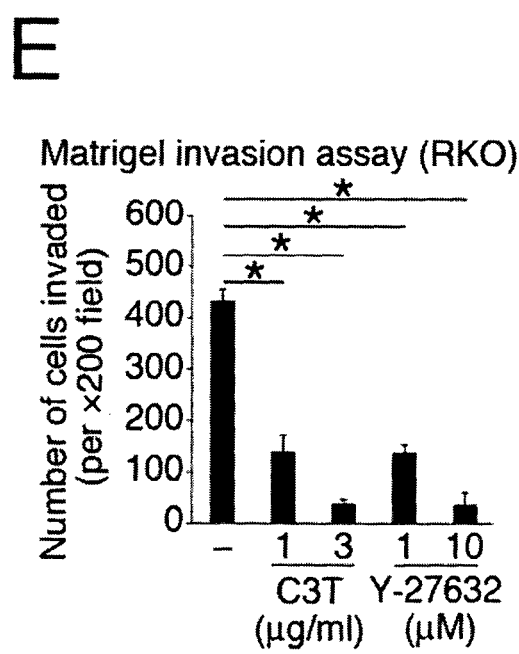
Figure 1F:
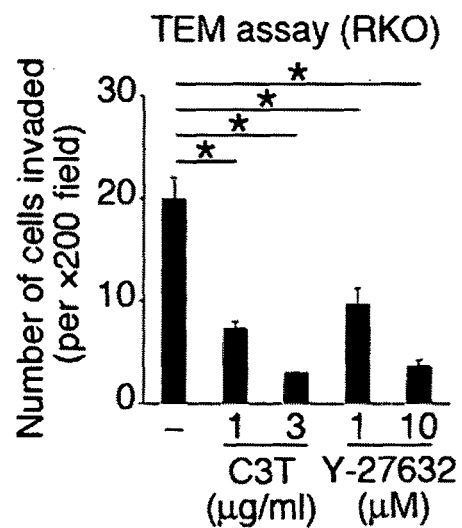
Figure 2A:
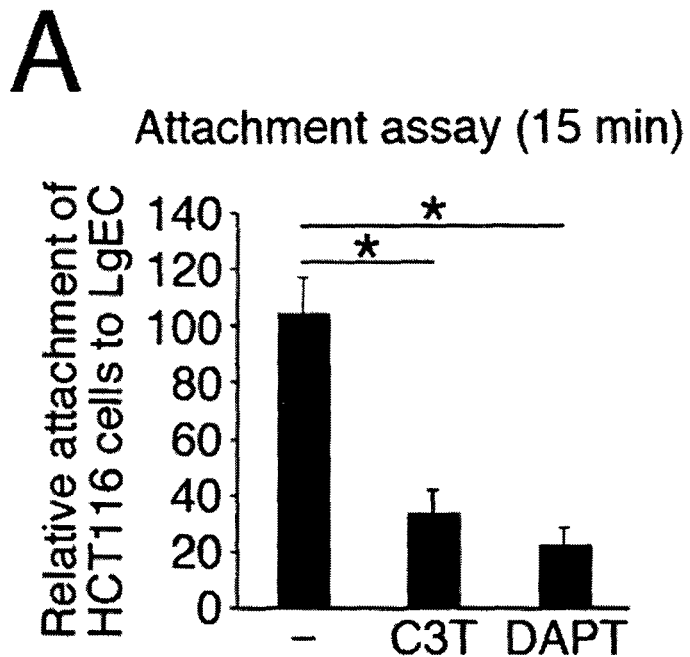
Figure 2B:
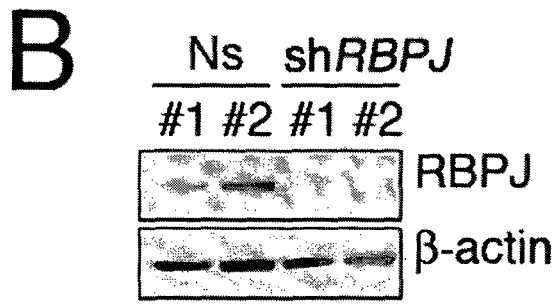
Figure 2C:
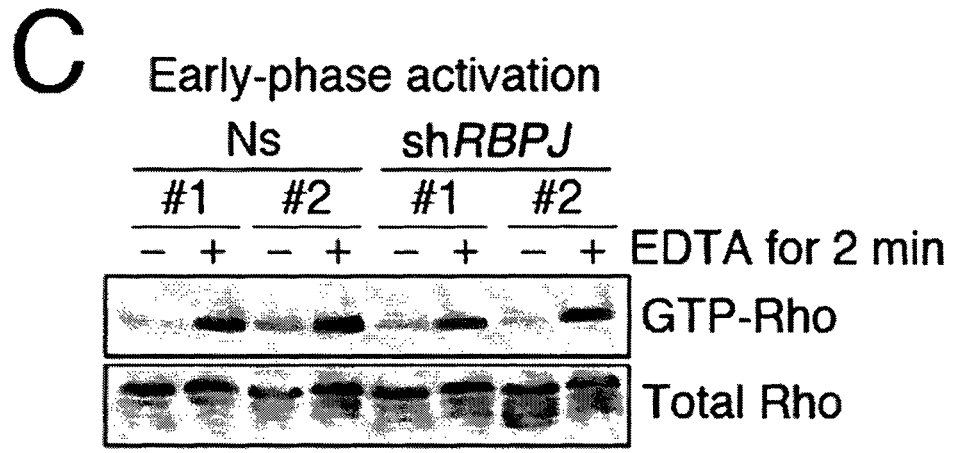
Figure 2D:
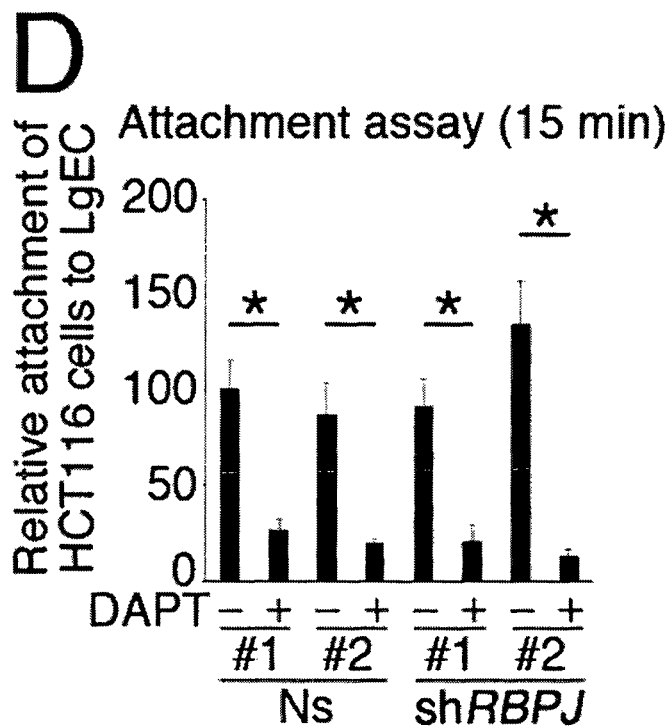
Figures 2E, 2F:
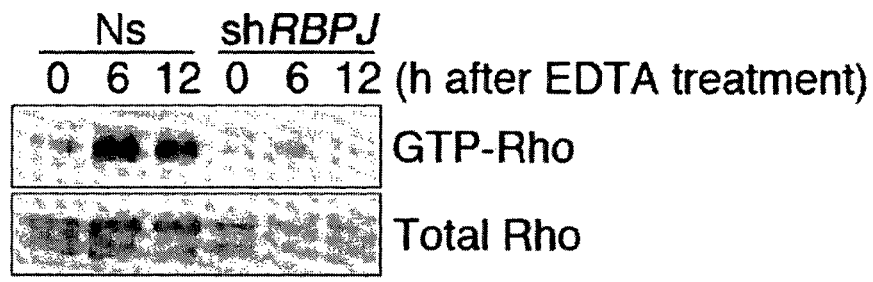
Figure 2G:
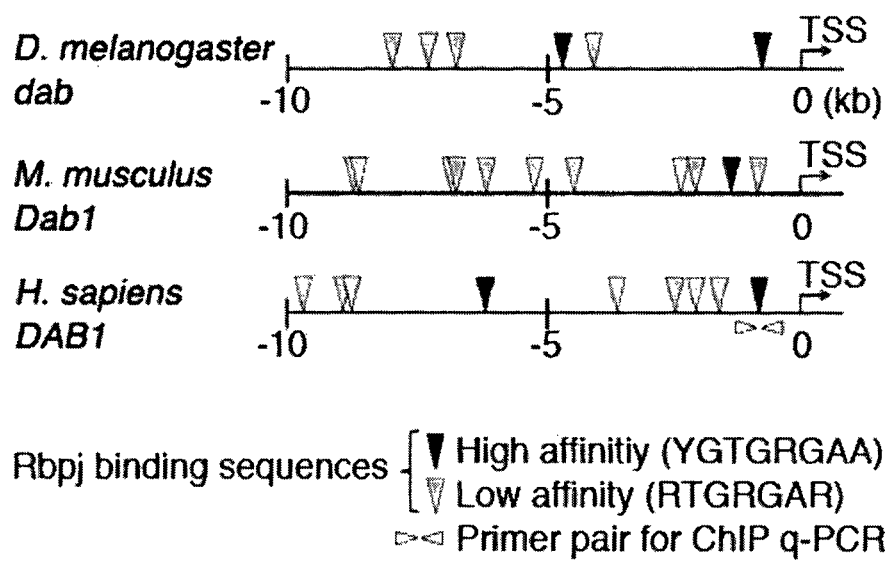
Figure 2H:
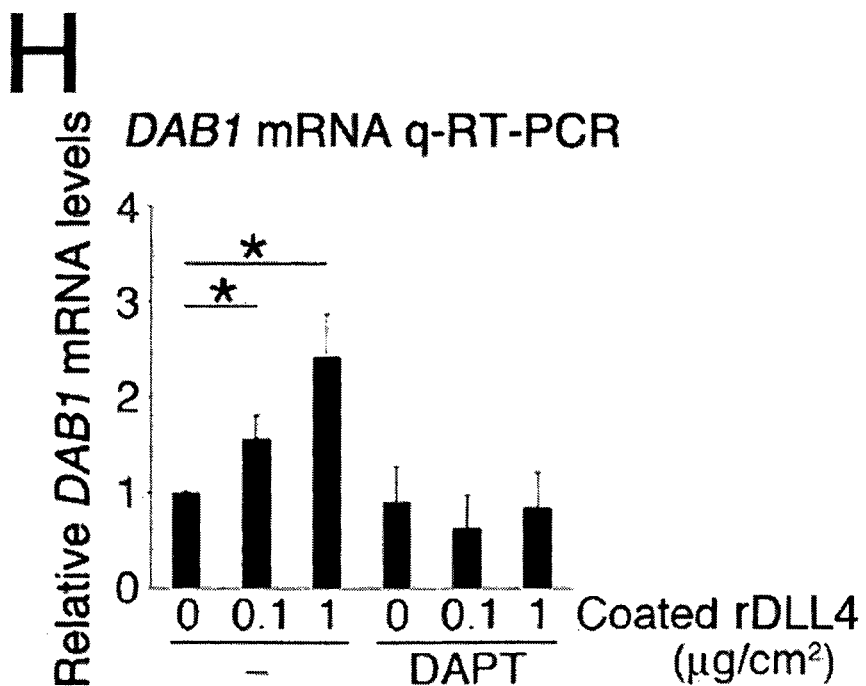
Figure 2I:
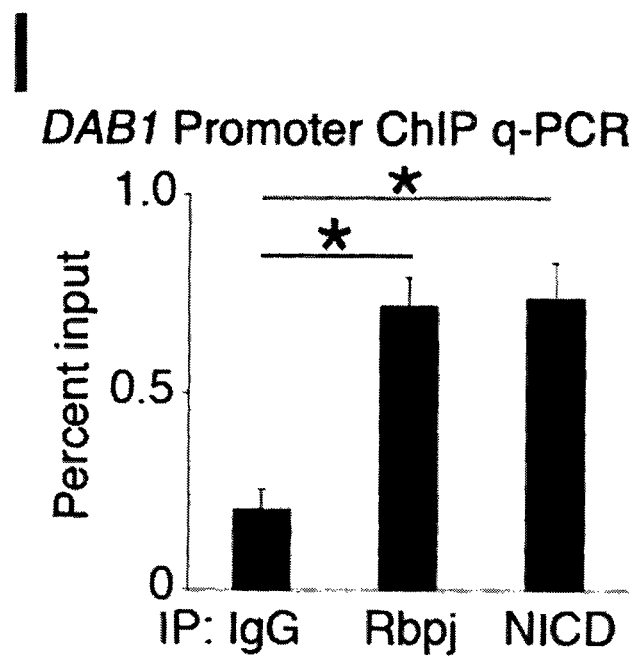

It is known that recombinant extracellular domain of a Notch ligand protein can activate Notch signaling if immobilized onto a solid surface {Varnum-Finney, 2000} (see also FIGS. 2H and 2I below). We have also reported that immobilized recombinant extracellular portion of DLL4 (rDLL4) stimulates migration of CRC cells in scratch assays. In Colon26 TetON-Aes-Flag cells, doxycycline-induced Aes inhibits Notch signaling, reducing migration in scratch assays {Sonoshita, 2011}. During the migration of this cell line after scratch, we found ~1.7-fold activation of Rho, which was suppressed significantly by induction of Aes (FIG. 1D). These results suggest that Notch signaling activates Rho to accelerate CRC progression.

Figure 8A:
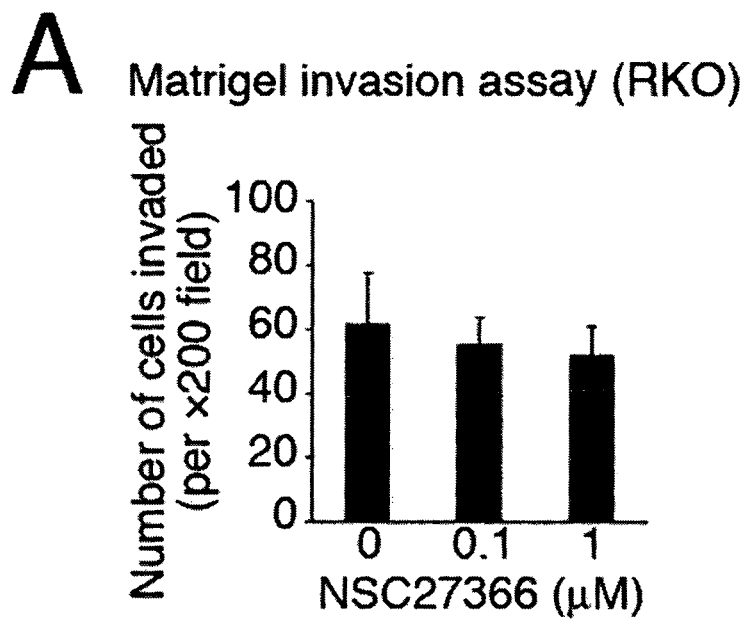

We have reported that CRC cells invade into Matrigel, mixture of extracellular matrix produced in mice, in a Notch signaling-dependent manner {Sonoshita, 2011}. Interestingly, Rho inhibitor C3T or Rock inhibitor Y-27632 suppressed both Matrigel invasion and TEM of RKO human CRC cells in dose-dependent manners (FIGS. 1E and F), as well as of HCT116, another human CRC cell line (data not shown). On the other hand, inhibition of Rac with a specific inhibitor NSC23766 did not affect the CRC cell invasion in culture (FIG. 8A). These results indicate that activation of Rho by Notch signaling is critical for CRC invasion.

Figure 1G:
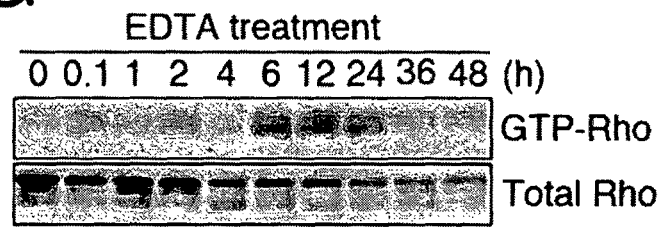
Figure 1H:
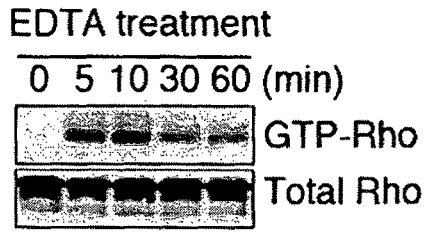
Figure 1I:
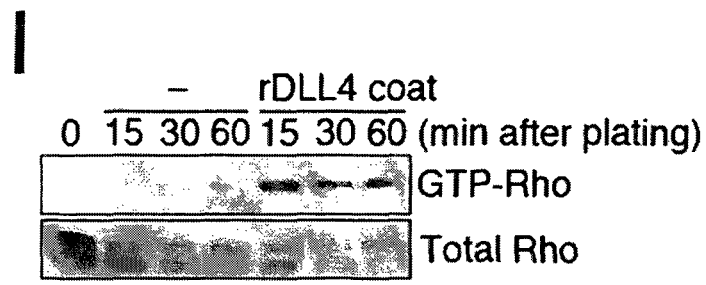
Figure 1J:
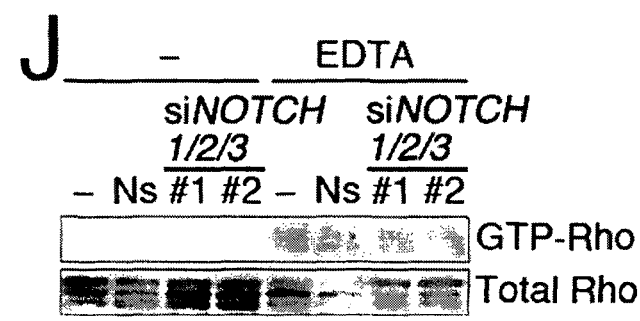
Figure 1K:
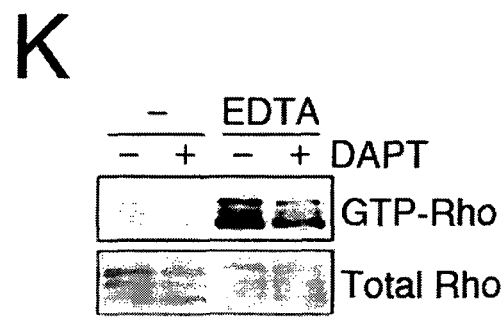
Figure 8B:
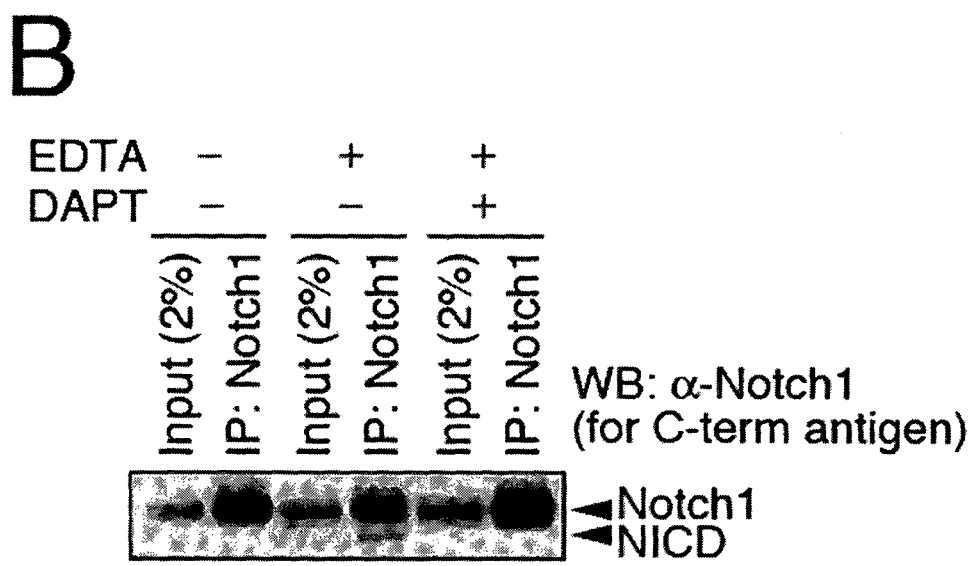
Figure 8C:

To determine the chronology of Rho activation, we treated RKO cells with 10 mM EDTA for 2 minutes to induce conformational changes in the Notch receptor, and allowed subsequent cleavage at the S3 site by γ-secretase {Rand, 2000; Tiyanont, 2011}. As expected, we detected the cleaved receptor NICD upon the EDTA treatment, which was blocked by a γ-secretase inhibitor (GSI) DAPT (FIG. 8B). Consistent with the chronology of Rbpj-induced target gene expression, we observed strong Rho activation 6-12 h after EDTA treatment (FIG. 1G). Interestingly, we also noticed transient and moderate Rho activation as early as 5 minutes after EDTA treatment (FIG. 1G). This early activation peaked in 5-10 minutes, and tapered off in 4 h (FIGS. 1G and H). Similar results were obtained with Colon26 and CMT93 mouse CRC cells, as well as with DLD1, SW480 and LS174T human CRC cells (FIG. 8C and data not shown). Consistent with these results, rDLL4 ligand immobilized on the dish surface also activated Rho in cultured CRC cells (FIG. 1I). Furthermore, Rho activation was inhibited when Notch receptor expression was knocked-down (FIG. 1J) or when Notch receptor activation was inhibited by DAPT (FIG. 1K).

Collectively, these data show two distinct phases in Rho activation by the ligand-dependent Notch receptor activation; the early- (within a few minutes) and late-phase (>6 hours) responses that are independent of and dependent on, respectively, Rbpj-mediated transcription of the target genes (see below).

Early-Phase Response: Activation of Rho in CRC Cells is Critical for their Adhesion to ECs To initiate intra- and extra-vasation, it is necessary for cancer cells to adhere to and migrate through the vascular lining {Miles, 2008; Weinberg, 2007}. We previously reported that ECs stimulate Notch signaling in adjoining CRC cells {Sonoshita, 2011}. Accordingly, we hypothesized that Rho was activated in CRC cells by Notch signaling immediately after making contacts with ECs, enforcing the attachment. As anticipated, C3T (Rho inhibitor) or DAPT (GSI) reduced the number of CRCs remaining attached to the EC layer after washing at 15 min post plating (FIG. 2A). Importantly, RBPJ knockdown in CRC cells (FIG. 2B) did not affect the early-phase Rho activation or the adhesion to ECs (FIGS. 2C and 2D). Consistently, DAPT prevented EC cell adhesion of CRC cells even when RBPJ was knocked-down (FIG. 2D). These results suggest that Notch receptor cleavage activates Rho in the early-phase to promote adhesion of CRC cells to ECs in an Rbpj-independent manner.

Late-Phase Response: Rbpj Transcription Induces Disabled1 (DAB1/Dab1) Expression and Activates Rho Unlike the early-phase response, we found that the late-phase response was significantly suppressed by RBPJ-knockdown (FIG. 2E). Thus, we speculated that expression of Rbpj target genes was indispensible for the late-phase, activation of Rho, and that this activation helps intra- and extra-vasation of CRC cells after their initial attachment to EC.

Recently, 98 genes were reported as Rbpj targets in NICD transgenic mice {Li, 2012}. Interestingly, 3 genes among them were also induced by Notch signaling in *Drosophila* {Krejci, 2009}. They were Disabled1 (Dab1) (disabled in *Drosophila*), Notch1 (Notch), and Hes1/5 (E(sp1)) genes (FIG. 2F).

We focused on DAB1 in this study because Dab1 enhances neuron motility during brain development {Sanada, 2004, Hashimoto-Torii, 2008}. We found that both human DAB1 and mouse Dab1 genes contain high affinity Rbpj binding sequence motifs in their proximal promoter regions like in *Drosophila* (FIG. 2G), suggesting evolutionally-conserved transcription by Rbpj {Dowell, 2010}. On the other hand, we found that induction of Hes1 caused massive death of CRC cells (data not shown).

To study the effects of Notch receptor activation on DAB1 expression, we applied immobilized rDLL4 to LS174T human CRC cells that had a substantial DAB1 mRNA level among human CRC cell lines (FIG. 9). We found that rDLL4 increased expression of the DAB1 mRNA in a dose-dependent manner whereas DAPT inhibited it (FIG. 2H). In addition, Rbpj was preferentially bound to the DAB1 gene promoter (FIGS. 2G and 2I). NICD was also enriched in the promoter DNA fragments, suggesting that the Notch trans-activation complex induced DAB1 expression. Similar results were obtained with another CRC cell line Colo205 that also expressed relatively abundant DAB1 (FIG. 9 and data not shown).

Figure 2J:
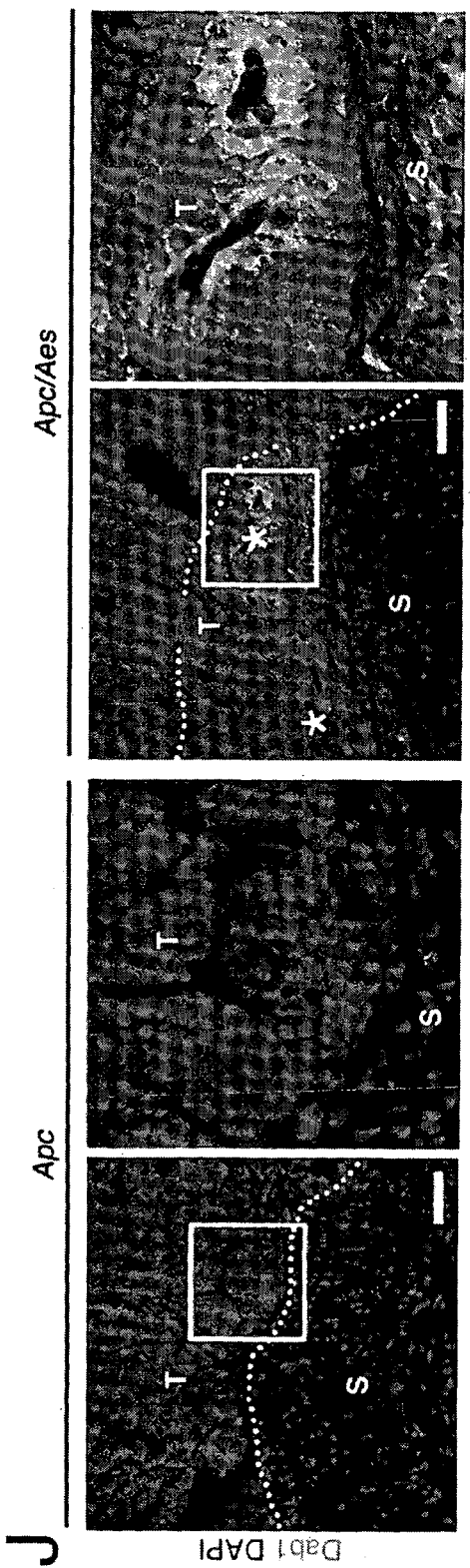

We also found marked induction of Dab1 in CRCs in Apc/Aes mice where Notch signaling was activated {Sonoshita, 2011}, but not in adenomas of Apc mice (FIG. 2J). Collectively, these results indicate that DAB1 is one of the Notch transcription targets in CRC cells.

DAB1 can Stimulate CRC Invasion and Metastasis Through Rho Activation

Figure 3A:
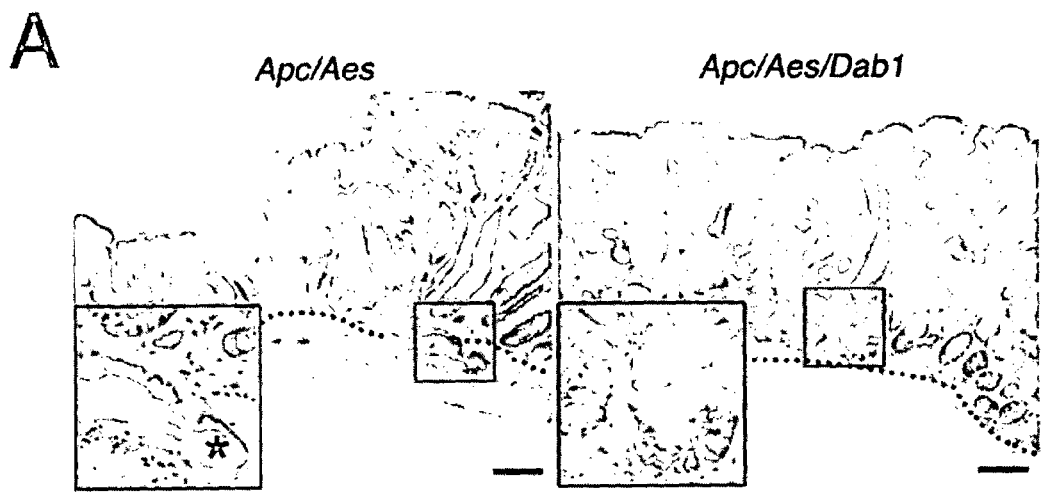
Figure 3B:
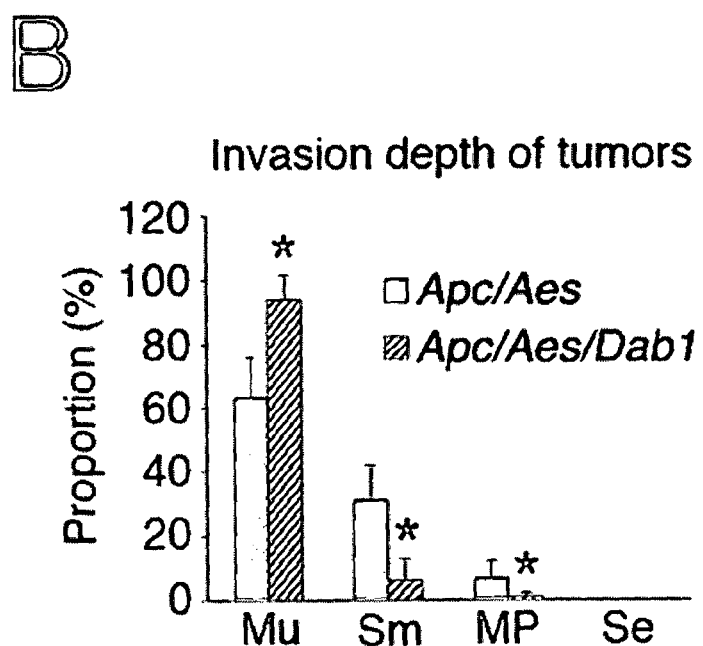

To determine the roles of DAB1 in CRC progression, we introduced homozygous null mutation of Dab1 additionally into the Apc/Aes mice and constructed Apc/Aes/Dab1 triple mutant mice. Notably, we found that Dab1 mutation inhibited invasion and intravasation of intestinal tumors (FIGS. 3A and 3B).

Figure 3C:
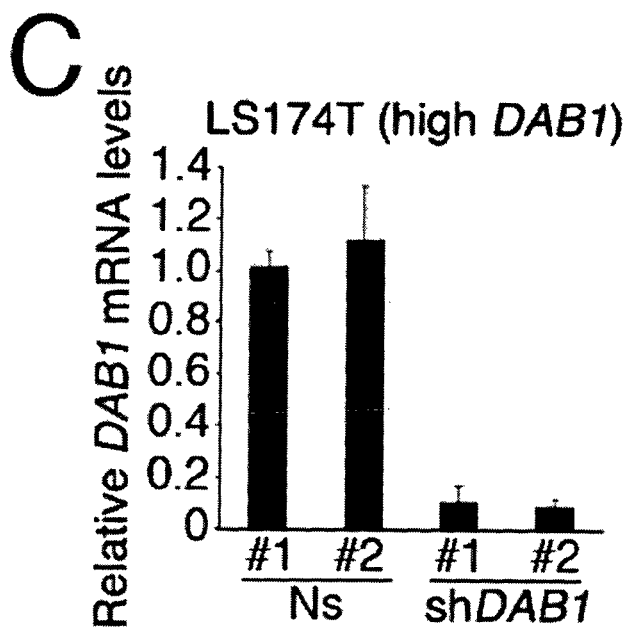
Figure 3D:
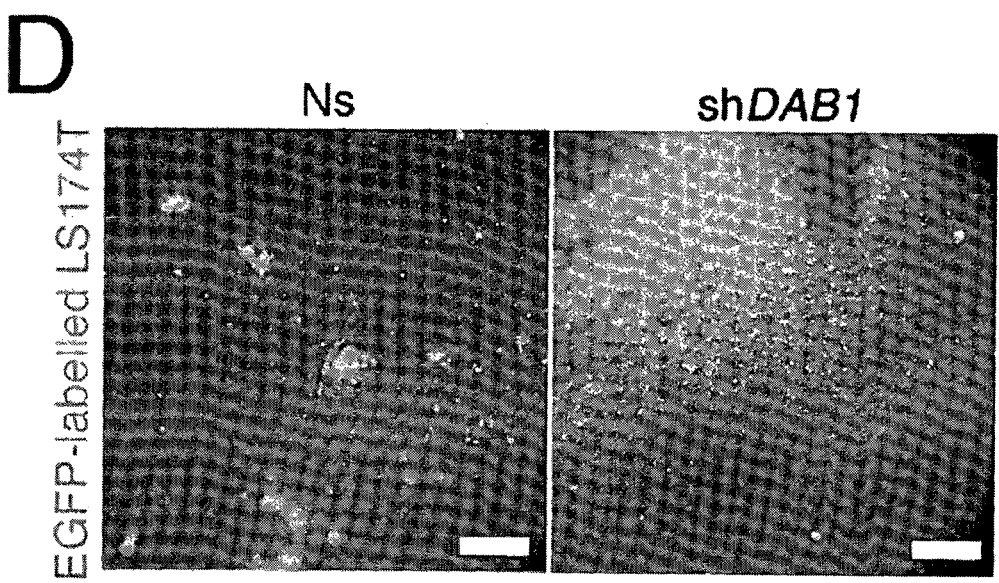
Figure 3E:
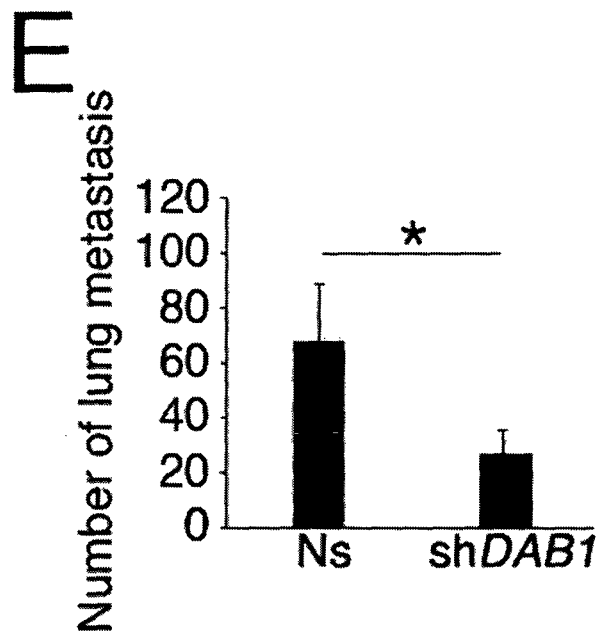
Figure 3F:
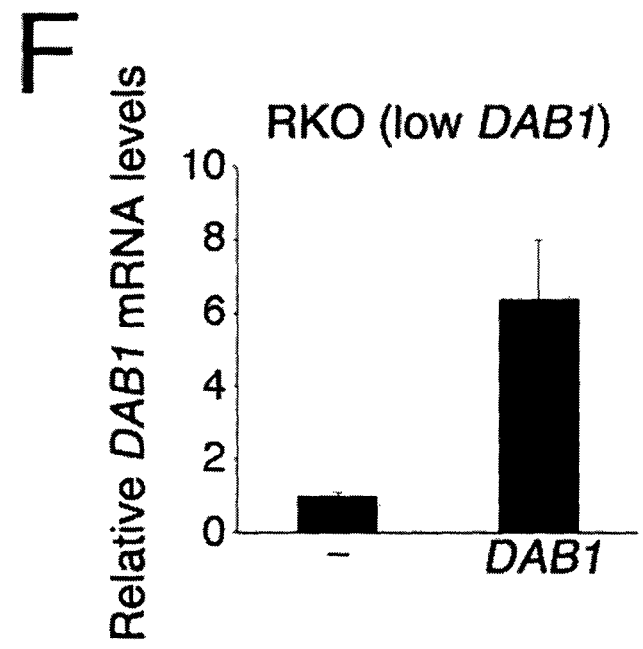
Figure 3G:
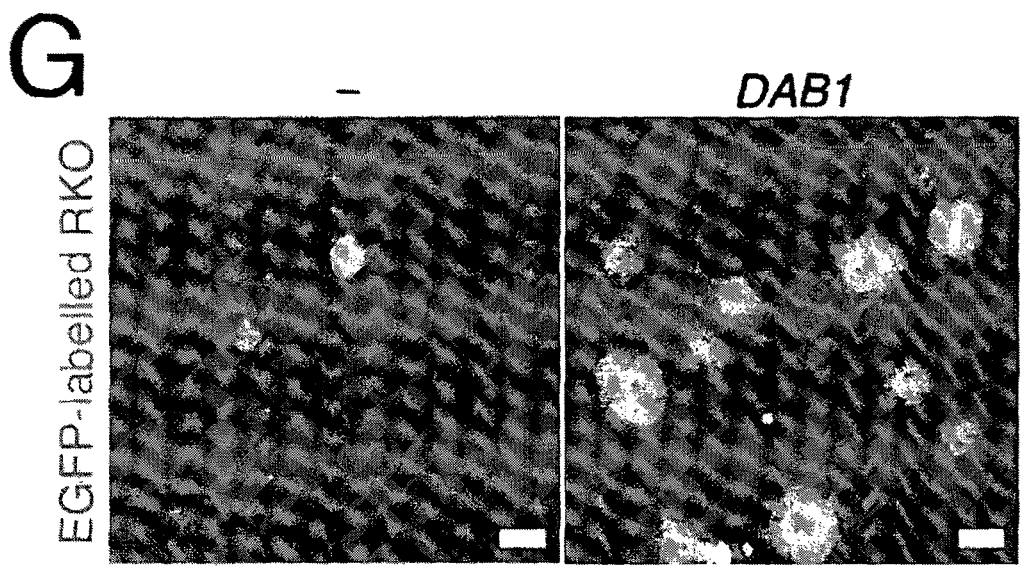
Figure 3H:
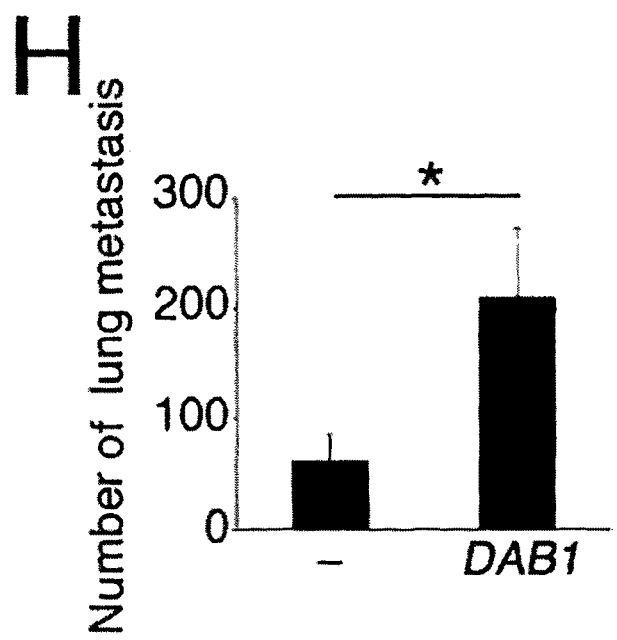

To confirm the pro-metastatic roles of DAB1 in CRC, we also constructed clonal LS174T derivatives where DAB1 expression was knocked down constitutively (FIG. 3C). After their transplantation into the nude mouse rectum, we found a significant decrease in the number of lung metastatic foci with the DAB1-knockdown cells compared to that with the control cells (FIGS. 3D and 3E). On the other hand, expression of DAB1 in RKO, one of the low expresser CRC cell lines (FIG. 9), increased the lung metastasis from the rectum (FIGS. 3F, 3G and 3H).

Figure 3I:
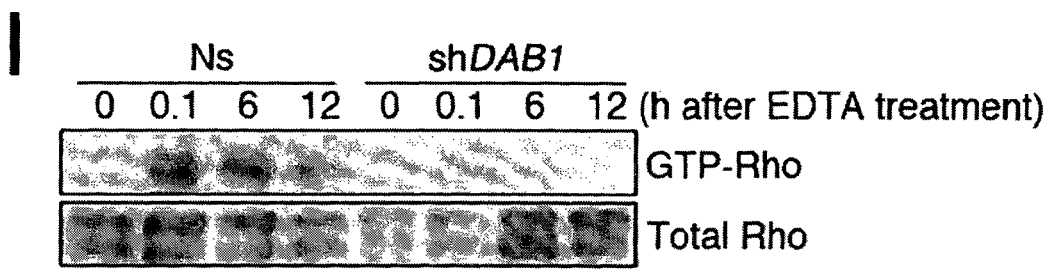
Figure 3J:
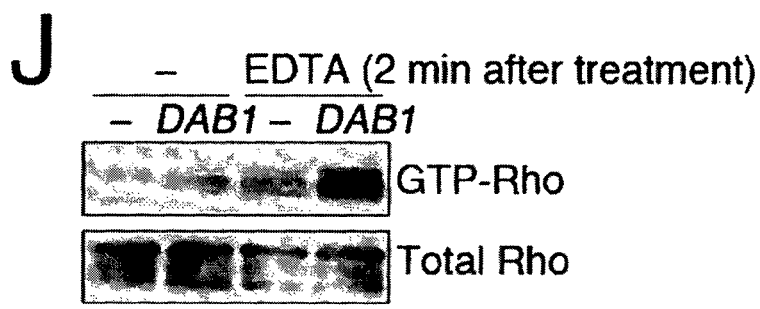
Figure 3K:
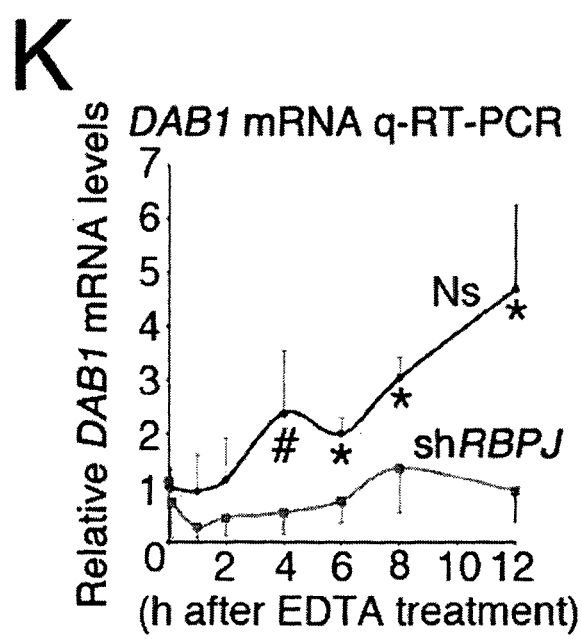

Importantly, both the early- and late-phase Rho activation responses were suppressed in DAB1-knockdown CRC cells (FIG. 3I). On the other hand, expression of DAB1 alone was sufficient to activate Rho constitutively. The early-phase activation of Rho was also potentiated by DAB1 expression (FIG. 3J). We also noticed that DAB1 mRNA was induced in control non-silencing, but not in RBPJ-knockdown, CRC cells at around 4 h after Notch activation by EDTA (FIG. 3K). Taken together, it is strongly suggested that in the early-phase after Notch cleavage, endogenous DAB1 activates Rho, and thereafter, Rbpj-induced DAB1 contributes to the late-phase and persistent Rho activation. This interpretation is compatible with the results that knockdown of RBPJ attenuated only the late-phase, but not the early-phase, Rho activation (FIGS. 2C and 2E).

Dab1 Activates Tyrosine Kinase Abl, which Plays an Essential Role in Notch-Mediated Rho Activation and CRC Invasion In differentiating mouse pheochromocytoma cells, DAB1 was identified as one of the proteins that bound SRC family tyrosine kinases including SRC and FYN, as well as Abelson (ABL) {Howell, 1997}. In Drosophila, the Notch receptor gene (N) genetically interacted with Abl in axon guidance {Giniger, 1998}. The ABL subfamily of tyrosine kinases is conserved evolutionally, containing ABL1 and ABL2 (aka ARG) in mammals, and plays pleiotropic roles in various physiologic and pathologic processes such as cell proliferation and migration {Colicelli, 2010}.

Figure 4A:
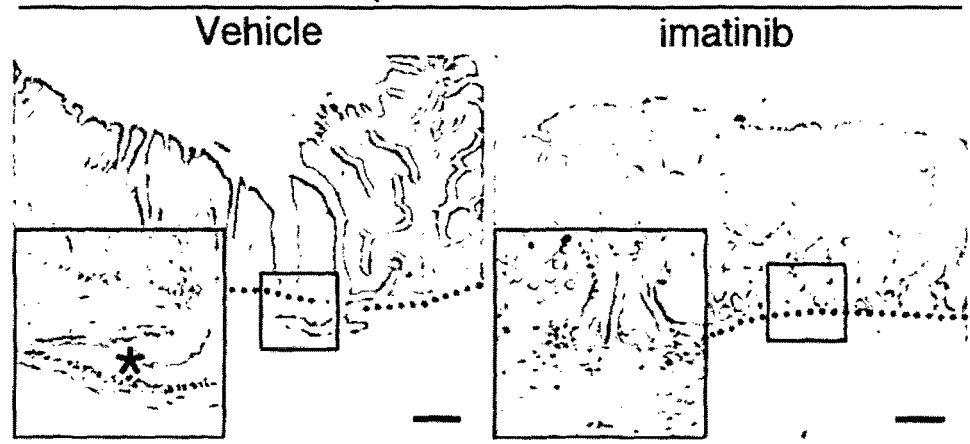
Figure 4B:
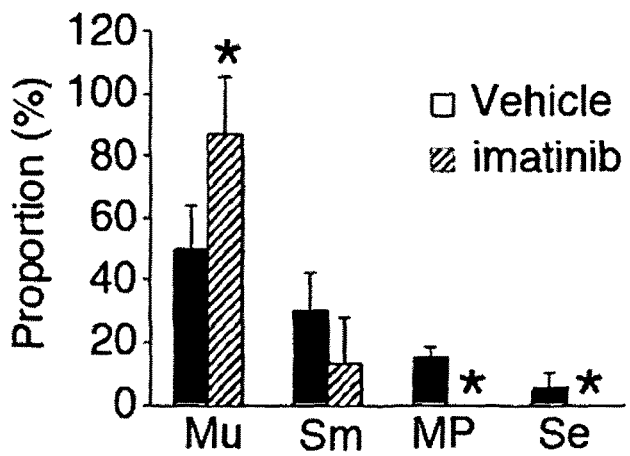
Figure 4C:
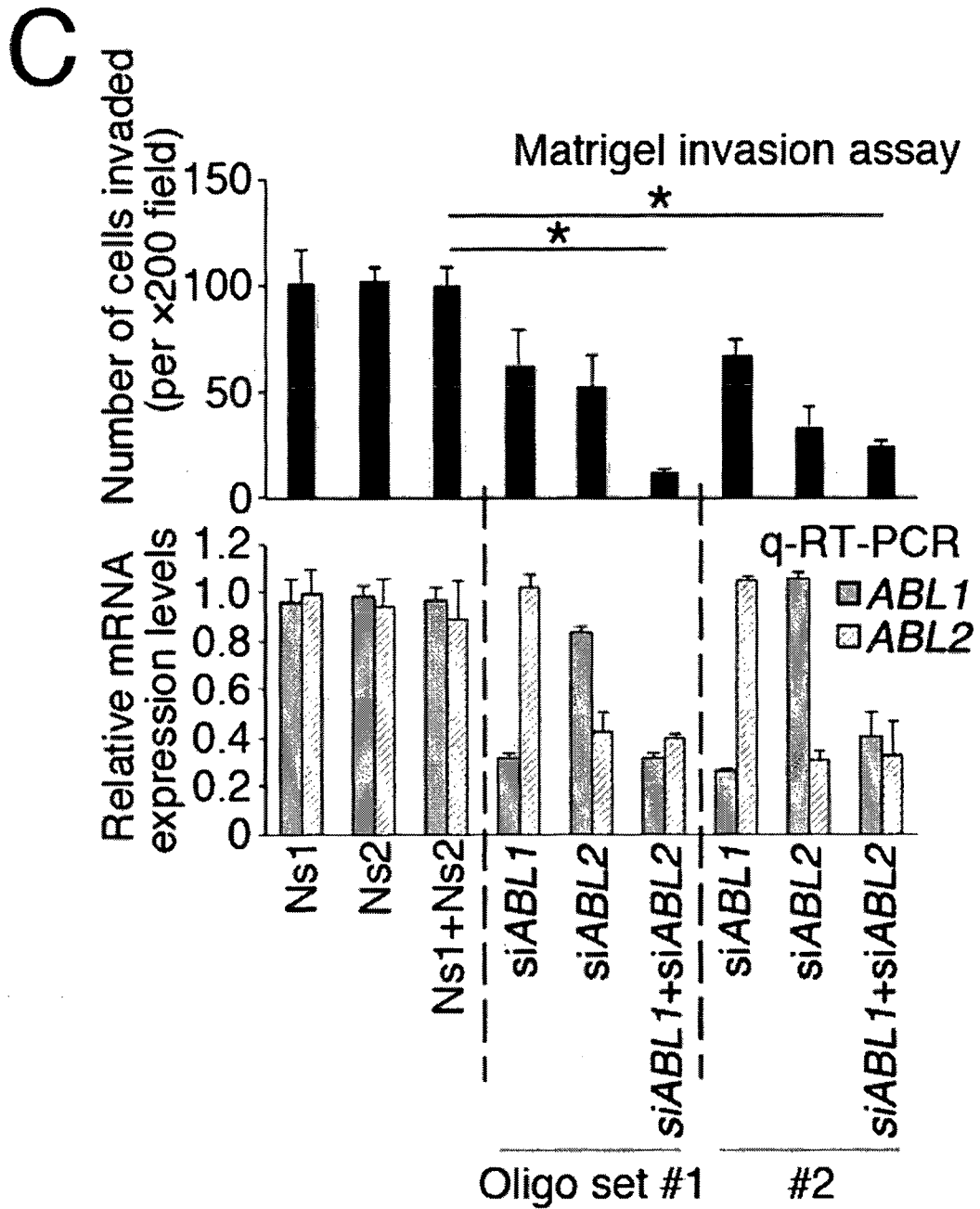
Figure 4D:
Figure 4E:
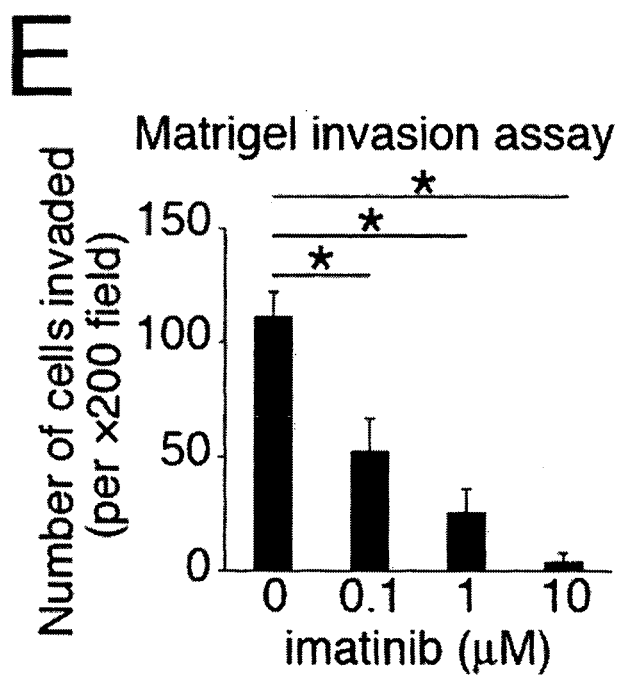
Figure 4F:
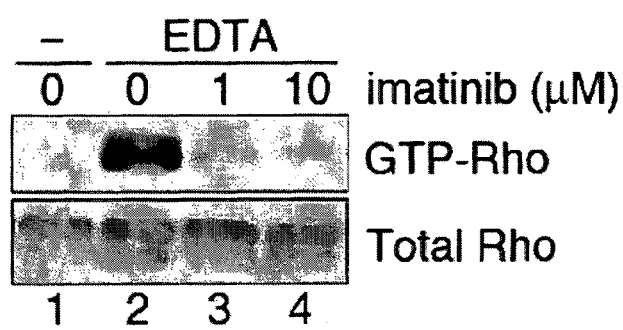
Figure 10A:
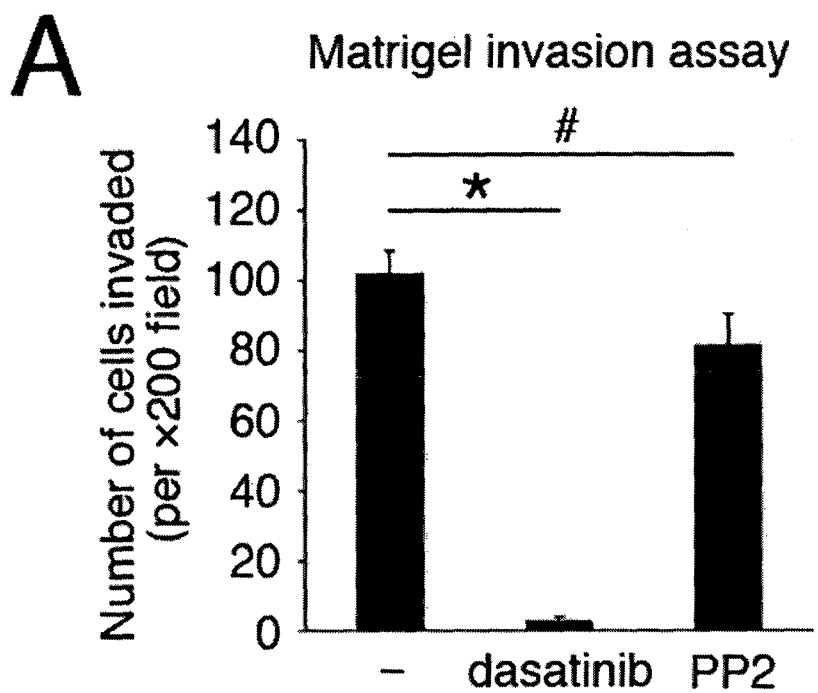

Accordingly, we hypothesized that DAB1 promoted CRC metastasis by activating ABL. To determine the possible roles of ABL in progression of endogenous CRC, we treated Apc/Aes mice with ABL inhibitor imatinib (aka Glivec {Buchdunger, 2001; Sawyers, 2003}), and found significant suppression of CRC invasion without changing the tumor size or number (FIGS. 4A and 4B). Consistently, knockdown of ABL1 and/or ABL2 genes (FIG. 4C, bottom) reduced Matrigel invasion of RKO cells significantly (FIG. 4C, top). Furthermore, Rho activation was suppressed by the double ABL1/ABL2 knockdown (FIG. 4D). Likewise, imatinib blocked the invasion and Rho activation induced by EDTA in dose-dependent manners (FIGS. 4E and 4F). We also found that dasatinib, a dual inhibitor of both ABL and SRC, also suppressed the invasion significantly (FIG. 10A). Although SRC is hyperactivated in a subset of advanced CRC cases {Weinberg, 2007b}, we found that SRC family inhibitor PP2 had only a minor effect (by ~20%) on the RKO cell invasion in culture (FIG. 10A). Essentially the same results were obtained with HCT116 cells (data not shown). These results suggest that ABL has a role downstream of Notch in Rho activation and CRC progression.

In neurons and HEK293 cells, DAB1 enhances the kinase activity of FYN {Arnaud, 2003; Bock, 2003}. In our assay for CRC invasion, however, SRC family inhibitor PP2 showed only a minor inhibition (FIG. 10A). Accordingly, we asked whether DAB1 interacted with ABL1B, the major and well-characterized splicing variant of ABL1 {Hantschel, 2004, Colicelli, 2010}, to stimulate CRC invasion.

Figure 4G:
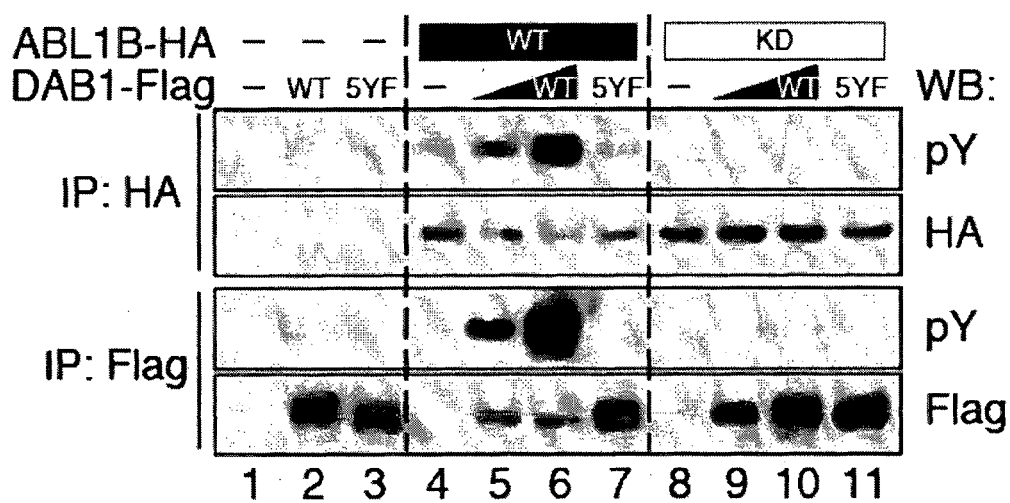
Figure 10B:
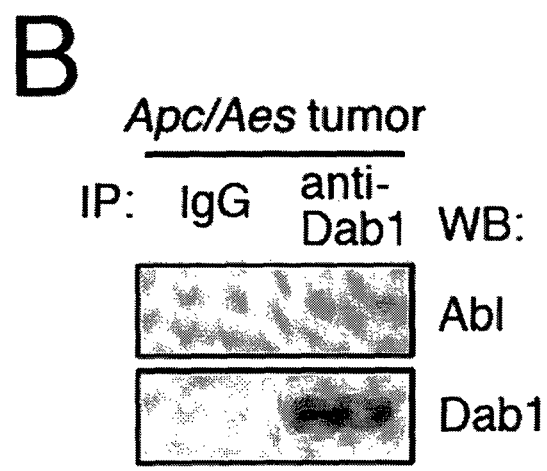

It is known that ABL phosphorylates itself for the maximal kinase activity {Hantschel, 2004}. We found that simultaneous expression of DAB1 increased the level of Tyr-phosphorylated ABL1B (pY-ABL1B) in a dose-dependent manner (FIG. 4G; compare lanes 4-6). In neurons, Tyr-phosphorylated DAB1 (pY-DAB1) was essential for their migration, because it was compromised by expression of the 5YF-DAB1 mutant where the five Tyr residues were replaced with structurally similar, but non-phosphorylatable Phe {Sanada, 2004}. In the CRC cells expressing 5YF-DAB1, we found that the pY-ABL1B level remained low (FIG. 4G; lane 7), indicating that ABL activation was dependent on pY-DAB1. We also found that wild-type DAB1 was Tyr-phosphorylated in the presence of ABL1B but not 5YF-mutant (FIG. 4G; lanes 5-7). It was conceivable that ABL1B directly Tyr-phosphorylated DAB1, because ABL and DAB1 interact with each other physically in mouse intestinal tumors and cultured cells (FIG. 10B and Howell, 1997). Consistent with this interpretation, DAB1 was not phosphorylated in the presence of a kinase-dead (KD) mutant of ABL1B (K290R; Barilá, 2000) (FIG. 4G; lanes 9-10).

These results collectively suggest that DAB1 is phosphorylated in vivo in the presence of ABL, and the pY-DAB1 activates ABL reciprocally to stimulate CRC invasion as one of the downstream effectors of Notch receptor. We propose that ABL activity is a novel therapeutic target against malignant progression of CRC.

TRIO RhoGEF is Tyr-Phosphorylated in the Presence of DAB1 and ABL, and Promotes CRC Invasion In fly neuronal migration, Drosophila Triple functional domain (dTrio) plays key roles as a downstream effecter of dAbl {Forsthoefel, 2005}. TRIO belongs to the DBL family of GEF proteins that can activate Rho family small GTPases, and is its unique member carrying two GEF domains; one for Rac (GEF1) and the other for Rho (GEF2) (FIG. 5A) {Debant, 1996; Bateman; 2001, Vigil; 2010}. It has been shown that Trio GEF1 activates Rac and causes neuronal migration in Drosophila {Song, 2012}. Because Rac remained unactivated in Apc/Aes mouse CRC, and its inhibition had little effects on CRC invasion (FIG. 8A and data not shown), we focused on Rho activation by TRIO in CRC progression.

Figure 5A:
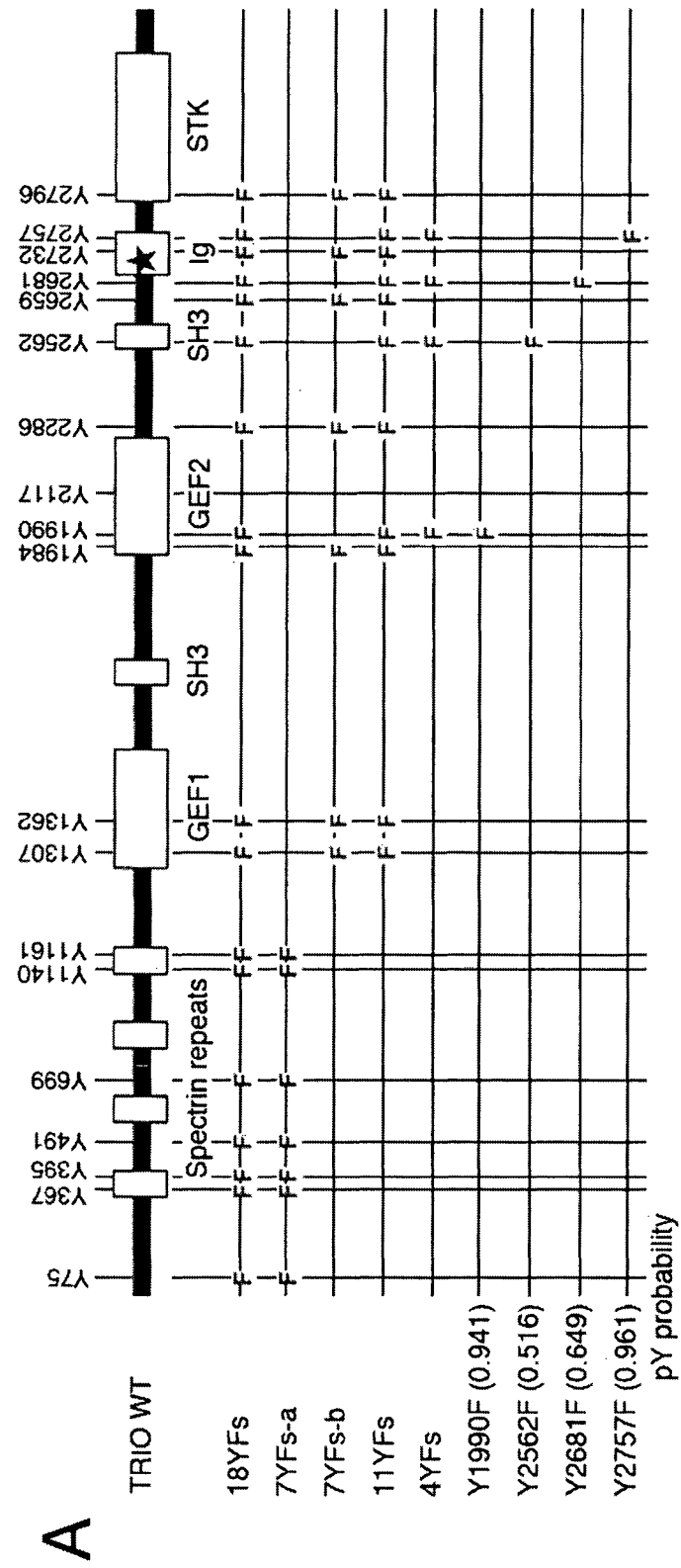
Figure 5B:
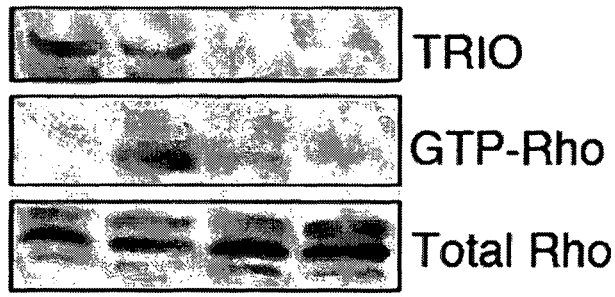
Figure 5C:
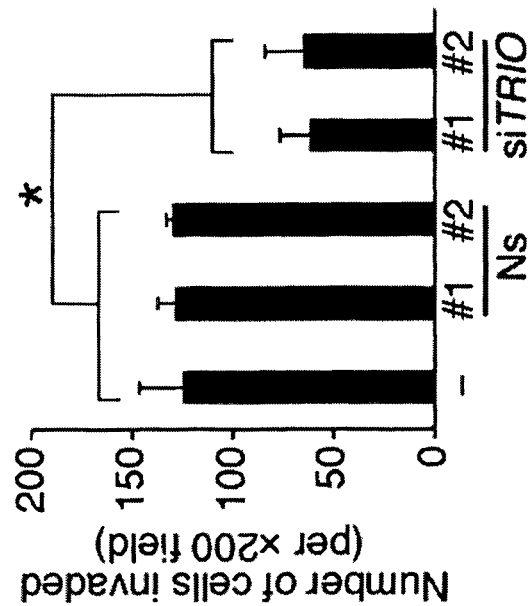
Figure 5C:
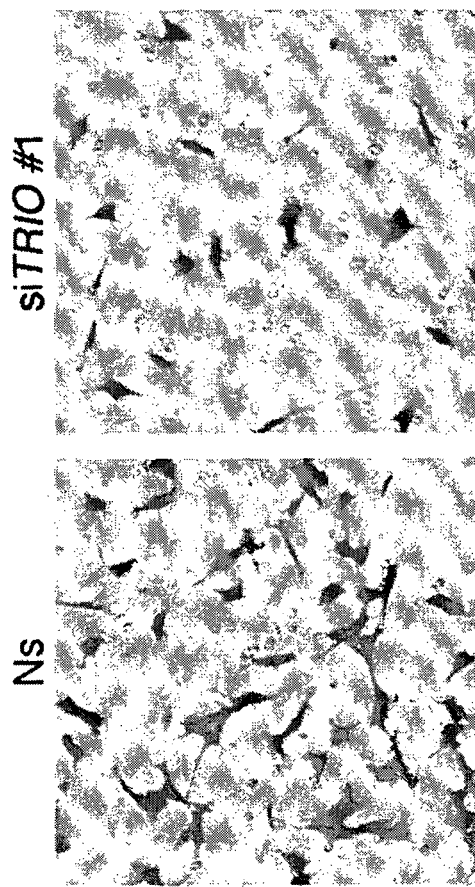

Namely, we first knocked down TRIO mRNA expression in HCT116 cells and determined the levels of GTP-Rho upon Notch receptor activation with EDTA. Notably, TRIO knockdown caused significant reduction in the GTP-Rho level and Matrigel invasion capacity (FIGS. 5B and 5C). We obtained essentially the same results with RKO cells as well (data not shown). These results strongly suggest that TRIO plays a key role in CRC invasion through Rho activation in Notch receptor-activated cells.

Figure 5D:
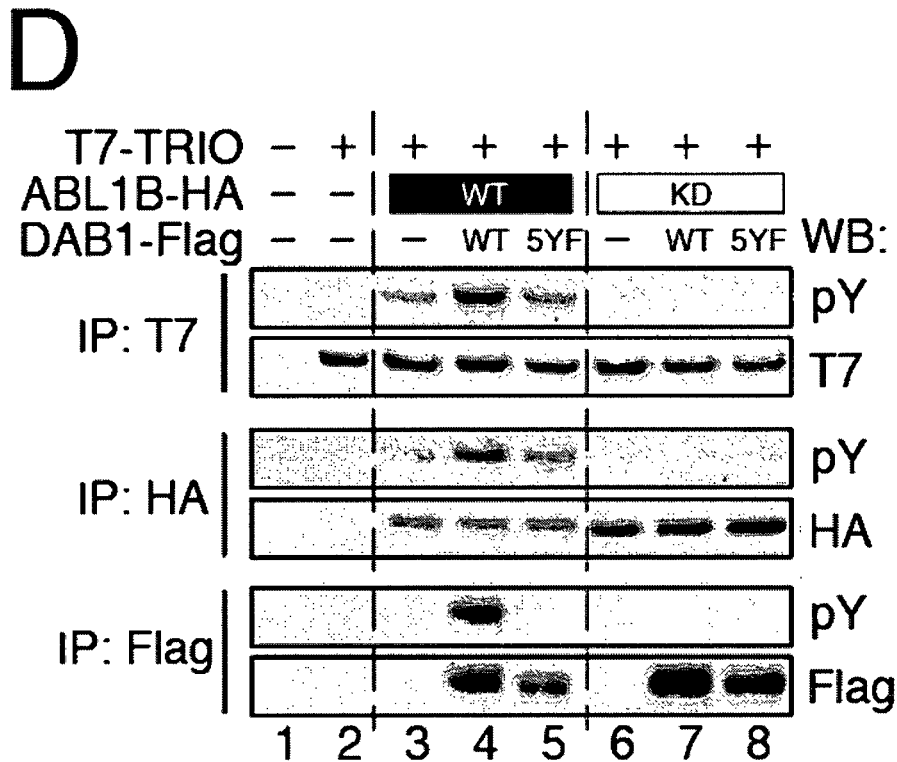

As dTrio was Tyr-phosphorylated in the presence of dAbl in Drosophila S2 cells {Forsthoefel, 2005}, we hypothesized that ABL caused Tyr-phosphorylation of TRIO also in CRC cells and increased their Rho activity. As hypothesized, we found that ABL1B alone slightly increased the level of pY-TRIO in CRC cells (FIG. 5D, lane 3). Interestingly, the level of pY-TRIO increased significantly when ABL1B was co-expressed with wild-type DAB1 but not with 5YF mutant DAB1 (FIG. 5D, lanes 4-5). On the other hand, the kinase-dead (KD) ABL1B mutant could not increase the pY-TRIO level (FIG. 5D, lanes 6-7). These results collectively indicate that Tyr-phosphorylation of TRIO was dependent on the kinase activity of ABL.

To determine the particular target Tyr residues in TRIO by ABL, we first screened the primary amino acid sequence of TRIO with online NetPhos2.0 software {Blom, 1999}. It predicted the probability of phosphorylation for all 61 Tyr residues, and identified 30 as likely candidates' with scores above the threshold of 0.5. We succeeded in constructing TRIO mutants where 18 of them were converted to Phe either singly or in combination (YF mutants in FIG. 5A).

Figure 5E:
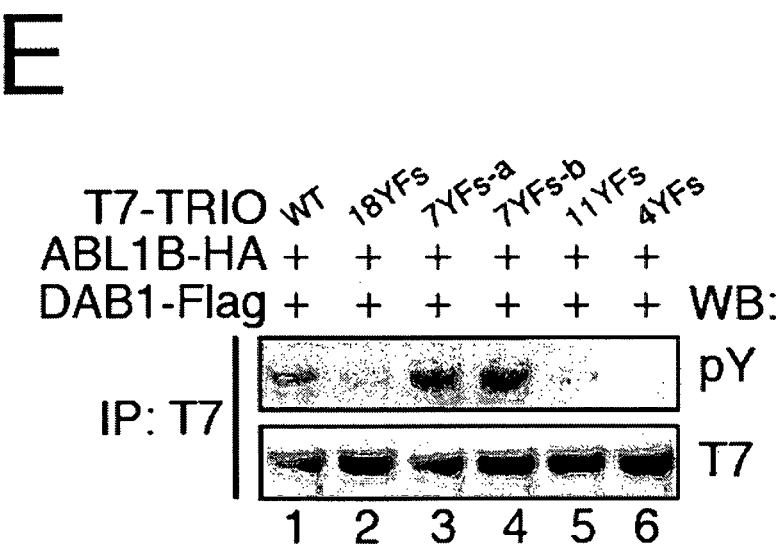
Figure 5F:
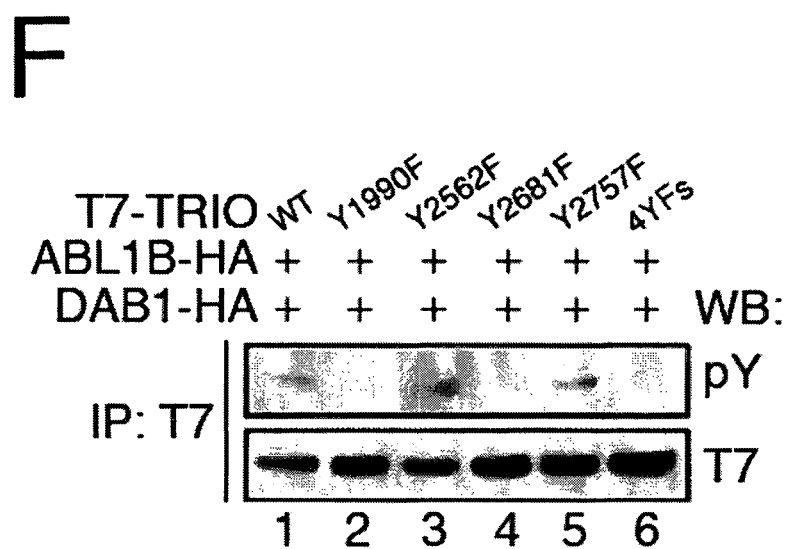

We then investigated whether the YF mutations affected the in vivo pY level of the TRIO protein as a whole, and found that TRIO(18YFs) showed significantly reduced pY level compared with TRIO(WT) (FIG. 5E, lanes 1-2). Although TRIO(7YFs-a) and TRIO(7YFs-b) were Tyr-phosphorylated similarly to control TRIO(WT), TRIO(11YFs) that contained additional four YF mutations at positions 1990, 2562, 2681 and 2757 had markedly reduced pY level (FIG. 5E, lanes 3-5). We observed similar reduction in the pY levels for the TRIO(4YFs) mutant where only the additional four tyrosines were mutated (FIG. 5E, lane 6). Among these four tyrosines, we identified Y1990 and Y2681 as the key targets of phosphorylation in the presence of ABL-DAB1, because the Y1990F and Y2681F mutants showed only modest pY levels (FIG. 5F, lanes 2 and 4, respectively).

TRIO(pY2681) Helps Stratify CRC Patients with Poor Prognosis Even at Stages I and II To determine the clinical relevance of the TRIO phosphorylation, we investigated whether Y1990 and/or Y2681 were phosphorylated in human primary CRC specimens. To this end, we produced specific antibodies for TRIO(pY1990) and TRIO(pY2681), respectively (FIG. 11). However, the survival rate was not much different between the TRIO (pY1990)-positive and -negative CRC patients (p=0.9, data not shown).

Interestingly, the patients carrying TRIO(pY2681)-positive CRC showed statistically significant reduction in survival as compared with the patients carrying TRIO (pY2681)-negative CRC (all stages included, n=102, p=0.01 in chi-square test; FIG. 6A, left). When we focused on stages I and II combined TRIO(pY2681)-negative CRC patients had complete (100%) cure whereas the positive ones showed ~20% death in 5 years (n=63, p=0.04; FIG. 6A, center). Even for the stage II patients alone (n=46), similar distribution was observed between TRIO(pY2681)-positive patients and -negative subpopulations (p=0.1; FIG. 6A, right). Namely, TRIO(pY2681)-negative CRC patients were free of relapse if resected at stage I or II. Accordingly, the phosphorylation status of TRIO(Y2681) helps predict patient prognosis with a greater accuracy than other biomarkers {Salazar, 2010}.

Figure 6B:
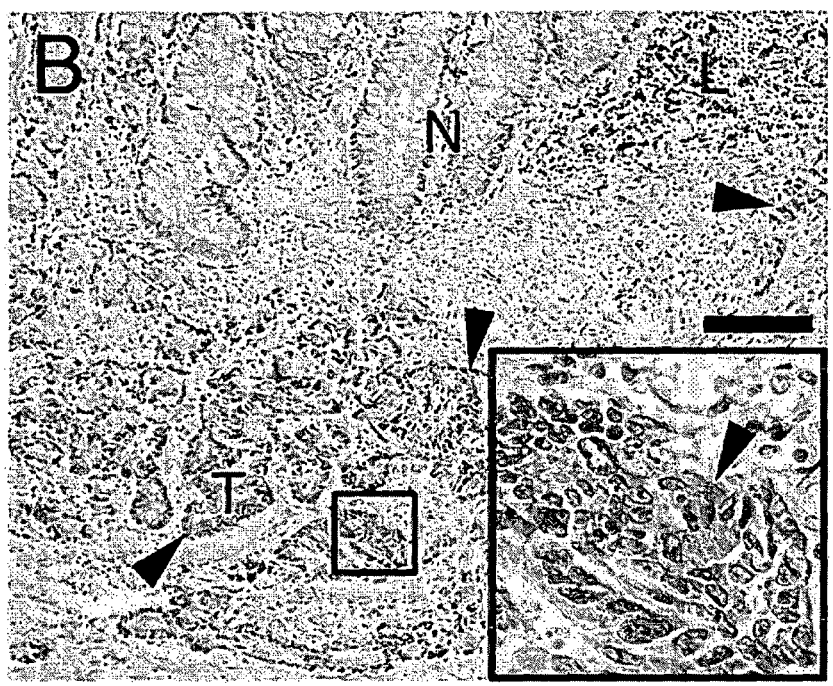
Figure 6C:
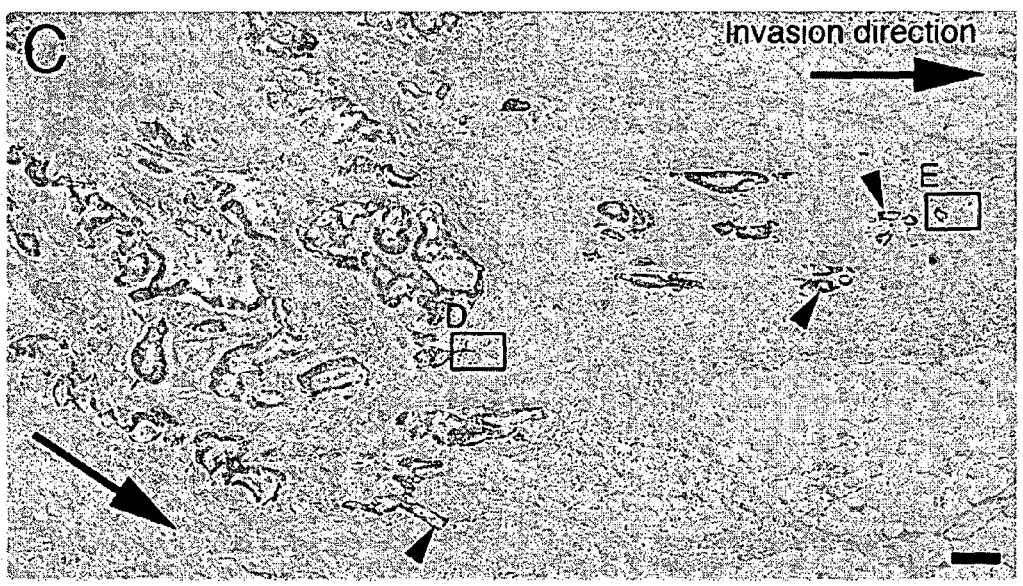
Figure 6D:
Figure 6E:

Compared with the adjacent normal mucosa or lymphoid follicles, CRC cells contained much higher levels of TRIO (pY2681) in the cytoplasm (FIG. 6B). Curiously, TRIO (pY2681) signals were also found in the isolated, budding or invading CRC cells in the stroma (arrowheads in FIGS. 6C-E), suggesting that TRIO(pY2681) was critical for CRC invasion. Indeed, the presence of TRIO(pY2681) was correlated with the depth of invasion (m, sm and mp vs. ss, se and si, p<0.0001 in chi-square test) and stages (stages 0-I vs. II-IV, p=0.02; stages 0-III vs. IV, p=0.02 in chi-square tests).

Aes Suppresses Phosphorylation of TRIO(pY2681)

Figure 7A:
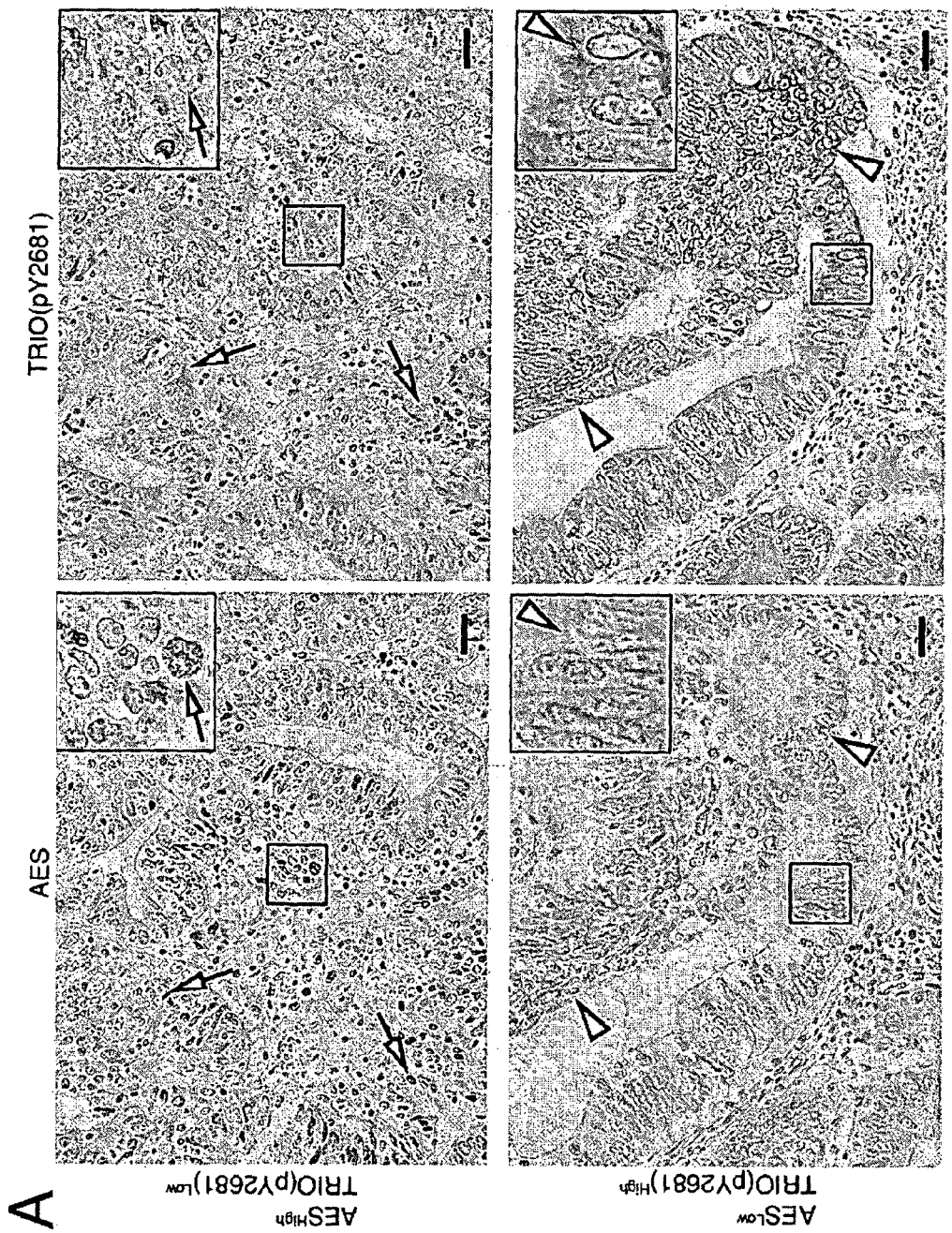
Figure 7B:
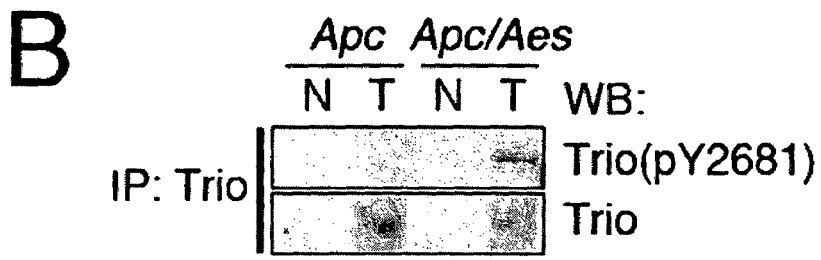

Aes suppresses CRC progression by inhibiting Notch signaling {Sonoshita, 2011}. Interestingly, nuclear expression of AES was inversely correlated with TRIO(pY2681) levels in human CRC specimens (p<0.01 in chi-square test, representative photos in FIG. 7A). Furthermore, we found stronger pY2681 signal in the immunoprecipitated Trio from Apc/Aes intestinal tumors than those from Apc mice (FIG. 7B). Therefore, we hypothesized that phosphorylation of TRIO(Y2681) is critical for CRC metastasis caused by loss of AES. Because Aes sequesters effectors of Notch signaling including NICD, Maml and Rbpj to nuclear foci {Sonoshita, 2011}, it is conceivable that Aes inhibits phosphorylation of TRIO(Y2681) by blocking both the early- and the late-phase responses mediated by NICD. Collectively, these results show that the AES has a key role in the activation of TRIO RhoGEF (GEF2).

Phosphorylation of TRIO(Y2681) Stimulates RhoGEF Activity and CRC Invasion

Figure 7C:
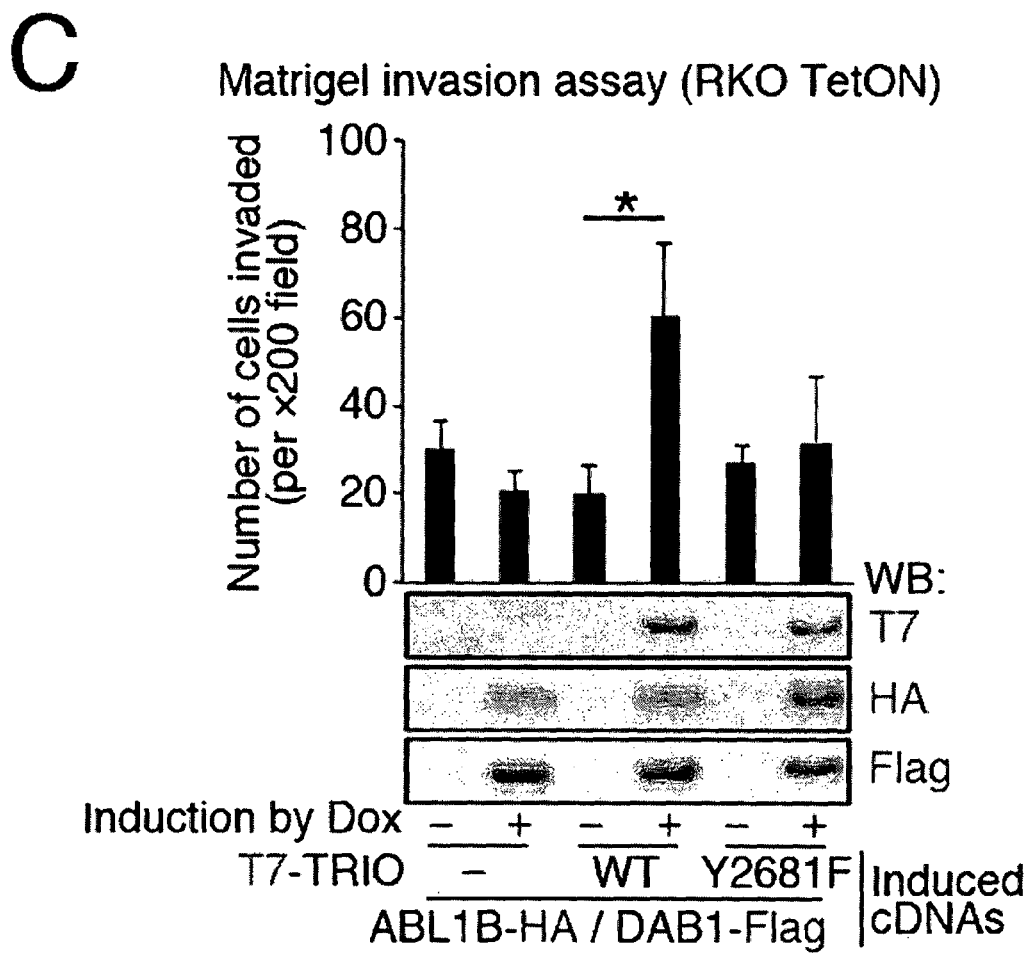

To study the roles of TRIO(pY2681) in CRC invasion, we constructed clonal RKO cells where either TRIO(WT) or unphosphorylatable TRIO(Y2681F) mutant was induced simultaneously with ABL1B and DAB1 in a doxycycline (Dox)-dependent manner (FIG. 7C). Interestingly, simultaneous expression of TRIO(WT) but not TRIO(Y2681F) with ABL1B and DAB1 stimulated the Matrigel invasion capacity of RKO cells (FIG. 7C).

Figure 7D:
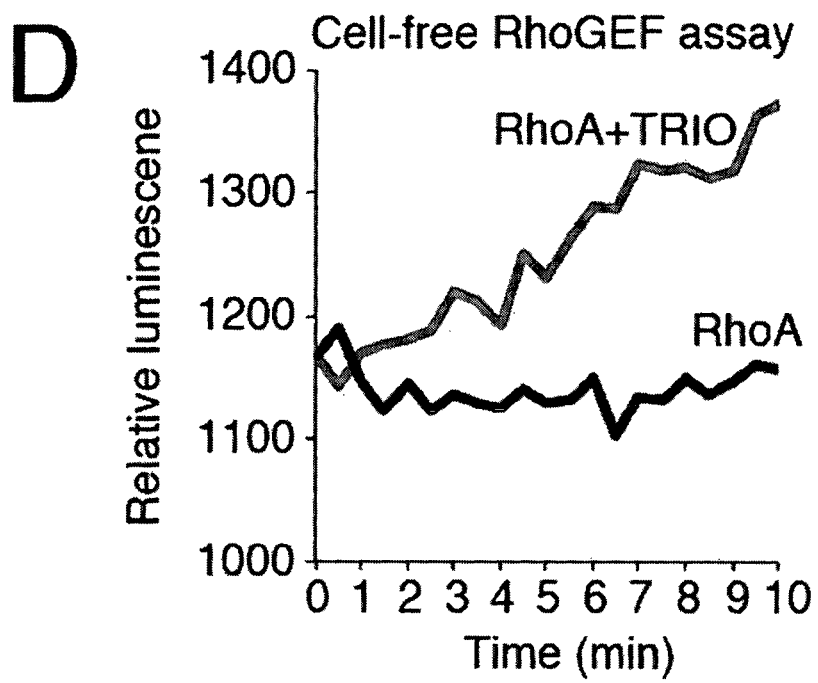
Figure 7E:
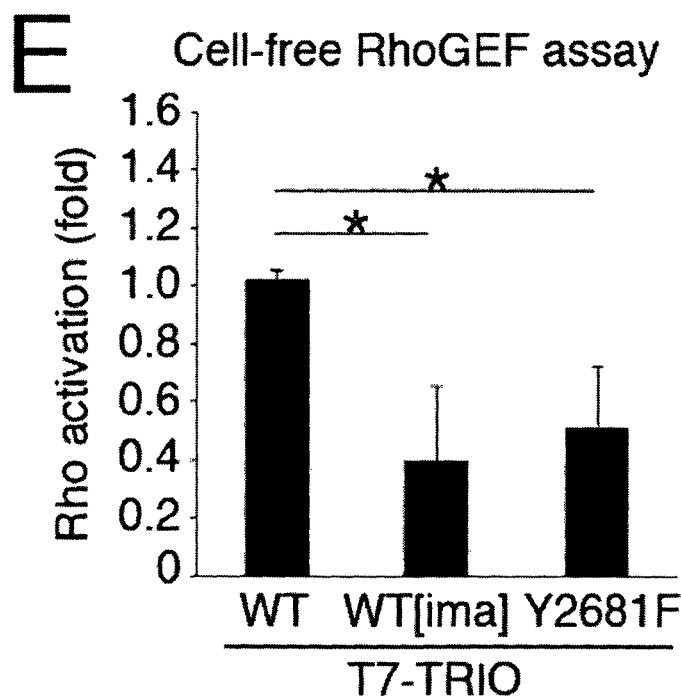

To evaluate the effects of TRIO Tyr-phosphorylation on Rho activation, we performed RhoGEF GTP-exchange assays in vitro using purified proteins. As TRIO-producing host cells, we chose HEK293T rather than CRC cells to avoid possibly confusing results by various gene mutations in CRC cells. We confirmed that TRIO(WT) protein purified from transfected cells stimulated the exchange reaction from GDP to GTP on recombinant RhoA as reported {Debant, 1996} (FIG. 7D). Importantly, TRIO(WT) purified from imatinib-treated transfectant cells showed significantly decreased capacity of Rho activation (FIG. 7E), suggesting critical effects by endogenous ABL kinase on Rho activation by TRIO. Notably, TRIO(Y2681F) showed similarly reduced GEF activity (FIG. 7E), indicating that phosphorylation at Y2681 is essential for its maximal GEF activity. These results collectively indicate that ABL causes phosphorylation of TRIO at Y2681 and increases GTP-Rho, resulting in enhanced invasion of CRC cells.

A TRIO Point Mutation in Human Cancer Stimulates its RhoGEF Activity

Figure 7F:
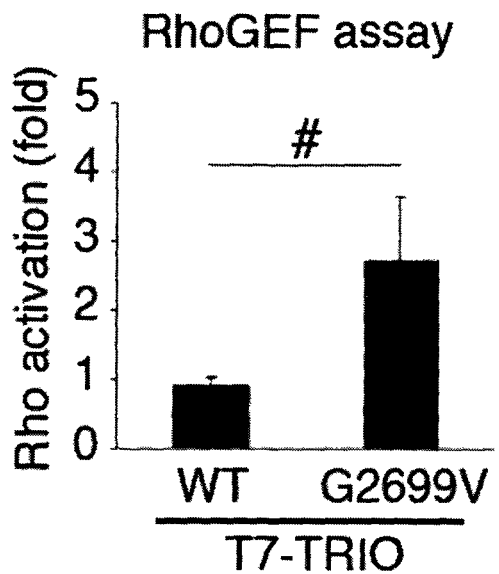
Figure 7G:
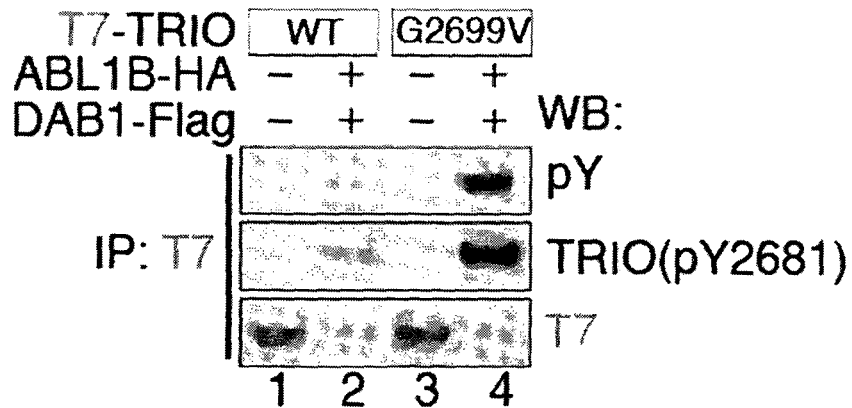

We further investigated possible TRIO mutations in human cancers. In the COSMIC (Catalogue of Somatic Mutations in Cancer) database, we found that 2% (102 among 4414) of various types of cancer contained 141 TRIO mutations. Notably, one mutation was found in CRC in the GEF2 domain (L2044I). We also found seven mutations in the Ig-like domain and its preceding region that contained Y2681. They were E2652G, G2658S, T2695M and S2767L in endometrial cancer, N2668S in breast, S2671Y in kidney, and G2699V (indicated by a star in FIG. 5A) in lung cancers. We constructed these point mutants of TRIO, and tested their RhoGEF activities. Interestingly, we found that the TRIO (G2699V) mutant was more capable of activating Rho than TRIO(WT), although it did not affect Rac activity (FIG. 7F and data not shown). Curiously, TRIO(G2699V) was more susceptible to Tyr-phosphorylation than wild-type in the presence of ABL and DAB1 (FIG. 7G). Collectively, these results suggest that TRIO mutations can activate RhoGEF capacity by boosting its Tyr-phosphorylation by DAB1-ABL, causing progression in a subset of human cancers.

TRIO(pY2681) is Found Various Types of Cancer

We further investigated whether Y2681 of TRIO is phosphorylated not only in the primary CRC but also in its metastasis as well as in other types of cancer. As a result, we found TRIO(pY2681) is present in the metastatic cells and also in various types of cancer (FIG. 12, Table 2). Those results indicate that this metastasis mechanism is critical in multiple types of cancer.

TABLE 2

Organs retaining TRIO(pY2681)

Adrenal gland
Blood (lymphoma)
Bone
Brain
Breast
Colorectum
Endometrium
Esophagus
Gallbladder
Kidney
Larynx
Liver
Lung
Oral cavity
Ovary
Pancreas
Prostate
Salivary gland
Skin
Small intestine (GIST)
Soft tissue
Stomach
Testis
Thyroid
Urinary bladder
Uterine cervix Types of Cancer that Show Strong Prognostic Correlation with TRIO(pY2681).

Regarding CRC, we have extended our study to a larger number of cases (FIG. 13). With the total number of 339 cases all stages combined, we have found statistically significant difference between the TRIO(pY2681)- and TRIO (pY2681)+ patients in their prognosis (P<0.001). Importantly, for the stage II patients (n=115), the five-year survival rate for the negative patients has turned out to be ~100%, whereas for those of Stage IV (n=57), the survival rate for the negative patients was ~50% and that for the positive patients was only ~10%.

Moreover, the patients of lung adenocarcinoma (n=214) showed significant difference in their prognosis between the TRIO(pY2681)-negative vs. -positive (P=0.002) (FIG. 14).

Likewise, the patients of gastric cancer in Stages (I-III), showed significant difference in their prognosis between the TRIO(pY2681)-negative vs. -positive (P<0.001) (FIG. 15).

In addition, preliminary data (n=20) have indicated a strong tendency that patients of pancreatic adenocarcinomas show better survival if their Trio(pY2681) is negative compared with those positive (FIG. 16). The statistical significance of this tendency was almost the same as that of another pancreatic cancer marker Smad4, although Trio (pY2681) and Smad4 are unrelated independent markers.

REFERENCES (ALL THE REFERENCES ARE HEREIN INCORPORATED BY REFERENCE)

Androutsellis-Theotokis, A., Leker, R. R., Soldner, F., Heppner, D. J., Ravin, R., Poser, S. W., Rueger, M. A., Bae, S.-K., Kittappa, R., and McKay, R. D. G. (2006). Notch signalling regulates stem cell numbers in vitro and in vivo. Nature 442, 823-826.

Arnaud, L., Ballif, B. A., Förster, E., and Cooper, J. A. (2003). Fyn tyrosine kinase is a critical regulator of Disabled-1 during brain development. Curr Biol 13, 9-17.

Artavanis-Tsakonas, S., Rand, M. D., and Lake, R. J. (1999). Notch signaling: cell fate control and signal integration in development. Science 284, 770-776.

Barilá, D., R., N., Gonfloni, S., Kretzchmar, J., Moro, M., Bohmann, D., and Superti-Furga, G. (2000). A nuclear tyrosine phosphorylation circuit: c-Jun as an activator and substrate of c-Abl and JNK. EMBO J 19, 273-281.

Bateman, J., and Van Vactor, D. (2001). The Trio family of guanine-nucleotide-edchange factors: regulators of axon guidance. J Cell Sci 114, 1973-1980.

Billadeau, D. D. (2010). Vav proteins in cancer. In The Rho GTPases in Cancer (Springer Science+Business Media, LLC), pp. 77-92.

Blom, N., Gammeltoft, S., and Brunak, S. (1999). Sequence- and structure-based prediction of eukaryotic protein phosphorylation sites. J Mol Biol 295, 1351-1362. Bock, H. H., and Herz, J. (2003). Reelin activates Src family tyrosine kinases in neurons. Current Biology 13, 18-26.

Buchdunger, E., Matter, A., and Druker, B. J. (2001). Bcr-Abl inhibition as a modality of CML therapeutics. BBA 1551, M11-M18.

Chen, W.-S., Kung, H.-J., Yang, W.-K., and Lin, W. (1999). Comparative tyrosine-kinase profiles in colorectal cancers: Enhanced Arg expression in carcinoma as compared with adenoma and normal mucosa. Int J Cancer 83, 579-584.

Colicelli, J. (2010). ABL tyrosine kinases: evolution of function, regulation, and specificity. Science Signaling 3, re6.

Debant, A., Serra-Pages, C., Seipel, K., O'Brien, S., Tang, M., Park, S.-H., and Streuli, M. (1996). The multidomain protein Trio binds the LAR transmembrane tyrosine phophatase, contains a protein kinase domain, and has separate rac-specific and rho-specific guanine nucleotide exchange factor domains. Proc Natl Acad Sci USA 93, 5466-5471.

DeGeer, J., Boudeau, J., Schmidt, S., Bedford, F., Lamarche-Vane, N., and Debant, A. (2013). Tyrosine phosphorylation of the Rho guanine nucleotide exchange factor Trio regulates netrin-1/DCC-mediated cortical axon outgrowth. Mol Cell Biol 33, 739-751.

Dowell, R. D. (2010). Transcription factor binding variation in the evolution of gene regulation. Trends Genet 26, 468-475.

Fidler, I. J. (2003). The pathogenesis of cancer metastasis: the "seed and soli" hypothesis revisited. Nat Rev Cancer 3, 453-458.

Forsthoefel, D. J., Liebl, E. C., Kolodziej, P. A., and Seeger, M. A. (2005). The Abelson tyrosine kinase, the Trio GEF and Enabled interact with the Netrin receptor Frazzled in *Drosophila*. Development 132, 1983-1994.

Gao, Y., Dickerson, J. B., Guo, F., Zheng, J., and Zheng, Y. (2004). Rational design and characterization of a Rac GTPase-specific small molecule inhibitor. Proc Natl Acad Sci USA 101, 7618-7623.

Giniger, E. (1998). A role for Abl in Notch signaling. Neuron 20, 667-681.

Giniger, E. (2012). Notch signaling and neural connectivity. Curr Opin Genet Dev 22, 1-8.

Hall, A. (1998). Rho GTPases and the actin cytoskeleton. Science 279, 509-514.

Hall, A. (2009). The cytoskeleton and cancer. Cancer Metastasis Rev 28, 5-14.

Han, H., Tanigaki, K., Yamamoto, N., Kuroda, K., Yoshimoto, M., Nakahata, T., Ikuta, K., and Honjo, T. (2002). Inducible gene knockout of transcription factor recombination signal binding protein-J reveals its essential role in T versus B lineage decision. International Immunology 14, 637-645.

Hantschel, O., and Superti-Furga, G. (2004). Regulation of the c-Abl and Bcr-Abl tyrosine kinases. Nat Rev Molcellbio 5, 33-44.

Hashimoto-Torii, K., Torii, M., Sarkisian, M. R., Bartley, C. M., Shen, J., Radtke, F., Gridley, G., Sestan, N., and Rakic, P. (2008). Interaction between Reelin and Notch signaling regurlates neuronal migration in the cerebral cortex. Neuron 60, 273-284.

Howell, B. W., Gertler, F. B., and Cooper, J. A. (1997). Mouse disabled (mDab1): a Src binding protein implicated in neuronal development. EMBO J 19, 121-132.

Kawasaki, Y., Senda, T., Ishidate, T., Koyama, R., Morishita, T., Iwayama, Y., Higuchi, O., and Akiyama, T. (2000). Asef, a link between the tumor suppressor APC and G-protein signaling. Science 289, 1194-1197.

Kakizaki F, Aoki K, Miyoshi H, Carrasco N, Aoki M and Taketo M M. (2010). CDX transcription factors positively regulate expression of solute carrier family 5, member 8 in the colonic epithelium. Gastroenterology 138, 627-635.

Krejci, A., Bernard, F., Huusden, B. E., Collins, S., and Bray, S. J. (2009). Direct response to Notch activation: signaling crosstalk and incoherent logic. Science Signaling 2, 1-14.

Li, Y., Hibbs, M. A., Gard, A. L., Shylo, N. A., and Yun, K. (2012). Genome-wide analysis of N1ICD/RBPJ targets in vivo reveals direct transcriptional regulation of Wnt, SHH, and Hippo pathway effectors by Notch1. Stem Cells 30, 741-752.

McDermott, U., Downing, J. R., and Stratton, M. R. (2011). Genomics and the continuum of cancer care. NEJM 364, 340-350.

Medley, Q. G., Serra-Pages, C., Iannotti, E., Seipel, K., Tang, M., O'Brien, S. P., and Streuli, M. (2000). The Trio guanine nucleaotide exchange factor is a RhoA target. J Biol Chem 275, 36116-36123.

Miles, F. L., Pruitt, F. L., van Golen, K. L., and Cooper, C. R. (2008). Stepping out of the flow: capillary extravasation in cancer metastasis. Clin Exp Metastasis 25, 305-324.

Nellesen D T, Lai E C, Posakony J W. (1999). Discrete enhancer elements mediate selective responsiveness of enhancer of split complex genes to common transcriptional activators. Dev Biol 213, 33-53.

Oshima, M., Oshima, H., Kitagawa, K., Kobayashi, M., Itakura, C., and Taketo, M. (1995). Loss of Apc heterozygosity and abnormal tissue building in nascent intestinal polyps in mice carrying a truncated Apc gene. Proc Natl Acad Sci USA 92, 4482-4486.

Rand, M. D., Grimm, L. M., Artavanis-Tsakonas, S., Patriub, V., Blacklow, S. C., Sklar, J., and Aster, J. C. (2000). Calcium depletion dissociates and activates heterodimeric Notch recepotors. Mol Biol Cell 20, 1825-1835.

Ranganathan, P., Weaver, K. L., and Capobianco, A. J. (2011). Notch signalling in solid tumors: a little bit of everything but not all the time. Nat Rev Cancer 11, 338-351.

Reymond, N., Riou, P. and Ridley, A. J. (2012). Rho GTPases and Cancer Cell Transendothelial Migration. in Rho GTPases: Methods and Protocols, Methods in Molecular Biology, Springer 827, 123-142.

Rossman K L, Worthylake D K, Snyder J T, Siderovski D P, Campbell S L and Sondek J. (2002). A crystallographic view of interactions between Dbs and Cdc42: PH domain-associated guanine nucleotide exchange. EMBO J. 21, 1315-1326.

Salazar, R., Roepman, P., Capella, G., Moreno, V., Simon, I., al., e., and Tollenaar, R. (2011). Gene expression siganture to improve prognosis prediction of stage II and stage III colorectal cancer. J Clin Oncol 29, 17-24.

Sanada, K., and Gupta, A. (2004). Disabled-1-regulated adhesion of migrating neurons to radial glial fiber contributes to neuronal positioning during early corticogenesis. Neuron 42, 197-211.

Sawyers, C. L. (2003). Opportunities and challenges in the development of kinase inhibitor therapy for cancer. Genes Dev 17, 2998-3010.

Song, J. K., and Giniger, E. (2011). Noncanonical Notch function in motor axon guidance is mediated by Rac GTPase and the GEF1 domain of Trio. Dev Dyn 240, 324-332.

Sonoshita, M., Aoki, M., Fuwa, H., Aoki, K., Hosogi, H., Sakai, Y., Hashida, H., Takabayashi, A., Sasaki, M., Robine, S., et al. (2011). Suppression of colon cancer metastasis by Aes through inhibition of Notch signaling. Cancer Cell 19, 125-137.

Steeg, P. S. (2003). Metastasis suppressors alter the signal transduction of cancer cells. Nat Rev Cancer 3, 55-63.

Steven, R., Kubiseski, T. J., Zheng, H., Kulkarni, S., Mancillas, J., Morales, A. R., Hogue, C. W. V., Pawson, T., and Culotti, J. (1998). UNC-73 activates the Rac GTPase and is required for cell and growth cone migrations in C. elegans. Cell 92, 785-795.

Tiyanont, K., Wales, T. E., Aste-Amezaga, M., Aster, J. C., Engen, J. R., and Blacklow, S. C. (2011). Evidence for increased exposure of the Notch1 metalloprotease cleavage site upon conversion to an activated conformation. Structure 19, 546-554.

Varnum-Finney, B., Wu, L., Yu, M., Brashem-Steln, C., Staats, S., Flowers, D., Griffin, J. D., and Berstein, I. D. (2000). Immobilization of Notch ligand, Delta-1, is required for induction of Notch signaling. J Cell Sci 113, 4313-4318.

Vigil, D., Cherfils, J., Rossman, K. L., and Der, C. J. (2010). Ras superfamily GEFs and GAPs: validated and tractable targets for cancer therapy? Nat Rev Cancer 10, 842-857.

Vooijs, M., Liu, Z., and Kopan, R. (2011). Notch: Architect, landscaper, and guardian of the intestine. Gastroenterology 141, 448-459.

Weinberg, R. A. (2007a). Cellular oncogenes. In The Biology of Cancer (New York: Garland Science), pp. 91-117.

Weinberg, R. A. (2007b). Moving out: invasion and metastasis. In The Biology of Cancer (Garland Science, New York), pp. 587-654.

Yoshizuka, N., Moriuchi, R., Mori, T., Yamada, K., Hasegawa, S., Maeda, T., Shimada, T., Yamada, Y., Kamihira, S., Momonaga, M., et al. (2004). An alternative transcript derived from the trio locus encodes a guanosine nucleotide exchange factor with mouse cell-transforming potential. J Biol Chem 279, 43998-44004.

The invention claimed is:

1. A method for determining prognosis of cancer in a subject, which comprises the step of detecting phosphorylation of a tyrosine residue of TRIO (pY2681) in a sample obtained from the subject, wherein phosphorylation is detected by an antibody that binds to TRIO (pY2681) and does not bind to unphosphorylated TRIO or phosphorylated TRIO other than TRIO (pY2681), and wherein absence of phosphorylation indicates good prognosis of cancer.

2. The method of claim 1, wherein the sample is a cancerous tissue which has been obtained from the primary tumor by surgical resection.

3. The method of claim 2, wherein absence of phosphorylation indicates likelihood of long survival after surgical resection of the primary tumor.

4. The method of claim 2, wherein presence of phosphorylation indicates necessity of adjuvant therapy after surgical resection of the primary tumor.

5. The method of claim 1, wherein phosphorylation is detected by immunohistochemistry assays, Western analysis or ELISA.

6. The method of claim 1, wherein the cancer is selected from the group consisting of colorectal cancer, breast cancer, lung cancer, pancreas cancer, and gastric cancer.

7. The method of claim 6, wherein the cancer is selected from the group consisting of colorectal cancer and gastric cancer.

8. The method of claim 7, wherein the cancer is colorectal cancer.

9. The method of claim 8, wherein the cancer is colorectal cancer at stage I or II.

10. The method of claim 9, wherein the cancer is colorectal cancer at stage II.

11. An antibody which specifically binds to TRIO (pY2681) and does not bind to unphosphorylated TRIO or phosphorylated TRIO other than TRIO (pY2681).

12. A diagnostic composition for determining prognosis of cancer which comprises the antibody of claim 11.

13. A kit for determining prognosis of cancer which comprises the antibody of claim 11.

* * * * *

SEQUENCE LISTING

<160> NUMBER OF SEQ ID NOS: 9

<210> SEQ ID NO 1
<211> LENGTH: 3097
<212> TYPE: PRT
<213> ORGANISM: Homo sapiens

<400> SEQUENCE: 1

```
Met Ser Gly Ser Ser Gly Gly Ala Ala Pro Ala Ala Ser Ser Gly
1               5                   10                  15

Pro Ala Ala Ala Ser Ala Ala Gly Ser Gly Cys Gly Gly Gly Ala
                20                  25                  30

Gly Glu Gly Ala Glu Glu Ala Ala Lys Asp Leu Ala Asp Ile Ala Ala
                35                  40                  45

Phe Phe Arg Ser Gly Phe Arg Lys Asn Asp Glu Met Lys Ala Met Asp
    50                  55                  60

Val Leu Pro Ile Leu Lys Glu Lys Val Ala Tyr Leu Ser Gly Gly Arg
65                  70                  75                  80

Asp Lys Arg Gly Gly Pro Ile Leu Thr Phe Pro Ala Arg Ser Asn His
                85                  90                  95

Asp Arg Ile Arg Gln Glu Asp Leu Arg Arg Leu Ile Ser Tyr Leu Ala
                100                 105                 110

Cys Ile Pro Ser Glu Glu Val Cys Lys Arg Gly Phe Thr Val Ile Val
                115                 120                 125

Asp Met Arg Gly Ser Lys Trp Asp Ser Ile Lys Pro Leu Leu Lys Ile
                130                 135                 140

Leu Gln Glu Ser Phe Pro Cys Cys Ile His Val Ala Leu Ile Ile Lys
145                 150                 155                 160

Pro Asp Asn Phe Trp Gln Lys Gln Arg Thr Asn Phe Gly Ser Ser Lys
                165                 170                 175

Phe Glu Phe Glu Thr Asn Met Val Ser Leu Glu Gly Leu Thr Lys Val
                180                 185                 190

Val Asp Pro Ser Gln Leu Thr Pro Glu Phe Asp Gly Cys Leu Glu Tyr
                195                 200                 205

Asn His Glu Glu Trp Ile Glu Ile Arg Val Ala Phe Glu Asp Tyr Ile
                210                 215                 220

Ser Asn Ala Thr His Met Leu Ser Arg Leu Glu Leu Gln Asp Ile
225                 230                 235                 240

Leu Ala Lys Lys Glu Leu Pro Gln Asp Leu Glu Gly Ala Arg Asn Met
                245                 250                 255

Ile Glu Glu His Ser Gln Leu Lys Lys Lys Val Ile Lys Ala Pro Ile
                260                 265                 270

Glu Asp Leu Asp Leu Glu Gly Gln Lys Leu Leu Gln Arg Ile Gln Ser
                275                 280                 285

Ser Glu Ser Phe Pro Lys Lys Asn Ser Gly Ser Gly Asn Ala Asp Leu
                290                 295                 300

Gln Asn Leu Leu Pro Lys Val Ser Thr Met Leu Asp Arg Leu His Ser
305                 310                 315                 320

Thr Arg Gln His Leu His Gln Met Trp His Val Arg Lys Leu Lys Leu
                325                 330                 335

Asp Gln Cys Phe Gln Leu Arg Leu Phe Glu Gln Asp Ala Glu Lys Met
                340                 345                 350

Phe Asp Trp Ile Thr His Asn Lys Gly Leu Phe Leu Asn Ser Tyr Thr
                355                 360                 365
```

-continued

```
Glu Ile Gly Thr Ser His Pro His Ala Met Glu Leu Gln Thr Gln His
    370                 375                 380
Asn His Phe Ala Met Asn Cys Met Asn Val Tyr Val Asn Ile Asn Arg
385                 390                 395                 400
Ile Met Ser Val Ala Asn Arg Leu Val Glu Ser Gly His Tyr Ala Ser
                405                 410                 415
Gln Gln Ile Arg Gln Ile Ala Ser Gln Leu Glu Gln Glu Trp Lys Ala
            420                 425                 430
Phe Ala Ala Leu Asp Glu Arg Ser Thr Leu Leu Asp Met Ser Ser
        435                 440                 445
Ile Phe His Gln Lys Ala Glu Lys Tyr Met Ser Asn Val Asp Ser Trp
    450                 455                 460
Cys Lys Ala Cys Gly Glu Val Asp Leu Pro Ser Glu Leu Gln Asp Leu
465                 470                 475                 480
Glu Asp Ala Ile His His Gln Gly Ile Tyr Glu His Ile Thr Leu
                485                 490                 495
Ala Tyr Ser Glu Val Ser Gln Asp Gly Lys Ser Leu Leu Asp Lys Leu
                500                 505                 510
Gln Arg Pro Leu Thr Pro Gly Ser Ser Asp Ser Leu Thr Ala Ser Ala
            515                 520                 525
Asn Tyr Ser Lys Ala Val His Val Leu Asp Val Ile His Glu Val
    530                 535                 540
Leu His His Gln Arg Gln Leu Glu Asn Ile Trp Gln His Arg Lys Val
545                 550                 555                 560
Arg Leu His Gln Arg Leu Gln Leu Cys Val Phe Gln Gln Asp Val Gln
                565                 570                 575
Gln Val Leu Asp Trp Ile Glu Asn His Gly Glu Ala Phe Leu Ser Lys
            580                 585                 590
His Thr Gly Val Gly Lys Ser Leu His Arg Ala Arg Ala Leu Gln Lys
        595                 600                 605
Arg His Glu Asp Phe Glu Val Ala Gln Asn Thr Tyr Thr Asn Ala
    610                 615                 620
Asp Lys Leu Leu Glu Ala Ala Glu Gln Leu Ala Gln Thr Gly Glu Cys
625                 630                 635                 640
Asp Pro Glu Glu Ile Tyr Gln Ala Ala His Gln Leu Glu Asp Arg Ile
                645                 650                 655
Gln Asp Phe Val Arg Arg Val Glu Gln Arg Lys Ile Leu Leu Asp Met
            660                 665                 670
Ser Val Ser Phe His Thr His Val Lys Glu Leu Trp Thr Trp Leu Glu
        675                 680                 685
Glu Leu Gln Lys Glu Leu Leu Asp Asp Val Tyr Ala Glu Ser Val Glu
    690                 695                 700
Ala Val Gln Asp Leu Ile Lys Arg Phe Gly Gln Gln Gln Thr Thr
705                 710                 715                 720
Leu Gln Val Thr Val Asn Val Ile Lys Glu Gly Glu Asp Leu Ile Gln
                725                 730                 735
Gln Leu Arg Asp Ser Ala Ile Ser Ser Asn Lys Thr Pro His Asn Ser
            740                 745                 750
Ser Ile Asn His Ile Glu Thr Val Leu Gln Gln Leu Asp Glu Ala Gln
        755                 760                 765
Ser Gln Met Glu Glu Leu Phe Gln Glu Arg Lys Ile Lys Leu Glu Leu
    770                 775                 780
Phe Leu Gln Leu Arg Ile Phe Glu Arg Asp Ala Ile Asp Ile Ile Ser
```

-continued

```
            785                 790                 795                 800
Asp Leu Glu Ser Trp Asn Asp Glu Leu Ser Gln Gln Met Asn Asp Phe
                    805                 810                 815
Asp Thr Glu Asp Leu Thr Ile Ala Glu Gln Arg Leu Gln His His Ala
                    820                 825                 830
Asp Lys Ala Leu Thr Met Asn Asn Leu Thr Phe Asp Val Ile His Gln
                    835                 840                 845
Gly Gln Asp Leu Leu Gln Tyr Val Asn Glu Val Gln Ala Ser Gly Val
                    850                 855                 860
Glu Leu Leu Cys Asp Arg Asp Val Asp Met Ala Thr Arg Val Gln Asp
865                 870                 875                 880
Leu Leu Glu Phe Leu His Glu Lys Gln Gln Glu Leu Asp Leu Ala Ala
                    885                 890                 895
Glu Gln His Arg Lys His Leu Glu Gln Cys Val Gln Leu Arg His Leu
                    900                 905                 910
Gln Ala Glu Val Lys Gln Val Leu Gly Trp Ile Arg Asn Gly Glu Ser
                    915                 920                 925
Met Leu Asn Ala Gly Leu Ile Thr Ala Ser Ser Leu Gln Glu Ala Glu
                    930                 935                 940
Gln Leu Gln Arg Glu His Glu Gln Phe Gln His Ala Ile Glu Lys Thr
945                 950                 955                 960
His Gln Ser Ala Leu Gln Val Gln Gln Lys Ala Glu Ala Met Leu Gln
                    965                 970                 975
Ala Asn His Tyr Asp Met Asp Met Ile Arg Asp Cys Ala Glu Lys Val
                    980                 985                 990
Ala Ser His Trp Gln Gln Leu Met Leu Lys Met Glu Asp Arg Leu Lys
                    995                 1000                1005
Leu Val Asn Ala Ser Val Ala Phe Tyr Lys Thr Ser Glu Gln Val
                    1010                1015                1020
Cys Ser Val Leu Glu Ser Leu Glu Gln Glu Tyr Lys Arg Glu Glu
                    1025                1030                1035
Asp Trp Cys Gly Gly Ala Asp Lys Leu Gly Pro Asn Ser Glu Thr
                    1040                1045                1050
Asp His Val Thr Pro Met Ile Ser Lys His Leu Glu Gln Lys Glu
                    1055                1060                1065
Ala Phe Leu Lys Ala Cys Thr Leu Ala Arg Arg Asn Ala Asp Val
                    1070                1075                1080
Phe Leu Lys Tyr Leu His Arg Asn Ser Val Asn Met Pro Gly Met
                    1085                1090                1095
Val Thr His Ile Lys Ala Pro Glu Gln Gln Val Lys Asn Ile Leu
                    1100                1105                1110
Asn Glu Leu Phe Gln Arg Glu Asn Arg Val Leu His Tyr Trp Thr
                    1115                1120                1125
Met Arg Lys Arg Arg Leu Asp Gln Cys Gln Gln Tyr Val Val Phe
                    1130                1135                1140
Glu Arg Ser Ala Lys Gln Ala Leu Glu Trp Ile His Asp Asn Gly
                    1145                1150                1155
Glu Phe Tyr Leu Ser Thr His Thr Ser Thr Gly Ser Ser Ile Gln
                    1160                1165                1170
His Thr Gln Glu Leu Leu Lys Glu His Glu Glu Phe Gln Ile Thr
                    1175                1180                1185
Ala Lys Gln Thr Lys Glu Arg Val Lys Leu Leu Ile Gln Leu Ala
                    1190                1195                1200
```

```
Asp Gly Phe Cys Glu Lys Gly His Ala His Ala Ala Glu Ile Lys
    1205                1210                1215

Lys Cys Val Thr Ala Val Asp Lys Arg Tyr Arg Asp Phe Ser Leu
    1220                1225                1230

Arg Met Glu Lys Tyr Arg Thr Ser Leu Glu Lys Ala Leu Gly Ile
    1235                1240                1245

Ser Ser Asp Ser Asn Lys Ser Ser Lys Ser Leu Gln Leu Asp Ile
    1250                1255                1260

Ile Pro Ala Ser Ile Pro Gly Ser Glu Val Lys Leu Arg Asp Ala
    1265                1270                1275

Ala His Glu Leu Asn Glu Glu Lys Arg Lys Ser Ala Arg Arg Lys
    1280                1285                1290

Glu Phe Ile Met Ala Glu Leu Ile Gln Thr Glu Lys Ala Tyr Val
    1295                1300                1305

Arg Asp Leu Arg Glu Cys Met Asp Thr Tyr Leu Trp Glu Met Thr
    1310                1315                1320

Ser Gly Val Glu Glu Ile Pro Pro Gly Ile Val Asn Lys Glu Leu
    1325                1330                1335

Ile Ile Phe Gly Asn Met Gln Glu Ile Tyr Glu Phe His Asn Asn
    1340                1345                1350

Ile Phe Leu Lys Glu Leu Glu Lys Tyr Glu Gln Leu Pro Glu Asp
    1355                1360                1365

Val Gly His Cys Phe Val Thr Trp Ala Asp Lys Phe Gln Met Tyr
    1370                1375                1380

Val Thr Tyr Cys Lys Asn Lys Pro Asp Ser Thr Gln Leu Ile Leu
    1385                1390                1395

Glu His Ala Gly Ser Tyr Phe Asp Glu Ile Gln Gln Arg His Gly
    1400                1405                1410

Leu Ala Asn Ser Ile Ser Ser Tyr Leu Ile Lys Pro Val Gln Arg
    1415                1420                1425

Ile Thr Lys Tyr Gln Leu Leu Leu Lys Glu Leu Leu Thr Cys Cys
    1430                1435                1440

Glu Glu Gly Lys Gly Glu Ile Lys Asp Gly Leu Glu Val Met Leu
    1445                1450                1455

Ser Val Pro Lys Arg Ala Asn Asp Ala Met His Leu Ser Met Leu
    1460                1465                1470

Glu Gly Phe Asp Glu Asn Ile Glu Ser Gln Gly Glu Leu Ile Leu
    1475                1480                1485

Gln Glu Ser Phe Gln Val Trp Asp Pro Lys Thr Leu Ile Arg Lys
    1490                1495                1500

Gly Arg Glu Arg His Leu Phe Leu Phe Glu Met Ser Leu Val Phe
    1505                1510                1515

Ser Lys Glu Val Lys Asp Ser Ser Gly Arg Ser Lys Tyr Leu Tyr
    1520                1525                1530

Lys Ser Lys Leu Phe Thr Ser Glu Leu Gly Val Thr Glu His Val
    1535                1540                1545

Glu Gly Asp Pro Cys Lys Phe Ala Leu Trp Val Gly Arg Thr Pro
    1550                1555                1560

Thr Ser Asp Asn Lys Ile Val Leu Lys Ala Ser Ser Ile Glu Asn
    1565                1570                1575

Lys Gln Asp Trp Ile Lys His Ile Arg Glu Val Ile Gln Glu Arg
    1580                1585                1590
```

```
Thr Ile His Leu Lys Gly Ala Leu Lys Glu Pro Ile His Ile Pro
1595                1600                1605

Lys Thr Ala Pro Ala Thr Arg Gln Lys Gly Arg Arg Asp Gly Glu
1610                1615                1620

Asp Leu Asp Ser Gln Gly Asp Gly Ser Ser Gln Pro Asp Thr Ile
1625                1630                1635

Ser Ile Ala Ser Arg Thr Ser Gln Asn Thr Leu Asp Ser Asp Lys
1640                1645                1650

Leu Ser Gly Gly Cys Glu Leu Thr Val Val Ile His Asp Phe Thr
1655                1660                1665

Ala Cys Asn Ser Asn Glu Leu Thr Ile Arg Arg Gly Gln Thr Val
1670                1675                1680

Glu Val Leu Glu Arg Pro His Asp Lys Pro Asp Trp Cys Leu Val
1685                1690                1695

Arg Thr Thr Asp Arg Ser Pro Ala Ala Glu Gly Leu Val Pro Cys
1700                1705                1710

Gly Ser Leu Cys Ile Ala His Ser Arg Ser Ser Met Glu Met Glu
1715                1720                1725

Gly Ile Phe Asn His Lys Asp Ser Leu Ser Val Ser Ser Asn Asp
1730                1735                1740

Ala Ser Pro Pro Ala Ser Val Ala Ser Leu Gln Pro His Met Ile
1745                1750                1755

Gly Ala Gln Ser Ser Pro Gly Pro Lys Arg Pro Gly Asn Thr Leu
1760                1765                1770

Arg Lys Trp Leu Thr Ser Pro Val Arg Arg Leu Ser Ser Gly Lys
1775                1780                1785

Ala Asp Gly His Val Lys Lys Leu Ala His Lys His Lys Lys Ser
1790                1795                1800

Arg Glu Val Arg Lys Ser Ala Asp Ala Gly Ser Gln Lys Asp Ser
1805                1810                1815

Asp Asp Ser Ala Ala Thr Pro Gln Asp Glu Thr Val Glu Glu Arg
1820                1825                1830

Gly Arg Asn Glu Gly Leu Ser Ser Gly Thr Leu Ser Lys Ser Ser
1835                1840                1845

Ser Ser Gly Met Gln Ser Cys Gly Glu Glu Gly Glu Glu Gly
1850                1855                1860

Ala Asp Ala Val Pro Leu Pro Pro Met Ala Ile Gln Gln His
1865                1870                1875

Ser Leu Leu Gln Pro Asp Ser Gln Asp Asp Lys Ala Ser Ser Arg
1880                1885                1890

Leu Leu Val Arg Pro Thr Ser Ser Glu Thr Pro Ser Ala Ala Glu
1895                1900                1905

Leu Val Ser Ala Ile Glu Glu Leu Val Lys Ser Lys Met Ala Leu
1910                1915                1920

Glu Asp Arg Pro Ser Ser Leu Leu Val Asp Gln Gly Asp Ser Ser
1925                1930                1935

Ser Pro Ser Phe Asn Pro Ser Asp Asn Ser Leu Leu Ser Ser Ser
1940                1945                1950

Ser Pro Ile Asp Glu Met Glu Glu Arg Lys Ser Ser Ser Leu Lys
1955                1960                1965

Arg Arg His Tyr Val Leu Gln Glu Leu Val Glu Thr Glu Arg Asp
1970                1975                1980

Tyr Val Arg Asp Leu Gly Tyr Val Val Glu Gly Tyr Met Ala Leu
```

-continued

```
            1985                1990                1995
Met Lys Glu Asp Gly Val Pro Asp Asp Met Lys Gly Lys Asp Lys
            2000                2005                2010

Ile Val Phe Gly Asn Ile His Gln Ile Tyr Asp Trp His Arg Asp
            2015                2020                2025

Phe Phe Leu Gly Glu Leu Glu Lys Cys Leu Glu Asp Pro Glu Lys
            2030                2035                2040

Leu Gly Ser Leu Phe Val Lys His Glu Arg Arg Leu His Met Tyr
            2045                2050                2055

Ile Ala Tyr Cys Gln Asn Lys Pro Lys Ser Glu His Ile Val Ser
            2060                2065                2070

Glu Tyr Ile Asp Thr Phe Phe Glu Asp Leu Lys Gln Arg Leu Gly
            2075                2080                2085

His Arg Leu Gln Leu Thr Asp Leu Leu Ile Lys Pro Val Gln Arg
            2090                2095                2100

Ile Met Lys Tyr Gln Leu Leu Leu Lys Asp Phe Leu Lys Tyr Ser
            2105                2110                2115

Lys Lys Ala Ser Leu Asp Thr Ser Glu Leu Glu Arg Ala Val Glu
            2120                2125                2130

Val Met Cys Ile Val Pro Arg Arg Cys Asn Asp Met Met Asn Val
            2135                2140                2145

Gly Arg Leu Gln Gly Phe Asp Gly Lys Ile Val Ala Gln Gly Lys
            2150                2155                2160

Leu Leu Leu Gln Asp Thr Phe Leu Val Thr Asp Gln Asp Ala Gly
            2165                2170                2175

Leu Leu Pro Arg Cys Arg Glu Arg Arg Ile Phe Leu Phe Glu Gln
            2180                2185                2190

Ile Val Ile Phe Ser Glu Pro Leu Asp Lys Lys Lys Gly Phe Ser
            2195                2200                2205

Met Pro Gly Phe Leu Phe Lys Asn Ser Ile Lys Val Ser Cys Leu
            2210                2215                2220

Cys Leu Glu Glu Asn Val Glu Asn Asp Pro Cys Lys Phe Ala Leu
            2225                2230                2235

Thr Ser Arg Thr Gly Asp Val Val Glu Thr Phe Ile Leu His Ser
            2240                2245                2250

Ser Ser Pro Ser Val Arg Gln Thr Trp Ile His Glu Ile Asn Gln
            2255                2260                2265

Ile Leu Glu Asn Gln Arg Asn Phe Leu Asn Ala Leu Thr Ser Pro
            2270                2275                2280

Ile Glu Tyr Gln Arg Asn His Ser Gly Gly Gly Gly Gly Gly Gly
            2285                2290                2295

Ser Gly Gly Ser Gly Gly Gly Gly Ser Gly Gly Gly Ala
            2300                2305                2310

Pro Ser Gly Gly Ser Gly His Ser Gly Gly Pro Ser Ser Cys Gly
            2315                2320                2325

Gly Ala Pro Ser Thr Ser Arg Ser Arg Pro Ser Arg Ile Pro Gln
            2330                2335                2340

Pro Val Arg His His Pro Val Leu Val Ser Ser Ala Ala Ser
            2345                2350                2355

Ser Gln Ala Glu Ala Asp Lys Met Ser Gly Thr Ser Thr Pro Gly
            2360                2365                2370

Pro Ser Leu Pro Pro Pro Gly Ala Ala Pro Glu Ala Gly Pro Ser
            2375                2380                2385
```

```
Ala Pro Ser Arg Pro Pro Gly Ala Asp Ala Glu Gly Ser Glu
    2390            2395            2400

Arg Glu Ala Glu Pro Ile Pro Lys Met Lys Val Leu Glu Ser Pro
    2405            2410            2415

Arg Lys Gly Ala Ala Asn Ala Ser Gly Ser Ser Pro Asp Ala Pro
    2420            2425            2430

Ala Lys Asp Ala Arg Ala Ser Leu Gly Thr Leu Pro Leu Gly Lys
    2435            2440            2445

Pro Arg Ala Gly Ala Ala Ser Pro Leu Asn Ser Pro Leu Ser Ser
    2450            2455            2460

Ala Val Pro Ser Leu Gly Lys Glu Pro Phe Pro Pro Ser Ser Pro
    2465            2470            2475

Leu Gln Lys Gly Gly Ser Phe Trp Ser Ser Ile Pro Ala Ser Pro
    2480            2485            2490

Ala Ser Arg Pro Gly Ser Phe Thr Phe Pro Gly Asp Ser Asp Ser
    2495            2500            2505

Leu Gln Arg Gln Thr Pro Arg His Ala Ala Pro Gly Lys Asp Thr
    2510            2515            2520

Asp Arg Met Ser Thr Cys Ser Ser Ala Ser Glu Gln Ser Val Gln
    2525            2530            2535

Ser Thr Gln Ser Asn Gly Ser Glu Ser Ser Ser Ser Asn Ile
    2540            2545            2550

Ser Thr Met Leu Val Thr His Asp Tyr Thr Ala Val Lys Glu Asp
    2555            2560            2565

Glu Ile Asn Val Tyr Gln Gly Glu Val Val Gln Ile Leu Ala Ser
    2570            2575            2580

Asn Gln Gln Asn Met Phe Leu Val Phe Arg Ala Ala Thr Asp Gln
    2585            2590            2595

Cys Pro Ala Ala Glu Gly Trp Ile Pro Gly Phe Val Leu Gly His
    2600            2605            2610

Thr Ser Ala Val Ile Val Glu Asn Pro Asp Gly Thr Leu Lys Lys
    2615            2620            2625

Ser Thr Ser Trp His Thr Ala Leu Arg Leu Arg Lys Lys Ser Glu
    2630            2635            2640

Lys Lys Asp Lys Asp Gly Lys Arg Glu Gly Lys Leu Glu Asn Gly
    2645            2650            2655

Tyr Arg Lys Ser Arg Glu Gly Leu Ser Asn Lys Val Ser Val Lys
    2660            2665            2670

Leu Leu Asn Pro Asn Tyr Ile Tyr Asp Val Pro Pro Glu Phe Val
    2675            2680            2685

Ile Pro Leu Ser Glu Val Thr Cys Glu Thr Gly Glu Thr Val Val
    2690            2695            2700

Leu Arg Cys Arg Val Cys Gly Arg Pro Lys Ala Ser Ile Thr Trp
    2705            2710            2715

Lys Gly Pro Glu His Asn Thr Leu Asn Asn Asp Gly His Tyr Ser
    2720            2725            2730

Ile Ser Tyr Ser Asp Leu Gly Glu Ala Thr Leu Lys Ile Val Gly
    2735            2740            2745

Val Thr Thr Glu Asp Asp Gly Ile Tyr Thr Cys Ile Ala Val Asn
    2750            2755            2760

Asp Met Gly Ser Ala Ser Ser Ala Ser Leu Arg Val Leu Gly
    2765            2770            2775
```

```
Pro Gly Met Asp Gly Ile Met Val Thr Trp Lys Asp Asn Phe Asp
    2780            2785                2790
Ser Phe Tyr Ser Glu Val Ala Glu Leu Gly Arg Gly Arg Phe Ser
    2795            2800                2805
Val Val Lys Lys Cys Asp Gln Lys Gly Thr Lys Arg Ala Val Ala
    2810            2815                2820
Thr Lys Phe Val Asn Lys Lys Leu Met Lys Arg Asp Gln Val Thr
    2825            2830                2835
His Glu Leu Gly Ile Leu Gln Ser Leu Gln His Pro Leu Leu Val
    2840            2845                2850
Gly Leu Leu Asp Thr Phe Glu Thr Pro Thr Ser Tyr Ile Leu Val
    2855            2860                2865
Leu Glu Met Ala Asp Gln Gly Arg Leu Leu Asp Cys Val Val Arg
    2870            2875                2880
Trp Gly Ser Leu Thr Glu Gly Lys Ile Arg Ala His Leu Gly Glu
    2885            2890                2895
Val Leu Glu Ala Val Arg Tyr Leu His Asn Cys Arg Ile Ala His
    2900            2905                2910
Leu Asp Leu Lys Pro Glu Asn Ile Leu Val Asp Glu Ser Leu Ala
    2915            2920                2925
Lys Pro Thr Ile Lys Leu Ala Asp Phe Gly Asp Ala Val Gln Leu
    2930            2935                2940
Asn Thr Thr Tyr Tyr Ile His Gln Leu Leu Gly Asn Pro Glu Phe
    2945            2950                2955
Ala Ala Pro Glu Ile Ile Leu Gly Asn Pro Val Ser Leu Thr Ser
    2960            2965                2970
Asp Thr Trp Ser Val Gly Val Leu Thr Tyr Val Leu Leu Ser Gly
    2975            2980                2985
Val Ser Pro Phe Leu Asp Asp Ser Val Glu Glu Thr Cys Leu Asn
    2990            2995                3000
Ile Cys Arg Leu Asp Phe Ser Phe Pro Asp Asp Tyr Phe Lys Gly
    3005            3010                3015
Val Ser Gln Lys Ala Lys Glu Phe Val Cys Phe Leu Leu Gln Glu
    3020            3025                3030
Asp Pro Ala Lys Arg Pro Ser Ala Ala Leu Ala Leu Gln Glu Gln
    3035            3040                3045
Trp Leu Gln Ala Gly Asn Gly Arg Ser Thr Gly Val Leu Asp Thr
    3050            3055                3060
Ser Arg Leu Thr Ser Phe Ile Glu Arg Arg Lys His Gln Asn Asp
    3065            3070                3075
Val Arg Pro Ile Arg Ser Ile Lys Asn Phe Leu Gln Ser Arg Leu
    3080            3085                3090
Leu Pro Arg Val
    3095
```

<210> SEQ ID NO 2
<211> LENGTH: 21
<212> TYPE: DNA
<213> ORGANISM: Artificial Sequence
<220> FEATURE:
<223> OTHER INFORMATION: Knockdown sequence for DAB1

<400> SEQUENCE: 2
aaggattaag taggatgtca a                                         21

```
<210> SEQ ID NO 3
<211> LENGTH: 21
<212> TYPE: DNA
<213> ORGANISM: Artificial Sequence
<220> FEATURE:
<223> OTHER INFORMATION: Knockdown sequence for DAB1

<400> SEQUENCE: 3
ccggtacaaa gccaaattga t                                              21

<210> SEQ ID NO 4
<211> LENGTH: 19
<212> TYPE: DNA
<213> ORGANISM: Artificial Sequence
<220> FEATURE:
<223> OTHER INFORMATION: PCR primer

<400> SEQUENCE: 4
cgtgtctcct cctcccatt                                                 19

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
gaacggctcg tgtgaaactt                                                20

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
caagctctgt gcttgtctca                                                20

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
gtagctgtgt ggtcttatca                                                20

<210> SEQ ID NO 8
<211> LENGTH: 10
<212> TYPE: PRT
<213> ORGANISM: Artificial Sequence
<220> FEATURE:
<223> OTHER INFORMATION: Peptide derived from TRIO (pY1990)
<220> FEATURE:
<221> NAME/KEY: PHOSPHORYLATION
<222> LOCATION: (6)..(6)

<400> SEQUENCE: 8

Val Arg Asp Leu Gly Tyr Val Val Glu Gly
1               5                   10

<210> SEQ ID NO 9
<211> LENGTH: 11
<212> TYPE: PRT
```

```
<213> ORGANISM: Artificial Sequence
<220> FEATURE:
<223> OTHER INFORMATION: Peptide derived from TRIO (pY2681)
<220> FEATURE:
<221> NAME/KEY: PHOSPHORYLATION
<222> LOCATION: (6)..(6)

<400> SEQUENCE: 9

Asn Pro Asn Tyr Ile Tyr Asp Val Pro Pro Glu
1               5                   10
```